(12) United States Patent
Lee

(10) Patent No.: US 9,997,722 B2
(45) Date of Patent: Jun. 12, 2018

(54) COMPOUND AND ORGANIC LIGHT-EMITTING DEVICE INCLUDING THE SAME

(71) Applicant: Samsung Display Co., Ltd., Yongin-si, Gyeonggi-do (KR)

(72) Inventor: Jungsub Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 150 days.

(21) Appl. No.: 15/069,721

(22) Filed: Mar. 14, 2016

(65) Prior Publication Data

US 2017/0069849 A1     Mar. 9, 2017

(30) Foreign Application Priority Data

Sep. 8, 2015   (KR) .................... 10-2015-0127032

(51) Int. Cl.
*H01L 51/00*     (2006.01)
*H01L 27/32*     (2006.01)
(Continued)

(52) U.S. Cl.
CPC ........ *H01L 51/0072* (2013.01); *C07F 9/6561* (2013.01); *H01L 27/3244* (2013.01);
(Continued)

(58) Field of Classification Search
None
See application file for complete search history.

(56) References Cited

U.S. PATENT DOCUMENTS 3,337,545 A * 8/1967 Zirkle .................. C07D 471/06
544/102
5,645,948 A   7/1997 Shi et al.
(Continued)

FOREIGN PATENT DOCUMENTS

EP   0 700 917 A2   9/1995
JP   10-17860 A     1/1998
(Continued)

OTHER PUBLICATIONS

Li et al. one page exerpt from Organic Light-Emitting Materials and Devices, 2005, 1 page.*
(Continued)

*Primary Examiner* — Robert S Loewe
(74) *Attorney, Agent, or Firm* — Lewis Roca Rothgerber Christie LLP

(57) ABSTRACT

An organic light-emitting device includes: a first electrode; a second electrode facing the first electrode; and an organic layer between the first electrode and the second electrode, the organic layer including an emission layer, wherein the organic layer includes the compound represented by Formula 1:

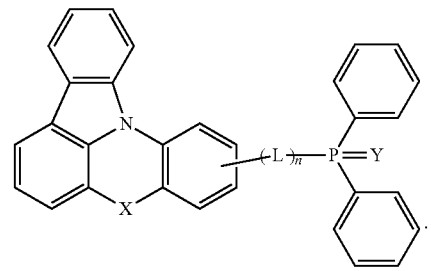

The organic light-emitting device according to embodiments of the present disclosure may have high efficiency and long lifespan characteristics.

20 Claims, 1 Drawing Sheet

(51) Int. Cl.
*C07F 9/6561* (2006.01)
*H01L 51/50* (2006.01)

(52) U.S. Cl.
CPC ...... *H01L 51/0052* (2013.01); *H01L 51/0067* (2013.01); *H01L 51/0071* (2013.01); *H01L 51/5016* (2013.01); *H01L 51/5072* (2013.01)

(56) References Cited

U.S. PATENT DOCUMENTS

| | | | |
|---|---|---|---|
| 6,083,634 A | 7/2000 | Shi | |
| 6,171,715 B1 | 1/2001 | Sato et al. | |
| 2007/0247059 A1* | 10/2007 | Cho | C07D 221/20 313/499 |
| 2009/0136779 A1* | 5/2009 | Cheng | C07D 471/06 428/690 |
| 2012/0068168 A1* | 3/2012 | Lee | C07F 9/5728 257/40 |
| 2012/0202997 A1 | 8/2012 | Parham et al. | |
| 2015/0259347 A1* | 9/2015 | Park | C07D 471/10 257/40 |

FOREIGN PATENT DOCUMENTS

| | | | | |
|---|---|---|---|---|
| JP | 11-87067 A | 3/1999 | | |
| JP | 11-345686 A | 12/1999 | | |
| JP | 2002-63989 A | 2/2002 | | |
| JP | 2004-204140 A | 7/2004 | | |
| JP | 2012248663 A | * 12/2012 | ............ | H01L 51/50 |
| KR | 10-2012-0087935 A | 8/2012 | | |
| KR | 10-2013-0135178 A | 12/2013 | | |
| KR | 10-2014-0128892 A | 11/2014 | | |
| KR | 10-2014-0141970 A | 12/2014 | | |
| KR | 10-2015-0007570 A | 1/2015 | | |

OTHER PUBLICATIONS

Machine translation of JP-2012248663, translation generated Jun. 2017, 32 pages.*
He et al. "Very high-efficiency and low voltage phosphorescent organic light-emitting diodes based on a p-i-n junction" J. Appl. Phys. 95, 2004, 5773-5777.*
Katritzky et al., "Polycyclic Fused Phenanthridines: An Alternative Approach from Benzotriazoles", Journal of Heterocyclic Chemistry, vol. 36, pp. 927-932 (1999).

* cited by examiner

| 190 |
|---|
| 150 |
| 110 |

COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2015-0127032, filed on Sep. 8, 2015, in the Korean Intellectual Property Office, the entire disclosure of which is incorporated herein by reference.

BACKGROUND

1. Field

One or more aspects of example embodiments of the present disclosure relate to a compound and an organic light-emitting device including the same.

2. Description of the Related Art

Organic light-emitting devices (OLEDs) are self-emitting devices that have wide viewing angles, high contrast ratios, and short response times. OLEDs also exhibit excellent brightness, driving voltage, and response speed characteristics, and can produce multicolored images.

An OLED may include a first electrode disposed (e.g., positioned) on a substrate, and a hole transport region, an emission layer, an electron transport region, and a second electrode, which are sequentially disposed on the first electrode. Holes provided from the first electrode move toward the emission layer through the hole transport region, and electrons provided from the second electrode move toward the emission layer through the electron transport region. Carriers, such as the holes and electrons, are then recombined in the emission layer to produce excitons. These excitons change from an excited state to a ground state, thereby generating light.

SUMMARY

One or more aspects of example embodiments of the present disclosure are directed toward a compound for an organic light-emitting device having improved high efficiency and long lifespan characteristics, and an organic light-emitting device including the compound.

Additional aspects will be set forth in part in the description which follows and, in part, will be apparent from the description, or may be learned by practice of the presented embodiments.

According to one or more example embodiments, there is provided a compound represented by Formula 1:

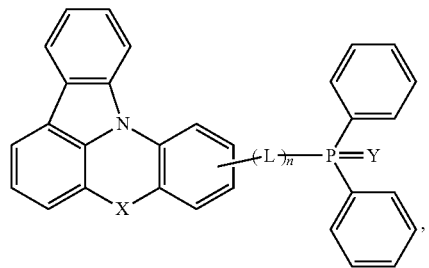

Formula 1 wherein, in Formula 1,

X may be selected from $NR_1$, S, O, and $CR_2R_3$, n may be an integer selected from 0 to 2, Y may be selected from O, S, and Se, $R_1$ to $R_3$ may each be independently selected from hydrogen, deuterium, a halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and L may be selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, wherein at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group, the substituted $C_6$-$C_{60}$ arylene group, the substituted $C_1$-$C_{60}$ heteroarylene group, the substituted divalent non-aromatic condensed polycyclic group, and the substituted divalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), wherein $Q_{11}$ to $Q_{17}$ and $Q_{21}$ to $Q_{27}$ may each be independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to one or more example embodiments, there is provided an organic light-emitting device including: a first electrode, a second electrode facing the first electrode; and an organic layer between the first electrode and the second electrode, the organic layer including an emission layer, wherein the organic layer includes the compound represented by Formula 1.

According to one or more example embodiments, there is provided a flat display apparatus including: a thin film transistor including a source electrode and a drain electrode; and the organic light-emitting device, wherein the first electrode of the organic light-emitting device is electrically coupled to the source electrode or the drain electrode of the thin film transistor.

BRIEF DESCRIPTION OF THE DRAWING

These and/or other aspects will become apparent and more readily appreciated from the following description of the example embodiments, taken in conjunction with the accompanying drawing, which illustrates a schematic view of an organic light-emitting device according to an example embodiment.

DETAILED DESCRIPTION

Reference will now be made in more detail to example embodiments, examples of which are illustrated in the accompanying drawing, wherein like reference numerals refer to like elements throughout. In this regard, the present example embodiments may have different forms and should not be construed as being limited to the descriptions set forth herein. Accordingly, the example embodiments are merely described below, by referring to the drawing, to explain aspects of the present description. As used herein, the term "and/or" includes any and all combinations of one or more of the associated listed items. Expressions such as "at least one of," "at least one selected from," and "one selected from," when preceding a list of elements, modify the entire list of elements and do not modify the individual elements of the list. Further, the use of "may" when describing embodiments of the present invention refers to "one or more embodiments of the present invention."

According to an aspect of the present inventive concept, there is provided a compound represented by Formula 1.

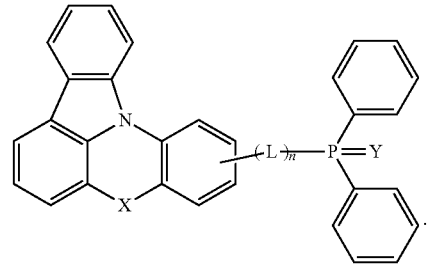

Formula 1

In Formula 1,

X may be selected from $NR_1$, S, O, and $CR_2R_3$, n may be an integer selected from 0 to 2, Y may be selected from O, S, and Se, $R_1$ to $R_3$ may each be independently selected from hydrogen, deuterium, a halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, L may be selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, and at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group, the substituted $C_6$-$C_{60}$ arylene group, the substituted $C_1$-$C_{60}$ heteroarylene group, the substituted divalent non-aromatic condensed polycyclic group, and the substituted divalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$);

wherein $Q_{11}$ to $Q_{17}$ and $Q_{21}$ to $Q_{27}$ may each be independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

An oxadiazole derivative (PBD) has recently been reported as an example of an electron transporting material. A triazole derivative (TAZ) and a phenantroline derivative (BCP) have also been reported as being capable of transporting electrons.

As an organic unimolecular material for forming an electron transport layer, an organic metal complex may be a good candidate, in terms of having electron stability and a relatively good electron transport speed. For example, it has been reported that Alq$_3$, having good stability and high electron affinity, is considered a suitable organic unimolecular material for forming the electron transport layer, and Alq$_3$ is still currently and often used as the basic material for forming the electron transport layer.

Additional examples of electron transporting materials in the related art include a flavon or germanium derivative and a silicon-containing cyclopentadiene derivative.

Organic unimolecular materials that include an imidazole group, an oxazole group, and/or a thiazole group have been reported as suitable electron injecting materials and electron transporting materials. However, before these organic unimolecular materials were reported as electron transport materials, metallic complex compounds of these organic unimolecular materials were sometimes used in the formation of a blue emission layer or a green emission layer.

TPBI is an example electron transporting material including an imidazole moiety, and its stricture includes three N-phenylbenzimidazolyl groups respectively formed at positions 1, 3, and 5 of a benzene ring. In regard to functional features of TPBI, it has capability of not only transporting electrons, but also blocking holes from diffusing into an emission layer. However, TPBI may have poor thermal stability, and thus may not be suitable for application in an actual device.

In addition, other electron transporting materials including an oxazole group and/or a thiazole group have been reported for application in an emission layer, but they resulted in unsatisfactory driving voltage, brightness, and lifespan characteristics of a device and thus failed to reach a practical use.

To address some of the concerns mentioned above, embodiments of the present inventive concept are directed toward a novel material having good electrical stability and electron transport capability, high glass transition temperature, and capability of preventing or reducing crystallization. The material according to embodiments of the present disclosure may be suitable for fluorescent and phosphorus organic light-emitting devices of all colors including red, green, blue, and white. Embodiments of the present inventive concept also provide an organic light-emitting device including the material, the organic light-emitting device having high efficiency, low driving voltage, high brightness, and long lifespan characteristics.

Substituents of the compound of Formula 1 will be described now in more detail.

According to an example embodiment, in Formula 1, $R_1$ to $R_3$ may each be independently a substituted or unsubstituted $C_1$-$C_{60}$ alkyl group, or a substituted or unsubstituted $C_6$-$C_{60}$ aryl group.

According to an example embodiment, in Formula 1, L may be a substituted or unsubstituted $C_6$-$C_{60}$ arylene group, or a substituted or unsubstituted $C_1$-$C_{60}$ heteroarylene group.

According to an example embodiment, in Formula 1, $R_1$ to $R_3$ may each be independently selected from a phenyl group, a biphenyl group, a terphenyl group, and a methyl group.

According to an example embodiment, in Formula 1, L may be selected from groups represented by Formulae 2a to 2e:

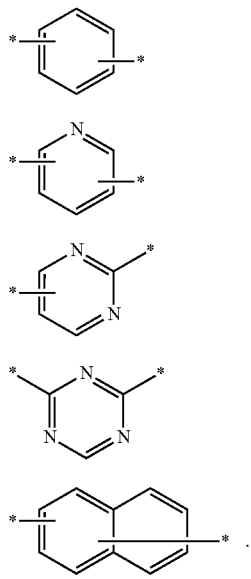

2a

2b

2c

2d

2e

In Formulae 2a to 2e, * indicates a binding site.

According to an example embodiment, the compound of Formula 1 may be represented by Formula 2:

Formula 2

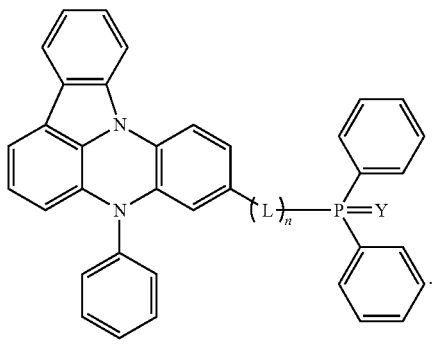

According to an example embodiment, the compound of Formula 1 may be represented by Formula 3:

Formula 3

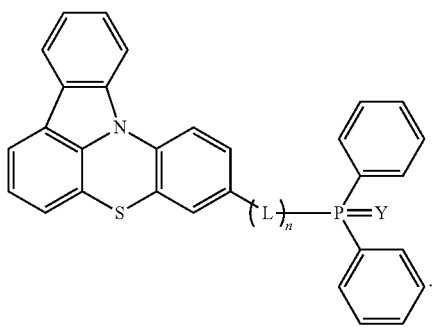

According to an example embodiment, the compound of Formula 1 may be represented by Formula 4:

Formula 4

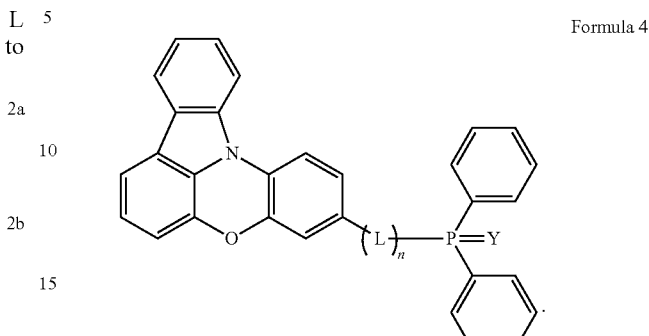

According to an example embodiment, the compound of Formula 1 may be represented by Formula 5:

Formula 5

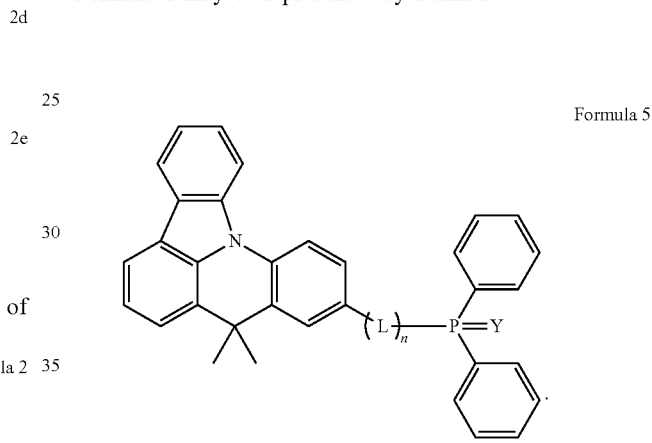

In Formulae 2 to 5, descriptions of substituents may be as provided above.

According to an example embodiment, the compound of Formula 1 may be selected from Compounds A1 to A16 and A18 to A65:

A1

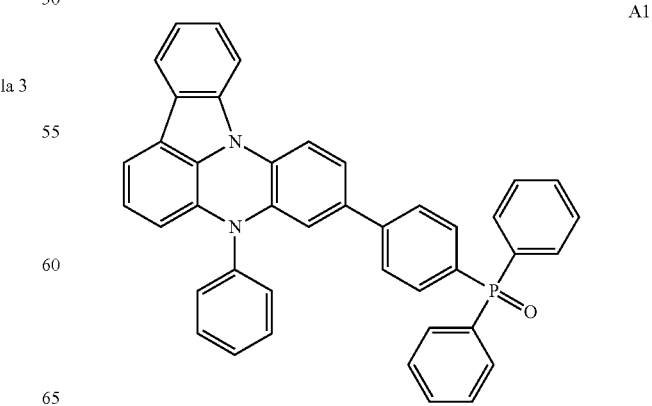

A2
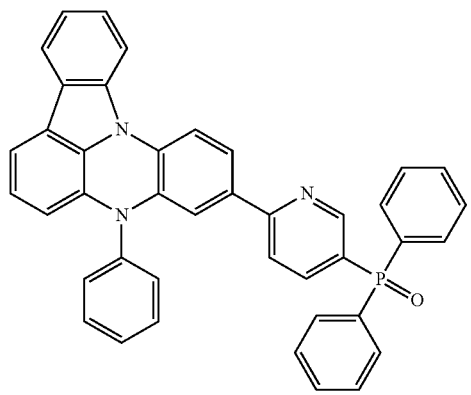
A3
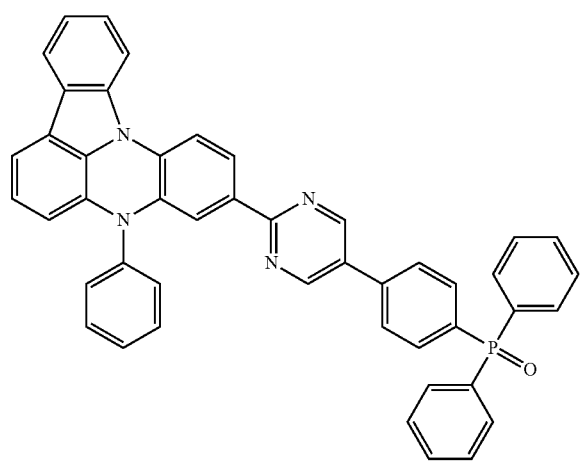
A4
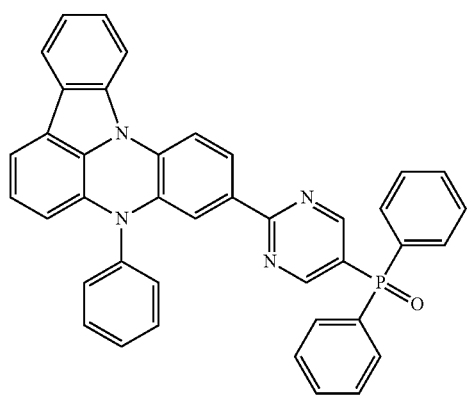
A5
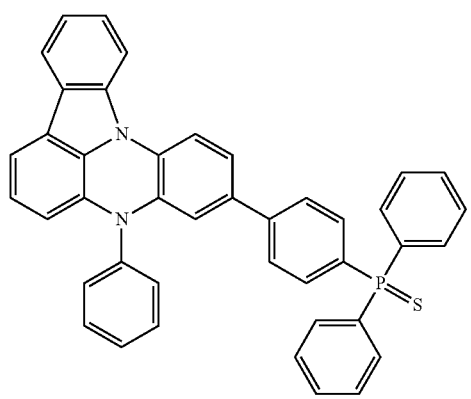
A6
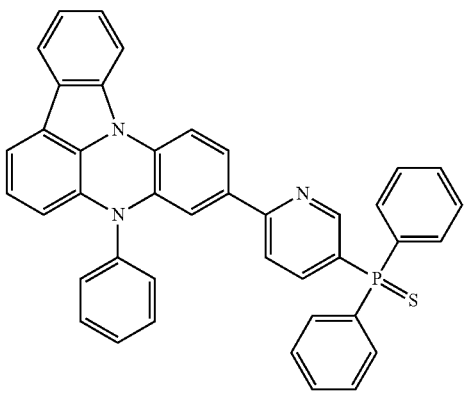
A7
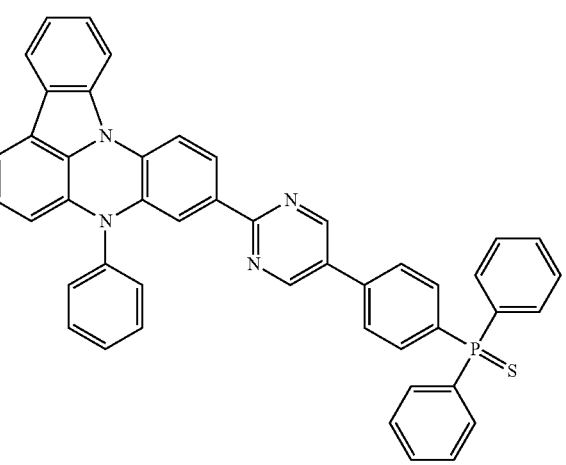
A8
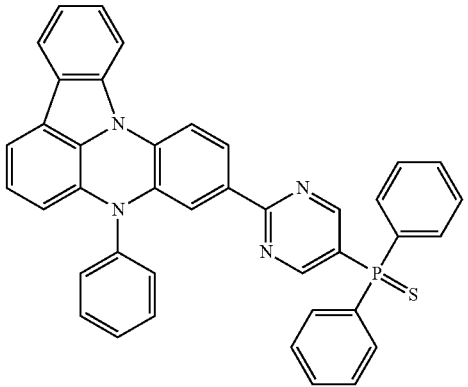

A9
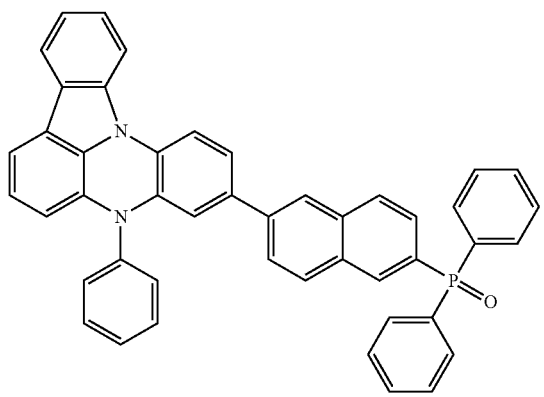
A13
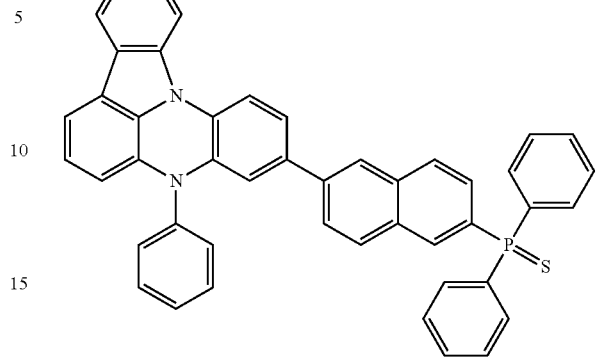
A10
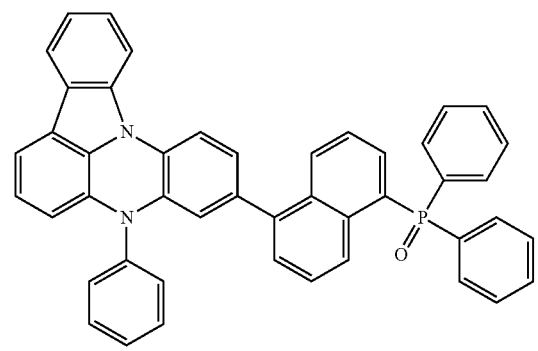
A14
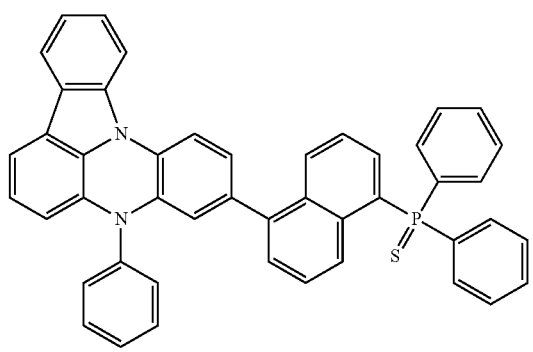
A11
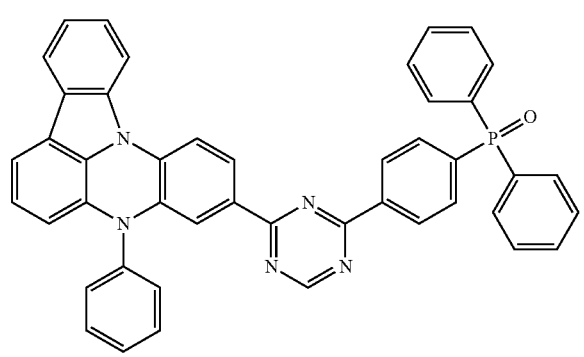
A15
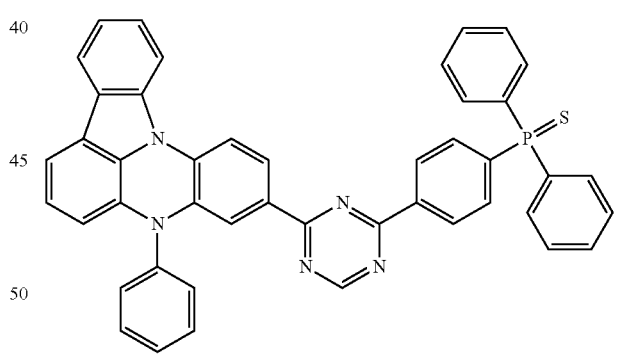
A12
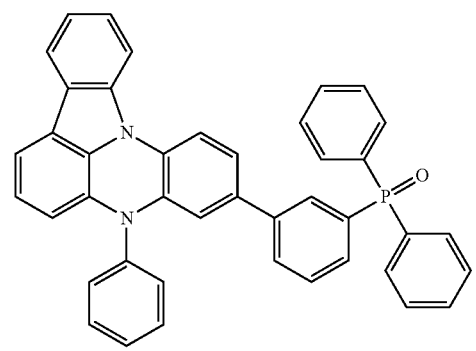
A16
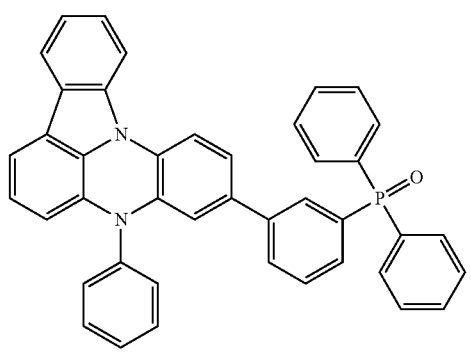

A18
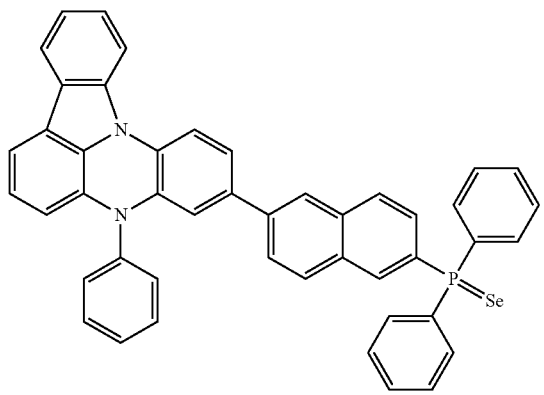
A19
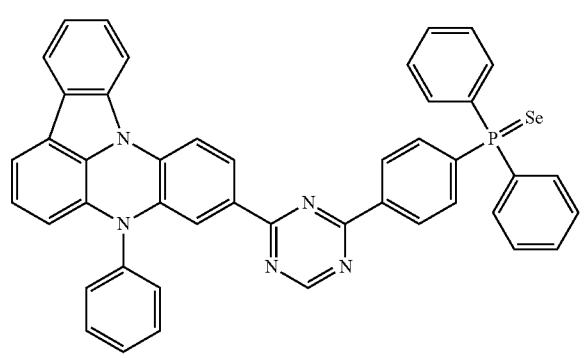
A20
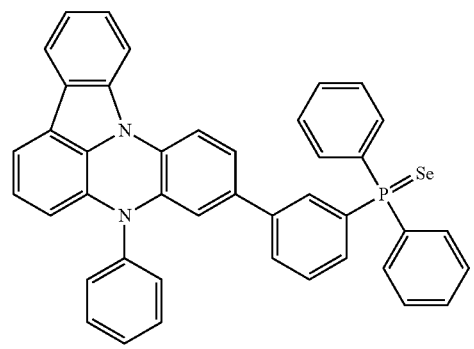
A21
A22
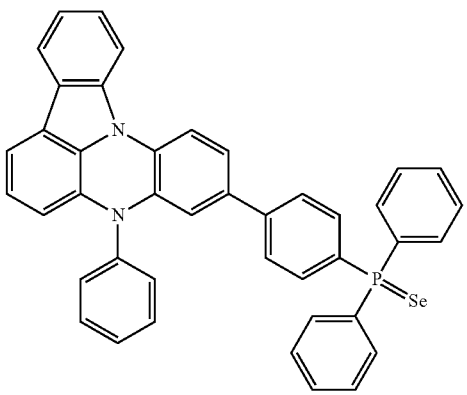
A23
A24
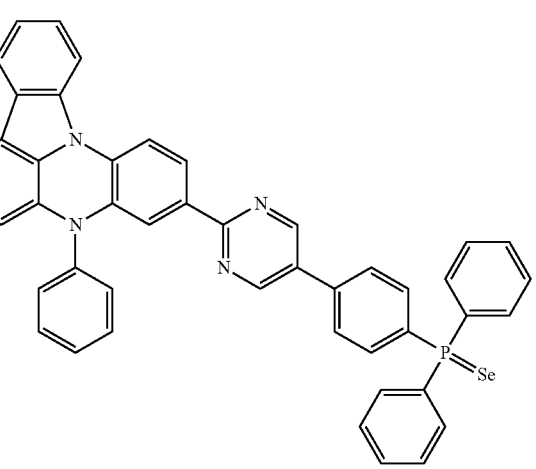
A25
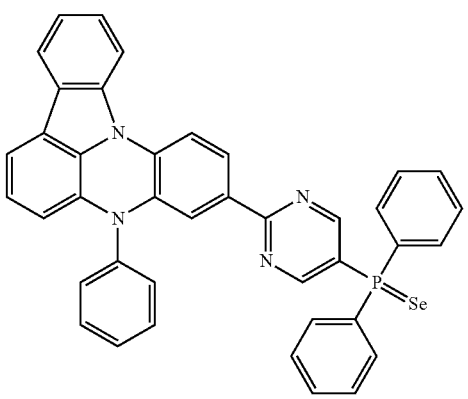

A26
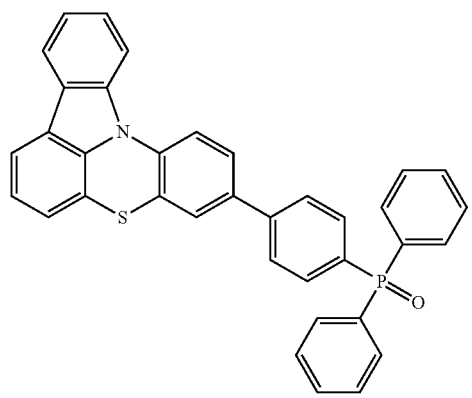
A27
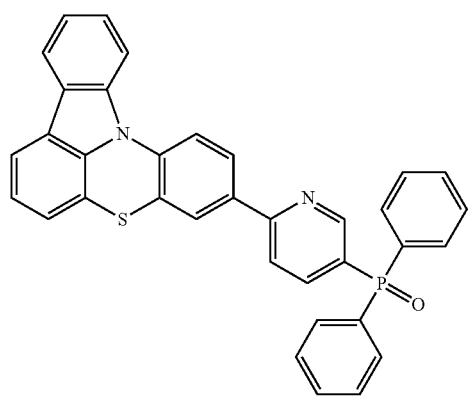
A28
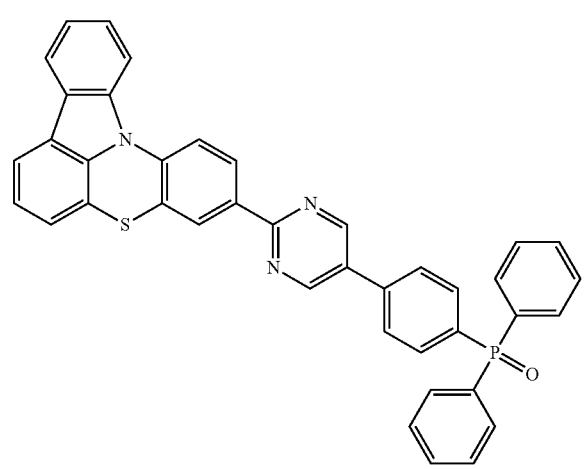
A29
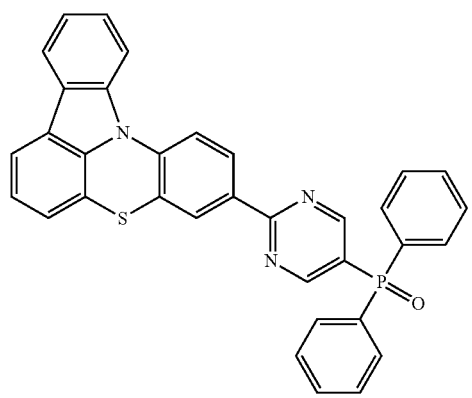
A30
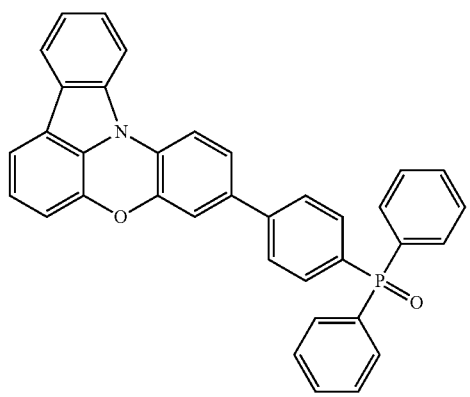
A31
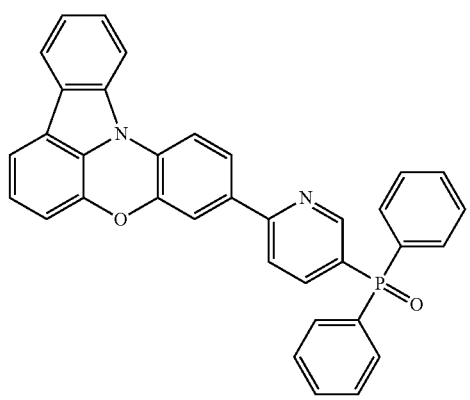
A32
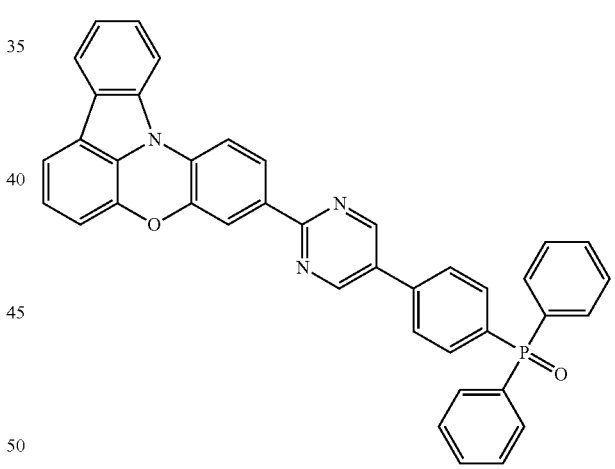
A33
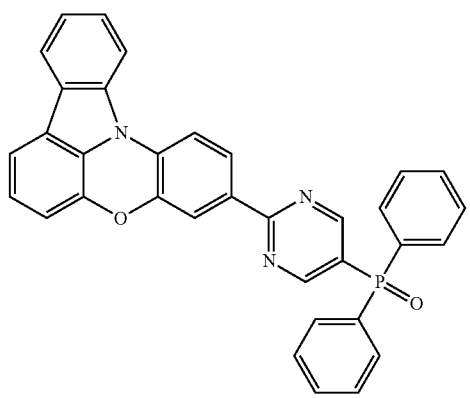

A34 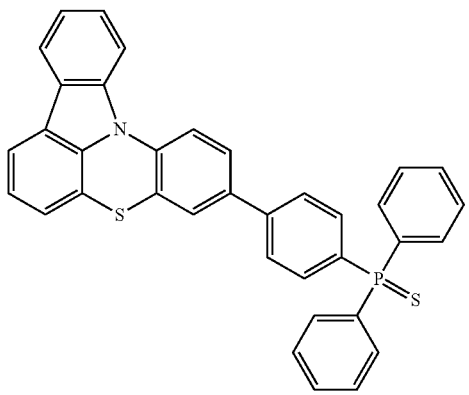
A35 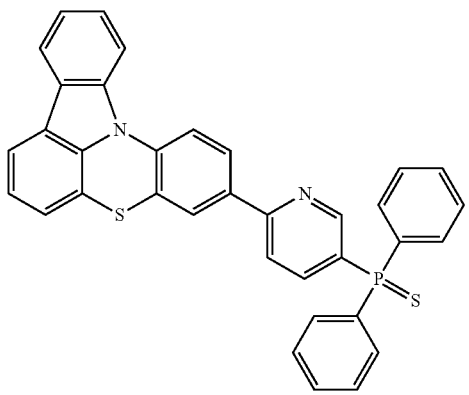
A36 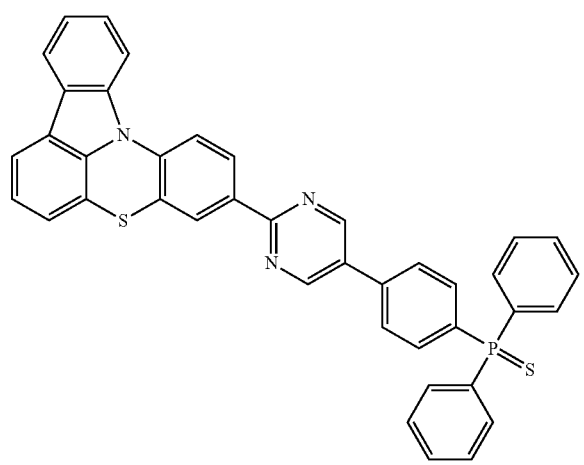
A37 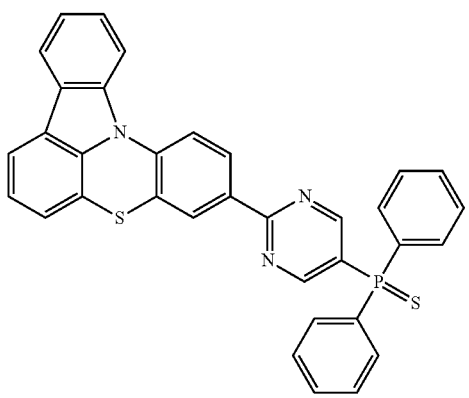
A38 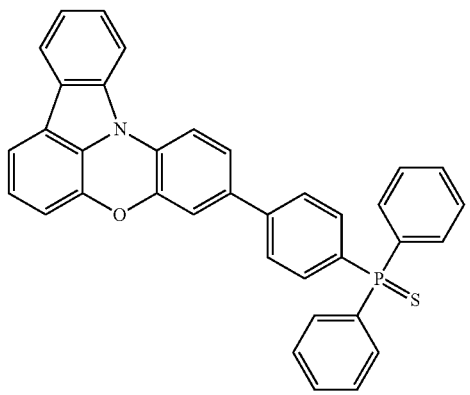
A39 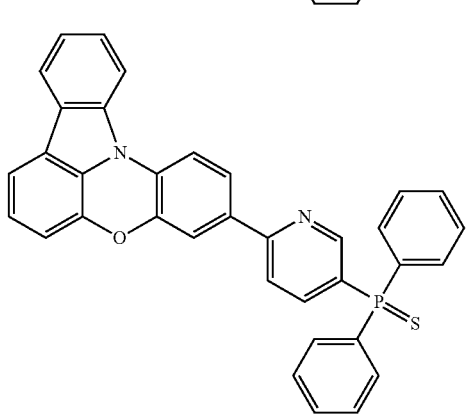
A40 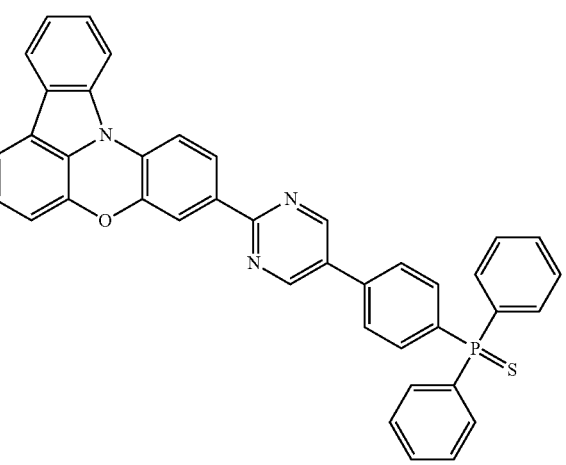
A41 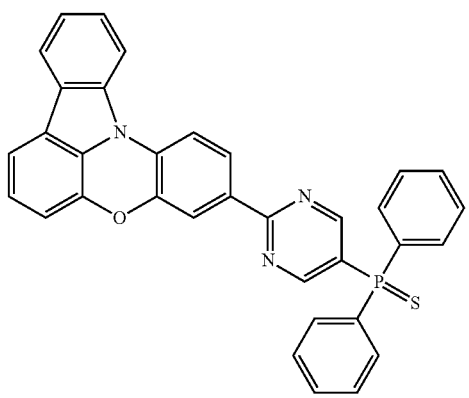

-continued
A42
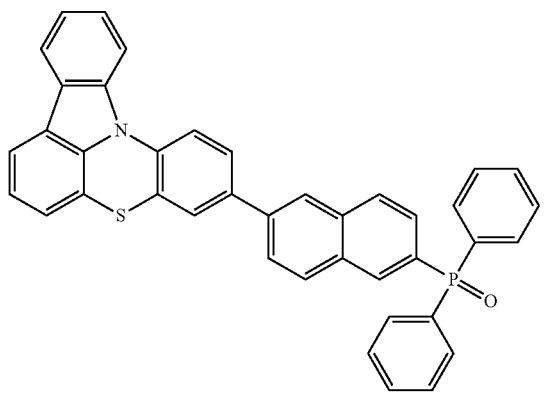
A46
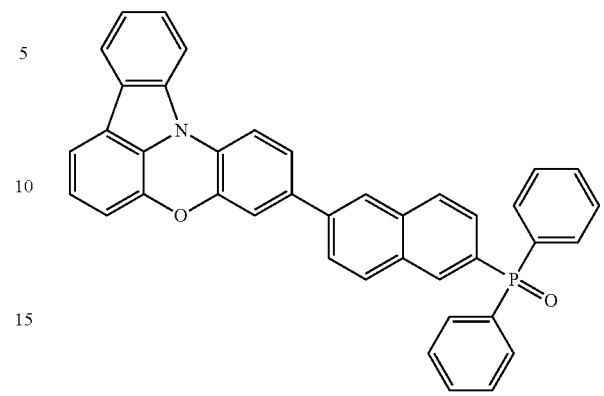
A43
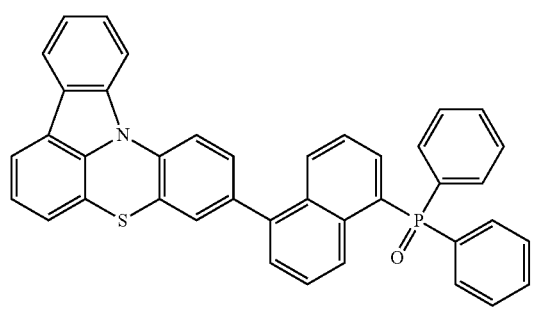
A47
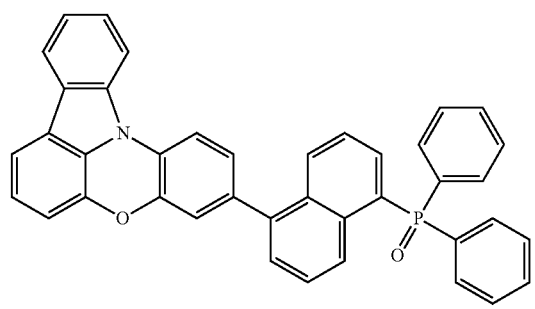
A44
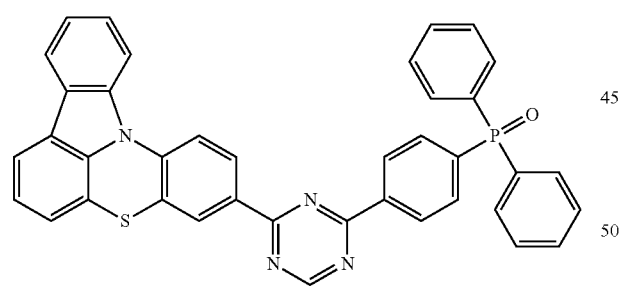
A48
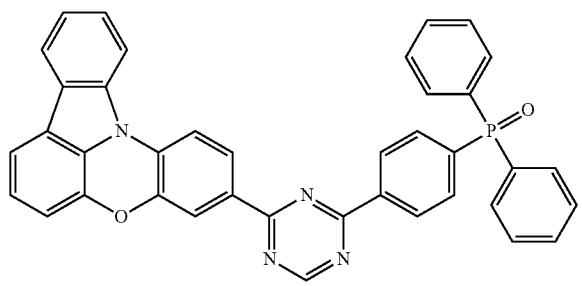
A45
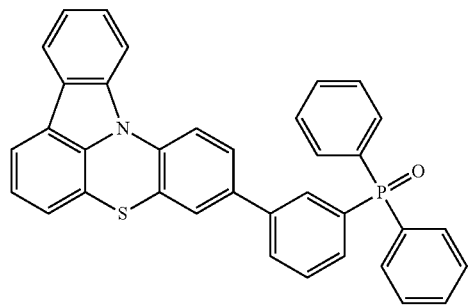
A49
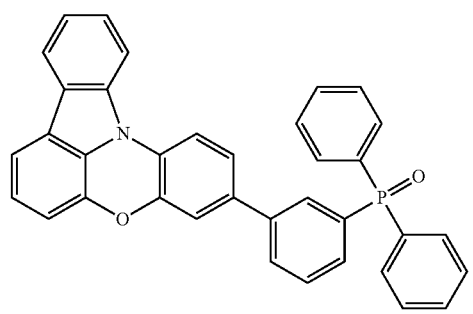

A50
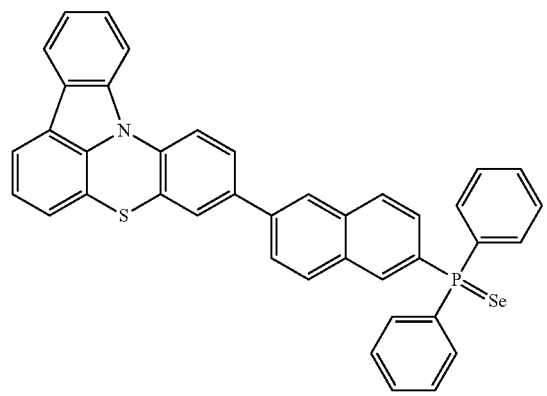
A51
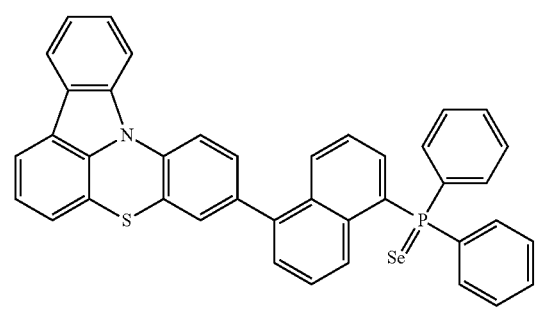
A52
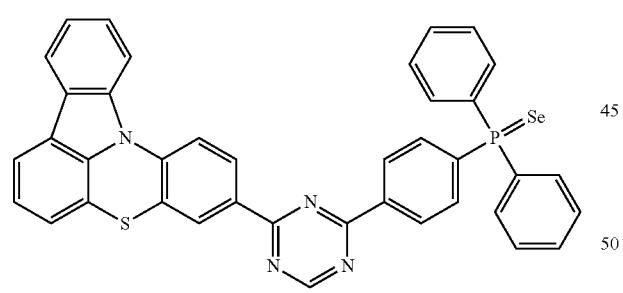
A53
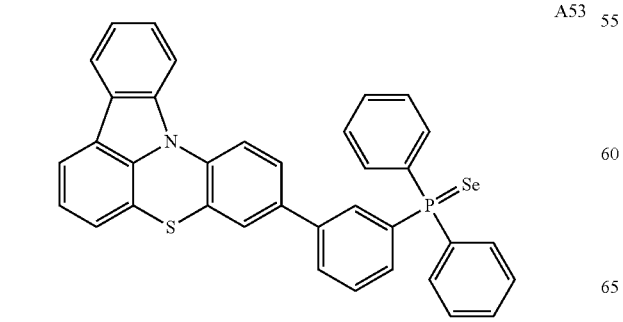
A54
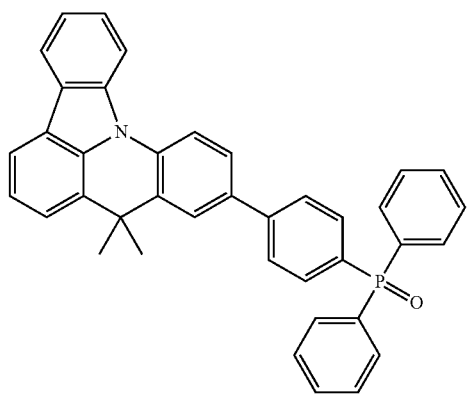
A55
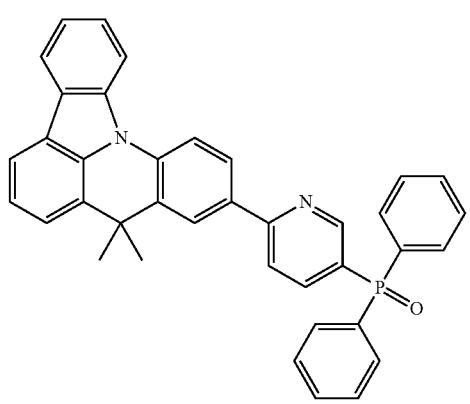
A56
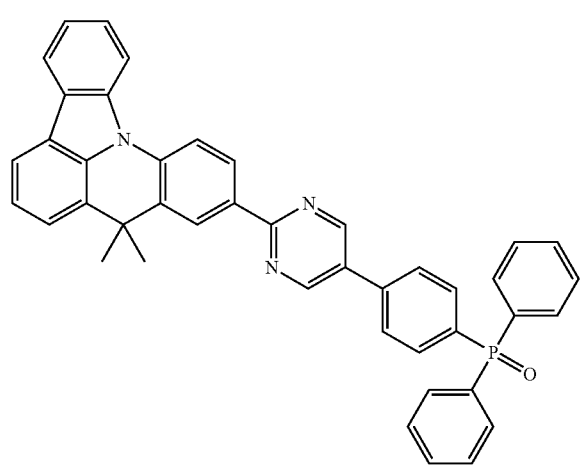
A57
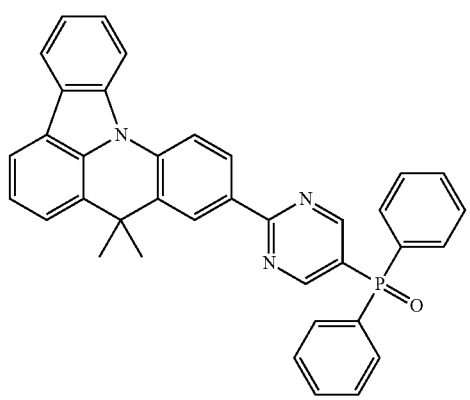

A58
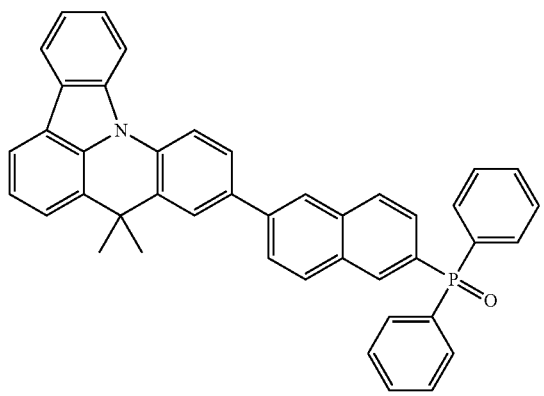
A59
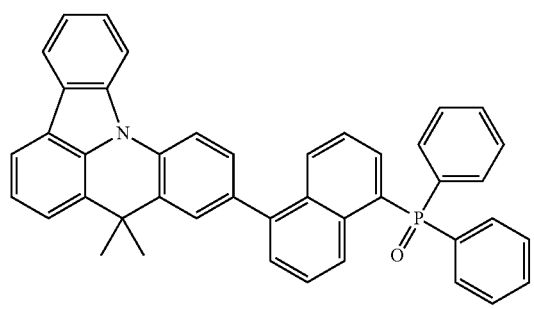
A60
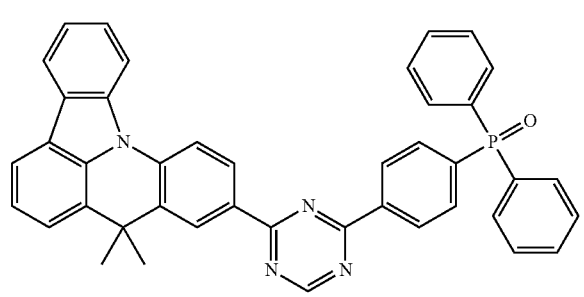
A61
A62
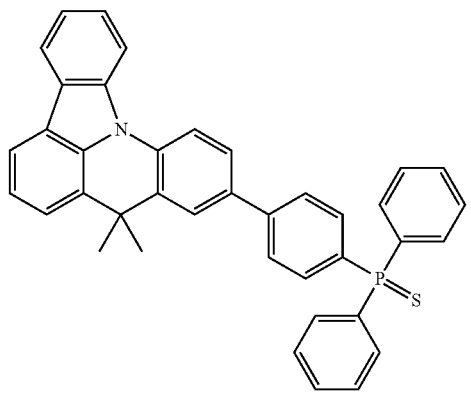
A63
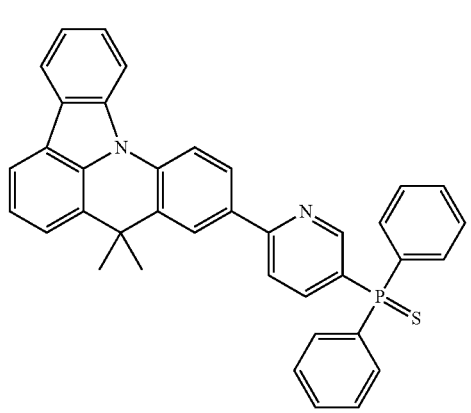
A64
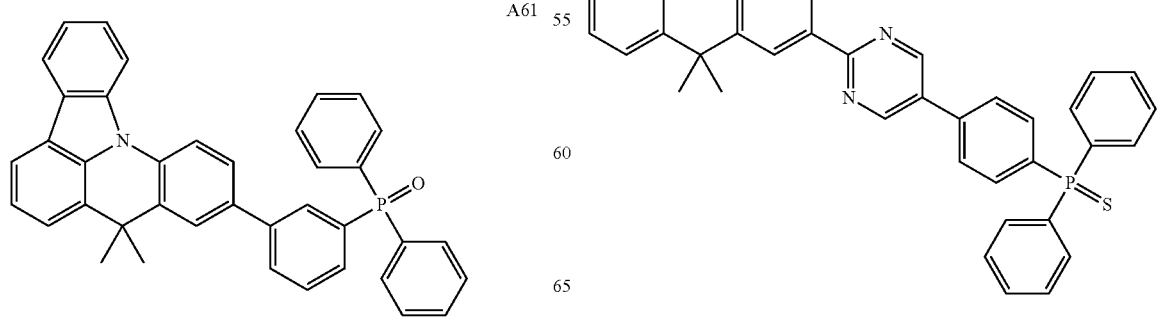

-continued

A65

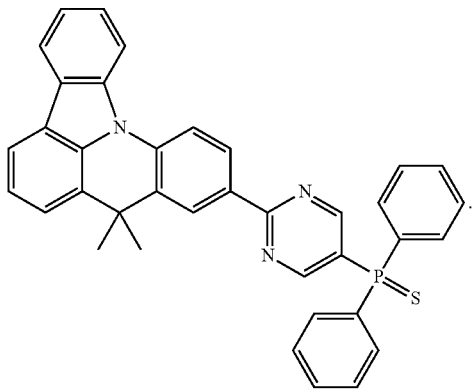

The term "organic layer" as used herein may refer to a single layer and/or a plurality of layers disposed (e.g., positioned) between a first electrode and a second electrode of an organic light-emitting device. A material included in the "organic layer" is not limited to an organic material.

The drawing is a schematic view of a structure of an organic light-emitting device 10 according to an example embodiment. The organic light-emitting device 10 includes a first electrode 110, an organic layer 150, and a second electrode 190.

Hereinafter, a structure of the organic light-emitting device 10 according to an example embodiment and a method of manufacturing the organic light-emitting device 10 according to an example embodiment will be described in connection with the drawing.

In the drawing, a substrate may be additionally disposed (e.g., positioned) under the first electrode 110 or on the second electrode 190. The substrate may be a glass substrate or a transparent plastic substrate, each with excellent mechanical strength, thermal stability, transparency, surface smoothness, ease of handling, and/or water-resistance.

The first electrode 110 may be formed by, for example, depositing or sputtering a material for forming the first electrode 110 on the substrate. When the first electrode 110 is an anode, the material for forming the first electrode 110 may be selected from materials having a high work function to facilitate hole injection. The first electrode 110 may be a reflective electrode, a semi-transparent electrode, or a transparent electrode. The material for forming the first electrode 110 may be a transparent and highly conductive material, and non-limiting examples of such material include indium tin oxide (ITO), indium zinc oxide (IZO), tin oxide ($SnO_2$), and zinc oxide (ZnO). When the first electrode 110 is a semi-transparent electrode or a reflective electrode, at least one selected from magnesium (Mg), aluminum (Al), aluminum-lithium (Al—Li), calcium (Ca), magnesium-indium (Mg—In), and magnesium-silver (Mg—Ag) may be utilized as a material for forming the first electrode 110.

The first electrode 110 may have a single-layered structure or a multi-layered structure including a plurality of layers. For example, the first electrode 110 may have a three-layered structured of ITO/Ag/ITO, but the structure of the first electrode 110 is not limited thereto.

The organic layer 150 may be disposed (e.g., positioned) on the first electrode 110, and the organic layer 150 may include an emission layer (EML).

The organic layer 150 may further include a hole transport region disposed between the first electrode 110 and the EML and an electron transport region disposed between the EML and the second electrode 190.

The hole transport region may include at least one selected from a hole injection layer (HIL), a hole transport layer (HTL), a buffer layer, and an electron blocking layer (EBL); and the electron transport region may include at least one selected from a hole blocking layer (HBL), an electron transport layer (ETL), and an electron injection layer (EIL), but the hole transport region and the electron transport region are not limited thereto.

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a multi-layered structure such as a structure of HIL/HTL, a structure of HIL/HTL/buffer layer, a structure of HIL/buffer layer, a structure of HTL/buffer layer, or a structure of HIL/HTL/EBL. Layers of each structure are sequentially stacked from the first electrode 110 in this stated order, but the hole transport region is not limited thereto.

When the hole transport region includes an HIL, the HIL may be formed on the first electrode 110 by utilizing various suitable methods, such as vacuum deposition, spin coating, casting, a Langmuir-Blodgett (LB) method, ink-jet printing, laser-printing, and/or a laser-induced thermal imaging (LITI) method.

When an HIL is formed by vacuum deposition, the vacuum deposition may be performed, for example, at a deposition temperature of about 100° C. to about 500° C., at a vacuum degree of about $10^{-8}$ torr to about $10^{-3}$ torr, and a deposition rate of about 0.01 Å/sec to about 100 Å/sec, depending upon a composition of a compound for forming the HIL to be deposited and a structure of the HIL to be formed.

When an HIL is formed by spin coating, the coating may be performed, for example, at a coating speed of about 2,000 rpm to about 5,000 rpm, and at a temperature of about 80° C. to about 200° C., depending upon a composition of a compound for forming the HIL to be deposited and a structure of the HIL to be formed.

When the hole transport region includes an HTL, the HTL may be formed on the first electrode 110 or the HIL by utilizing various suitable methods, such as vacuum deposition, spin coating, casting, an LB method, an ink-jet printing, a laser-printing, and/or an LITI method. When the HTL is formed by vacuum deposition and/or spin coating, the deposition and coating conditions for the HTL may be determined by referring to the deposition and coating conditions for the HIL.

The hole transport region may include at least one selected from m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine)

(TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline/poly(4-styrenesulfonate) (PANI/PSS):
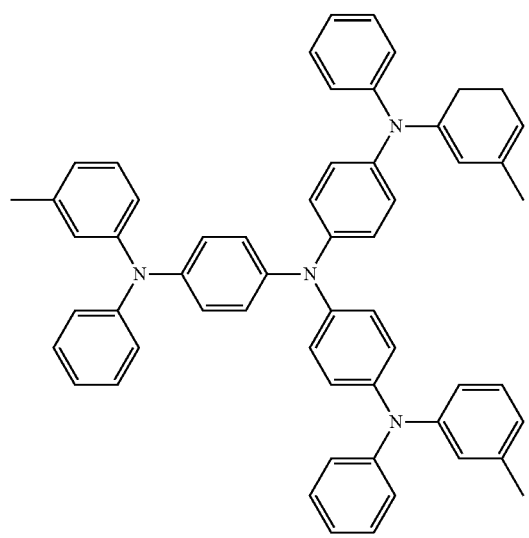
m-MTDATA
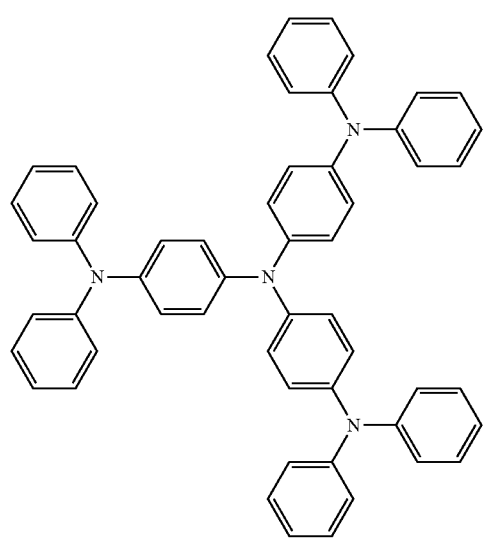
TDATA
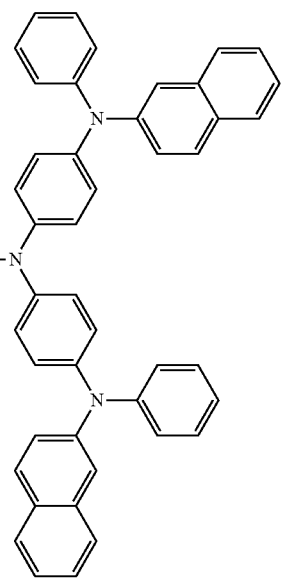
2-TNATA
NPB
β-NPB
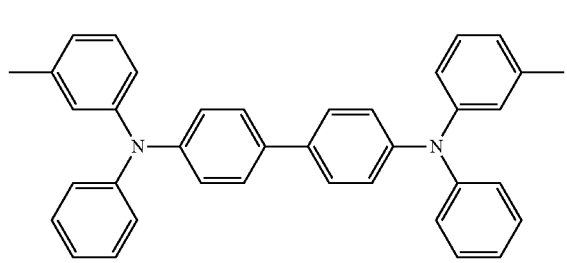
TPD

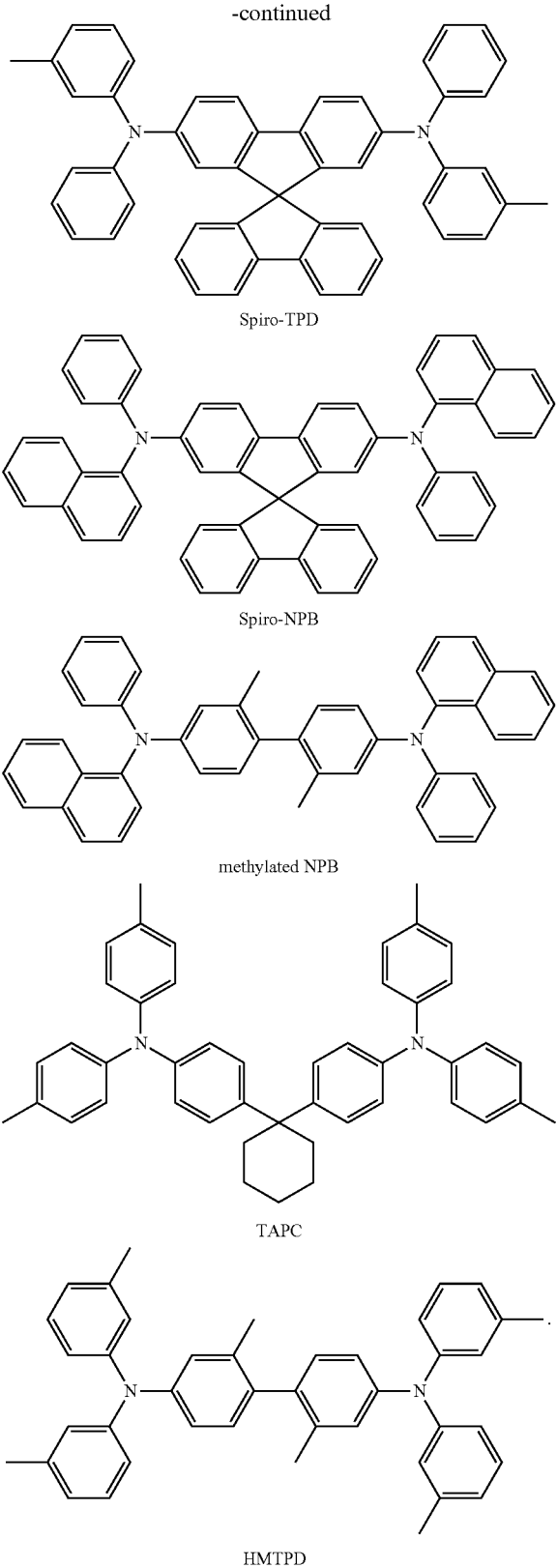

Spiro-TPD

Spiro-NPB methylated NPB

TAPC

HMTPD

A thickness of the hole transport region may be in a range of about 100 Å to about 10,000 Å, for example, about 100 Å to about 1,000 Å. When the hole transport region includes both an HIL and an HTL, a thickness of the HIL may be in a range of about 100 Å to about 10,000 Å, for example, about 100 Å to about 1,000 Å; and a thickness of the HTL may be in a range of about 50 Å to about 2,000 Å, for example about 100 Å to about 1,500 Å. In one example embodiment, when the thicknesses of the hole transport region, the HIL, and the HTL are within any of these ranges, satisfactory or suitable hole transporting characteristics can be obtained without a substantial increase in driving voltage.

The hole transport region may further include, in addition to the materials described above, a charge-generation material for the improvement of conductive properties. The charge-generation material may be homogeneously or inhomogeneously dispersed in the hole transport region.

The charge-generation material may be, for example, a p-dopant. The p-dopant may be a quinone derivative, a metal oxide, or a cyano group-containing compound, but the p-dopant is not limited thereto. Non-limiting examples of the p-dopant include quinone derivatives (such as tetracyano-quinonedimethane (TCNQ) and/or 2,3,5,6-tetrafluoro-tetracyano-1,4-benzoquinonedimethane (F4-TCNQ)); metal oxides (such as tungsten oxide and/or molybdenum oxide); and Compound HT-D1.

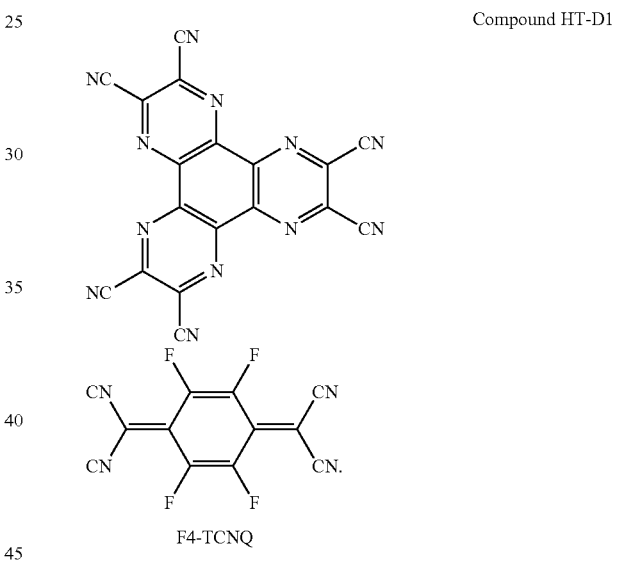

Compound HT-D1

F4-TCNQ

The hole transport region may further include, in addition to the HIL and the HTL, an EBL and/or a buffer layer. Since the buffer layer may compensate for an optical resonance distance according to a wavelength of light emitted from the EML, light-emission efficiency of the formed organic light-emitting device may be improved. For use as a material included in the buffer layer, any of the materials that are included in the hole transport region may be utilized. The EBL may prevent or reduce the injection of electrons from the electron transport region.

The EML may be formed on the first electrode 110 or on the hole transport region by utilizing various suitable methods, such as vacuum deposition, spin coating, casting, an LB method, an ink-jet printing, a laser-printing, and/or an LITI method. When the EML is formed by vacuum deposition and/or spin coating, the deposition and coating conditions for the emission layer may be determined by referring to the deposition and coating conditions for the HIL.

When the organic light-emitting device 10 is a full color organic light-emitting device, the EML may be patterned into a red EML, a green EML, and/or a blue EML, according to individual sub pixels, respectively. The EML may have various modifications in the structure, and for example, may have a structure of a red EML, a green EML, and a blue EML, where the layers are sequentially stacked in the stated order, or a structure in which a red light-emitting material, a green light-emitting material, and a blue light-emitting material are mixed without distinction between layers, and accordingly the EML may emit white light.

The EML may include a host and a dopant.

The host may include, for example, at least one selected from TPBi, TBADN, ADN (herein also referred to as "DNA"), CBP, CDBP, TCP, and the compound of Formula 1 according to an example embodiment:

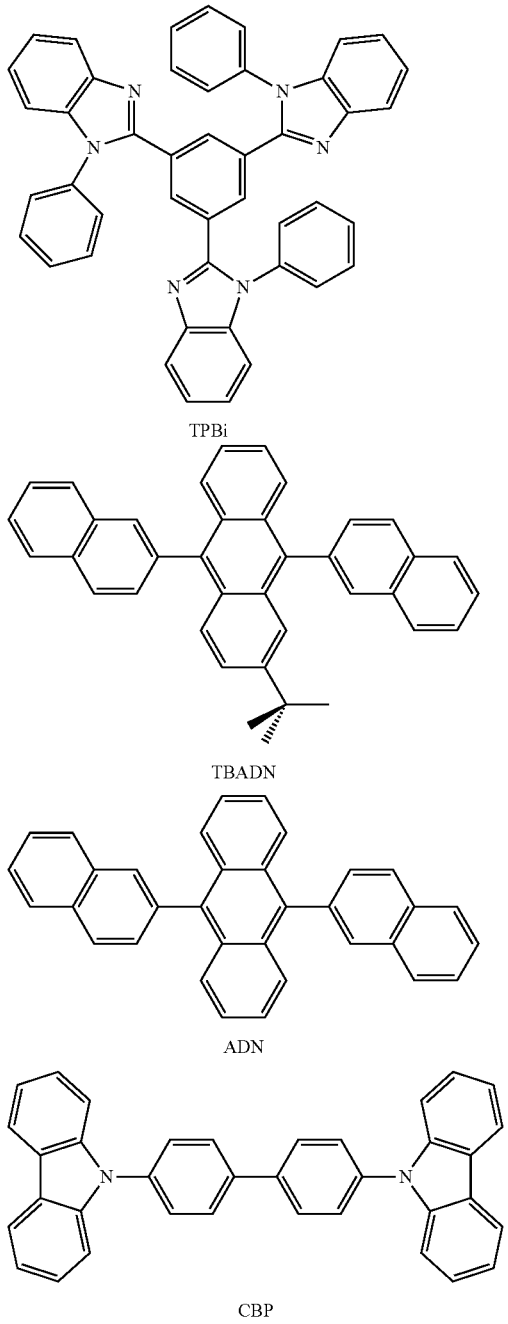

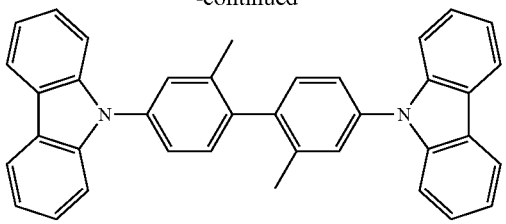

CDBP

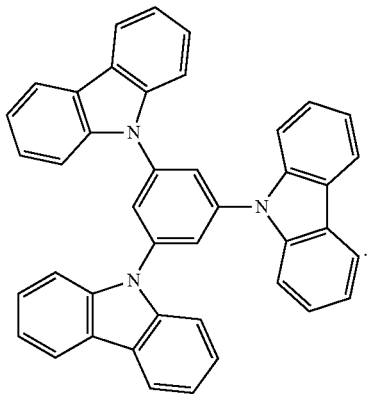

TCP

In some embodiments, the host may include a compound represented by Formula 301:

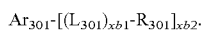   Formula 301

In Formula 301, $Ar_{301}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (wherein $Q_{301}$ to $Q_{303}$ may each be independently selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group), $L_{301}$ may be selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group, $R_{301}$ may be selected from:

a $C_1$-$C_{20}$ alkyl group and a $C_1$-$C_{20}$ alkoxy group;

a $C_1$-$C_{30}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a biphenyl group, a terphenyl group, a naphthyl group a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xb1 may be selected from 0, 1, 2, and 3, and xb2 may be selected from 1, 2, 3, and 4.

For example, in Formula 301, $L_{301}$ may be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group a fluorenyl group, a spiro-fluorenyl group, a benzofluorenyl group, a dibenzofluorenyl group, a phenanthrenyl group, an anthracenyl group, a pyrenyl group, and a chrysenyl group, $R_{301}$ may be selected from:

a $C_1$-$C_{20}$ alkyl group and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a biphenyl group, a terphenyl group, a naphthyl group a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group a fluorenyl group, a spiro-fluorenyl group, a benzofluorenyl group, a dibenzofluorenyl group, a phenanthrenyl group, an anthracenyl group, a pyrenyl group, and a chrysenyl group, but the embodiments are not limited thereto.

For example, the host may include a compound represented by Formula 301A:

Formula 301A
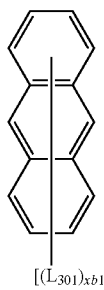
[(L$_{301}$)$_{xb1}$—R$_{301}$]$_{xb2}$.
Descriptions of substituents of Formula 301A are as provided above.
The compound of Formula 301 may include at least one selected from Compounds H1 to H42:
H1
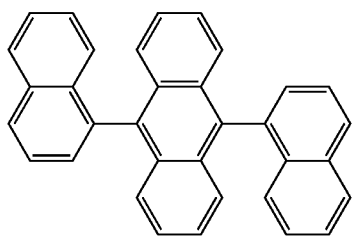
H2
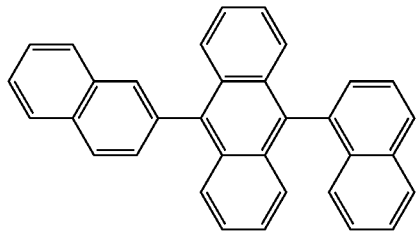
H3
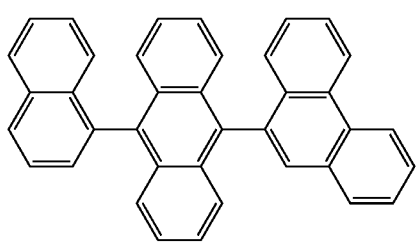
H4
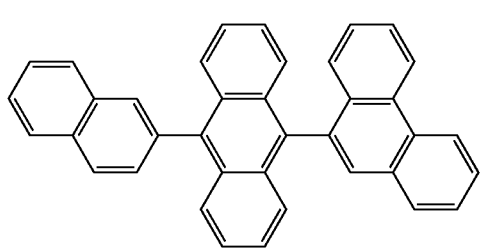
H5
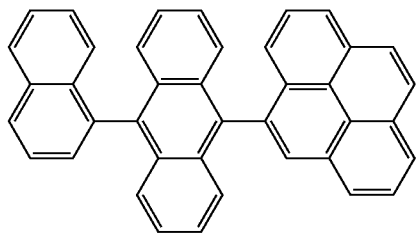
H6
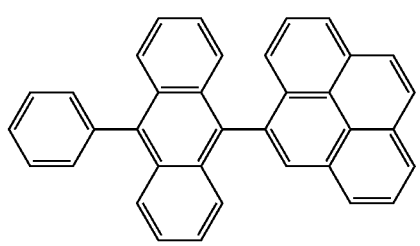
H7
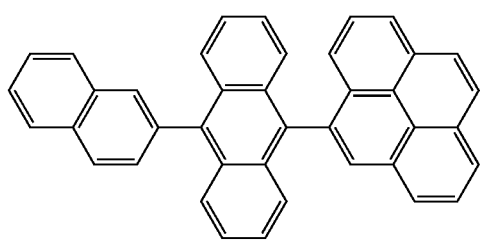
H8
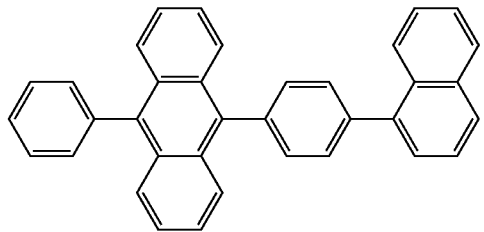
H9
H10

H11
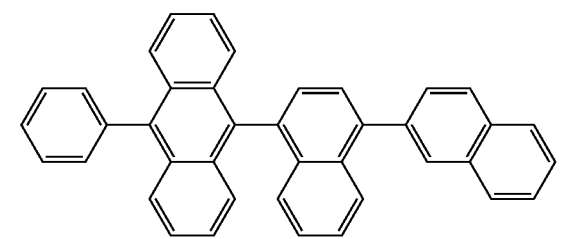
H12
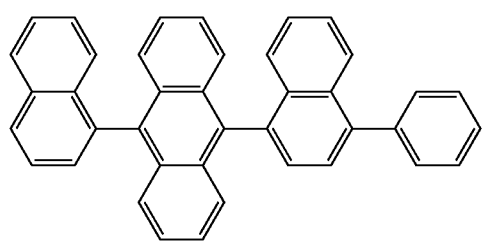
H13
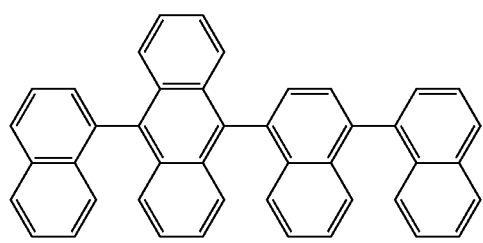
H14
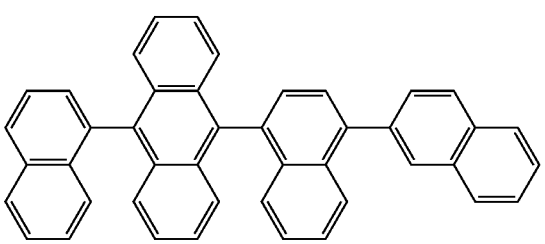
H15
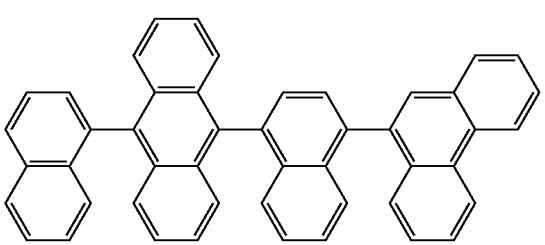
H16
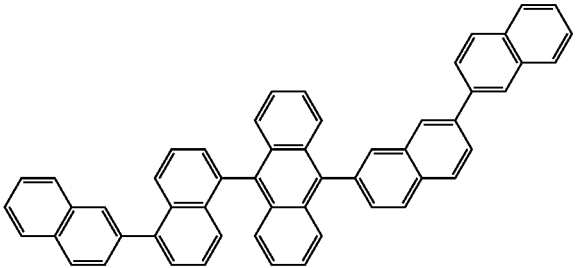
H17
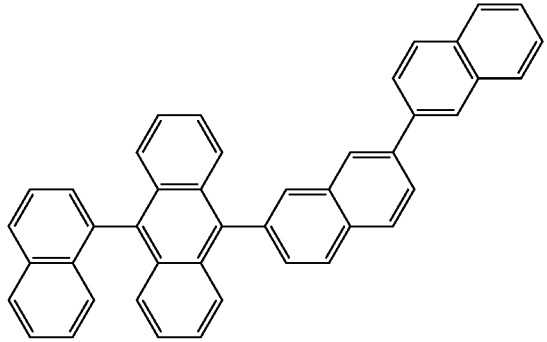
H18
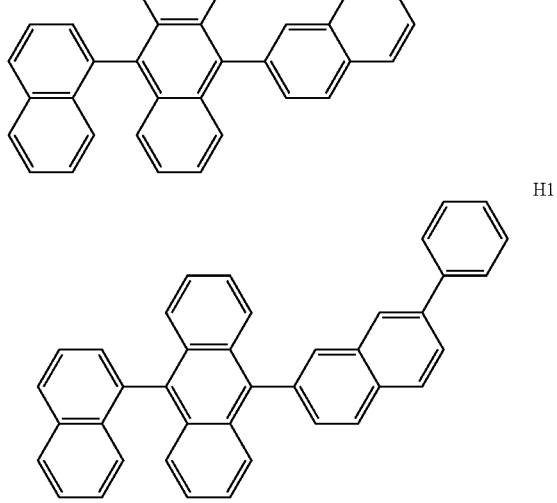
H19
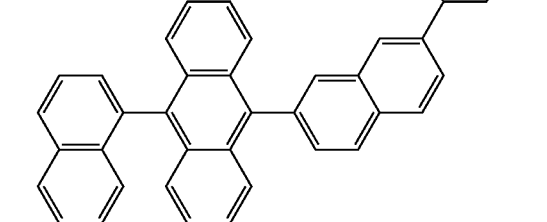
H20
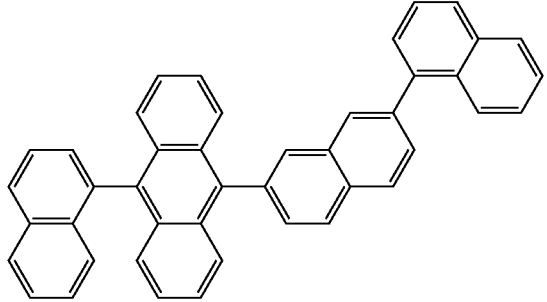
H21
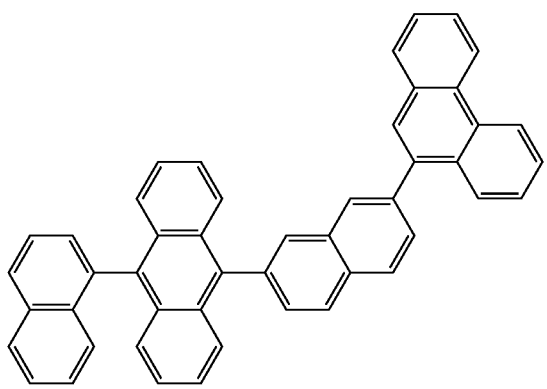

H22
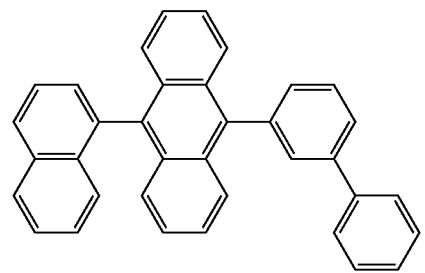
H23
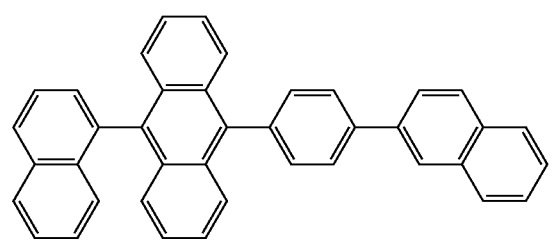
H24
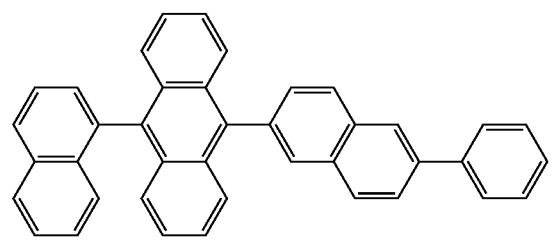
H25
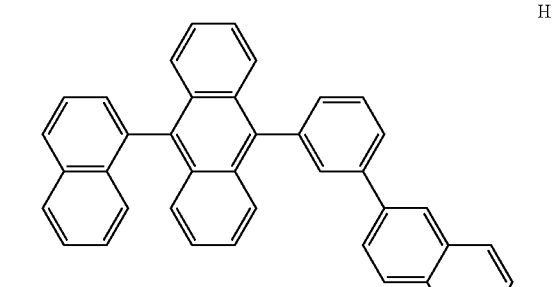
H26
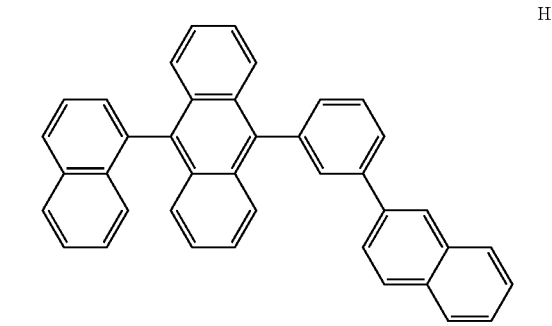
H27
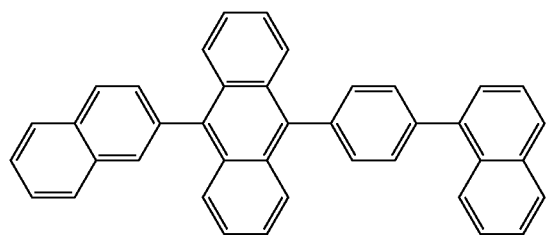
H28
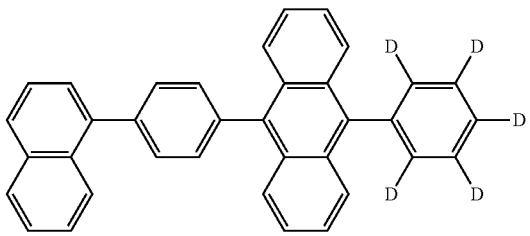
H29
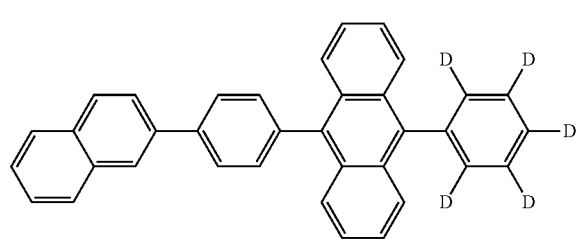
H30
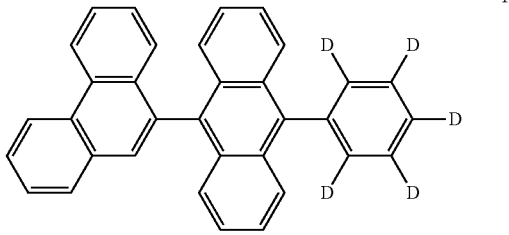
H31
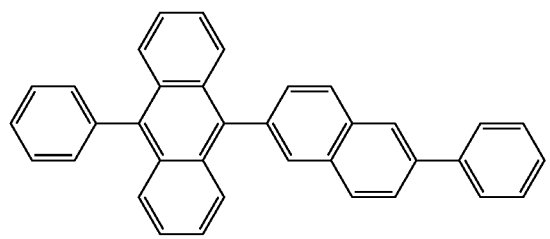
H32
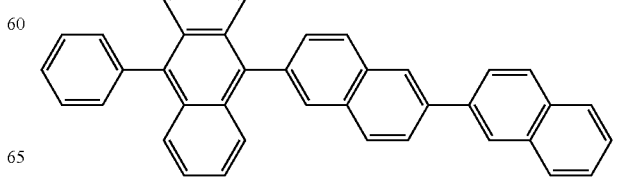

-continued
H33
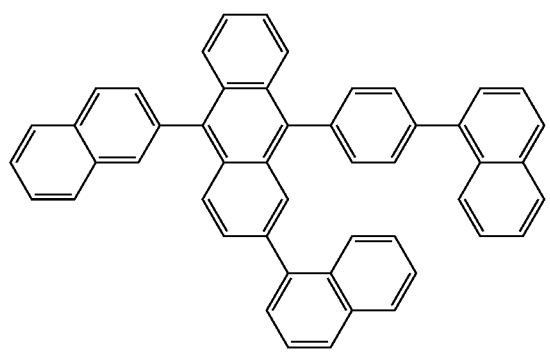
H34
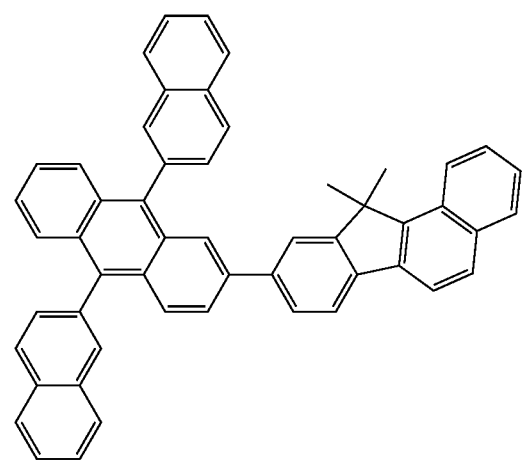
H35
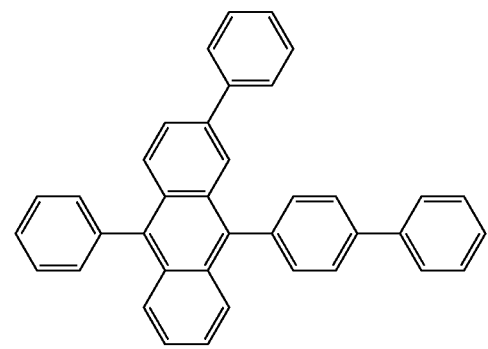
-continued
H36
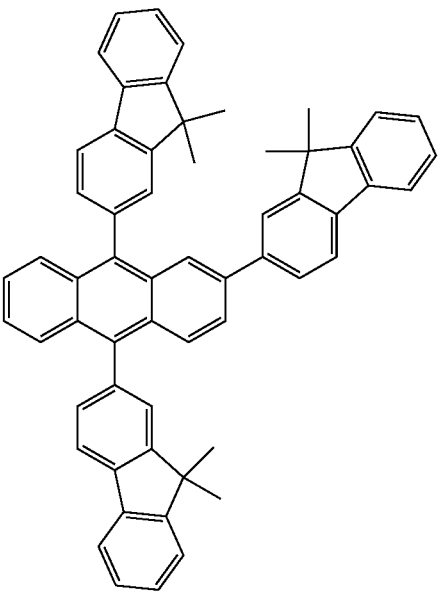
H37
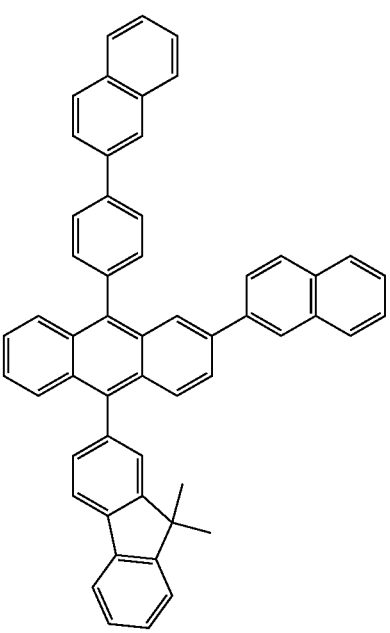
H38
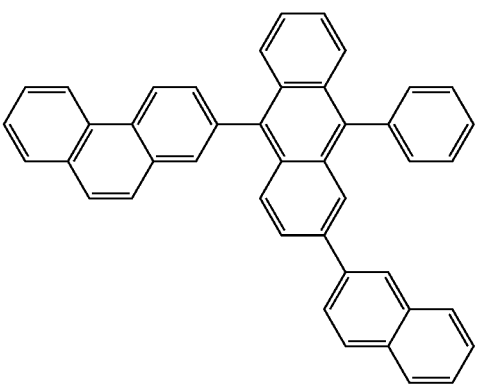

H39
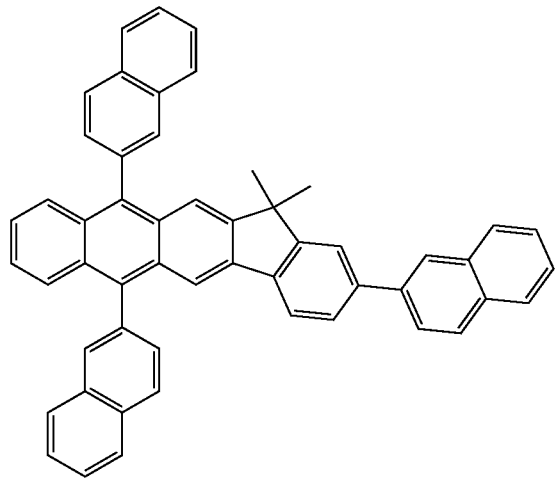
H40
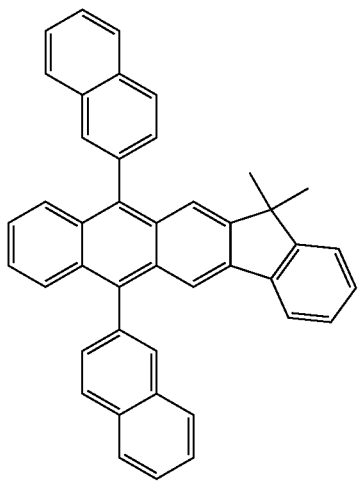
H41
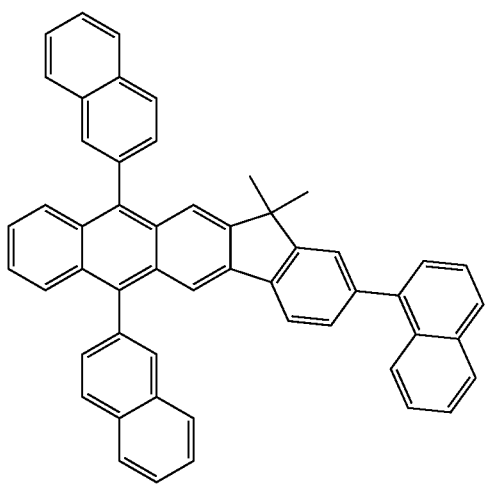
H42
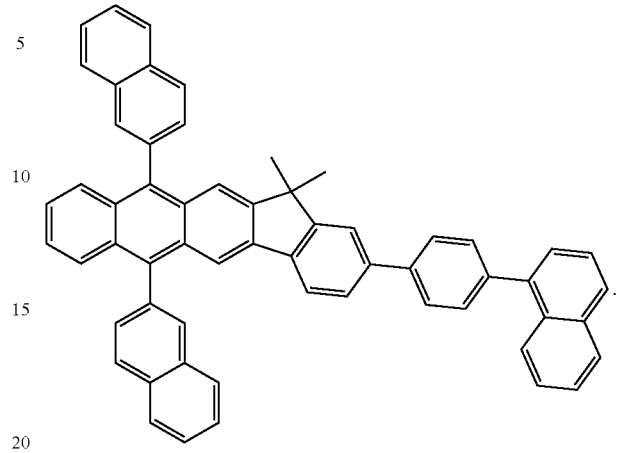
In some embodiments, the host may include at least one selected from Compounds H43 to H49, but the host is not limited thereto:
H43
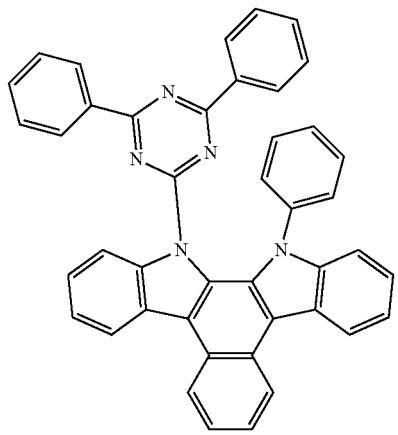
H44
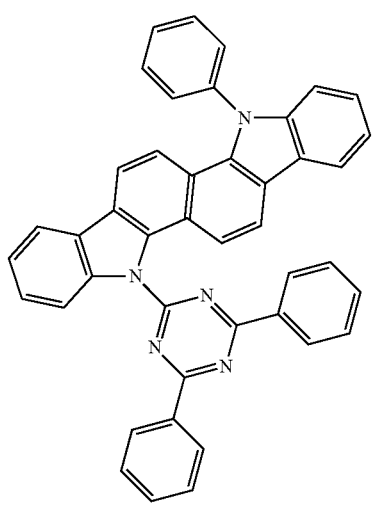

-continued

H45
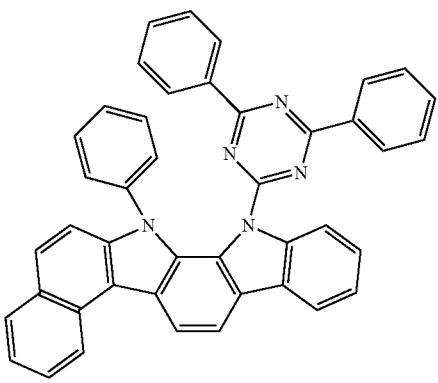

H46
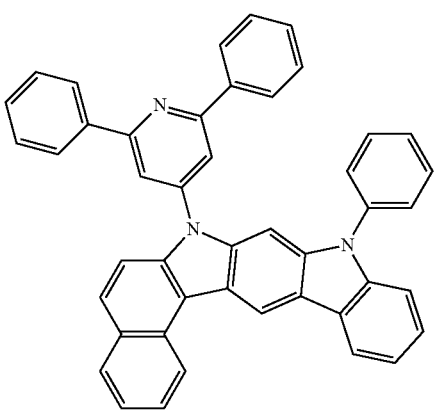

H47
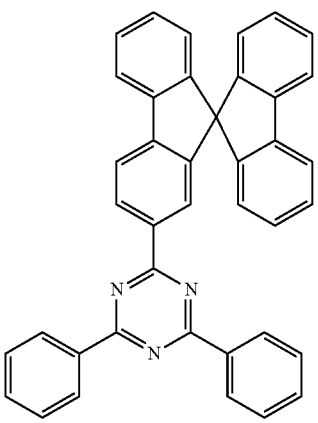

H48
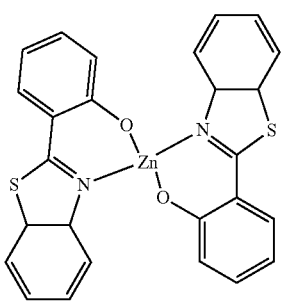

-continued

H49
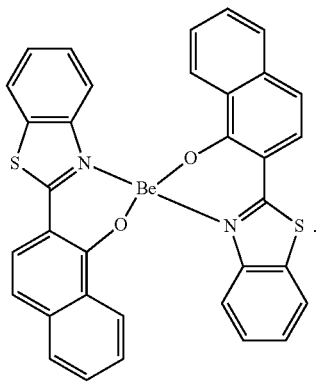

The dopant may include at least one selected from a fluorescent dopant and a phosphorescent dopant.

The phosphorescent dopant may include an organic metal complex represented by Formula 401:

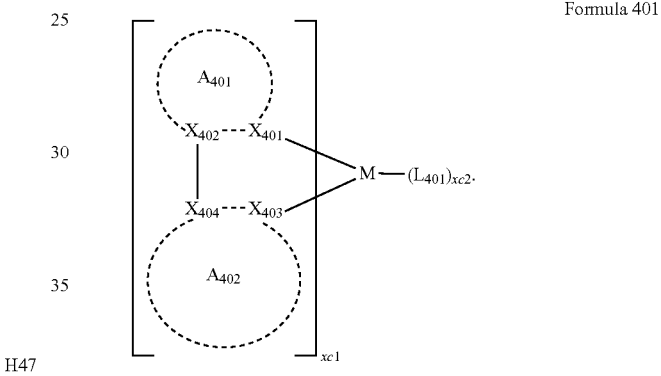

Formula 401

In Formula 401,

M may be selected from iridium (Ir), platinum (Pt), osmium (Os), titanium (Ti), zirconium (Zr), hafnium (Hf), europium (Eu), terbium (Tb), and thulium (Tm), $X_{401}$ to $X_{404}$ may each be independently nitrogen or carbon, rings $A_{401}$ and $A_{402}$ may each be independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene, at least one substituent of the substituted benzene, the substituted naphthalene, the substituted fluorene, the substituted spiro-fluorene, the substituted indene, the substituted pyrrole, the substituted thiophene, the substituted furan, the substituted imidazole, the substituted pyrazole, the substituted thiazole, the substituted isothiazole, the substituted oxazole, the substituted isoxazole, the substituted pyridine, the substituted pyrazine, the substituted pyrimidine, the substituted pyridazine, the substituted quinoline, the substituted isoquinoline, the substituted benzoquinoline, the substituted quinoxaline, the substituted quinazoline, the substituted carbazole, the substituted benzoimidazole, the substituted benzofuran, the substituted benzothiophene, the substituted isobenzothiophene, the substituted benzoxazole, the substituted isobenzoxazole, the substituted triazole, the substituted oxadiazole, the substituted triazine, the substituted dibenzofuran, and the substituted dibenzothiophene may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and B($Q_{426}$)($Q_{427}$), wherein $Q_{401}$ to $Q_{407}$, $Q_{411}$ to $Q_{417}$, and $Q_{421}$ to $Q_{427}$ may each be independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, $L_{401}$ may be an organic ligand, xc1 may be 1, 2, or 3, and xc2 may be 0, 1, 2, or 3.

In Formula 401, $L_{401}$ may be a monovalent organic ligand, a divalent organic ligand, or a trivalent organic ligand. For example, in Formula 401, $L_{401}$ may be selected from a halogen ligand (e.g., Cl and/or F), a diketone ligand (e.g., acetylacetonate, 1,3-diphenyl-1,3-propanedionate, 2,2,6,6-tetramethyl-3,5-heptanedionate, and/or hexafluoroacetonate), a carboxylic acid ligand (e.g., picolinate, dimethyl-3-pyrazolecarboxylate, and/or benzoate), a carbon monoxide ligand, an isonitrile ligand, a cyano group ligand, and a phosphorus ligand (e.g., phosphine and/or phosphite), but the embodiments are not limited thereto.

When $A_{401}$ in Formula 401 has two or more substituents, two or more substituents of $A_{401}$ may be bonded to each other to form a saturated ring or an unsaturated ring.

When $A_{402}$ in Formula 401 has two or more substituents, two or more substituents of $A_{402}$ may be bonded to each other to form a saturated ring or an unsaturated ring.

When xc1 in Formula 401 is 2 or more, a plurality of ligands

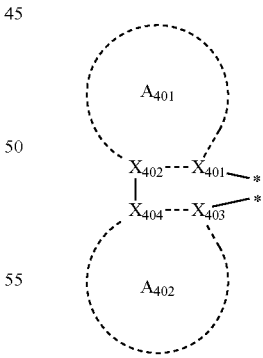

in Formula 401 may be identical to or different from each other. When xc1 in Formula 401 is 2 or more, $A_{401}$ and $A_{402}$ of one ligand may each independently be respectively bonded to $A_{401}$ and $A_{402}$ of other neighboring ligands, directly (e.g., via a bond such as a single bond) or via a linking group (e.g., a $C_1$-$C_5$ alkylene group, —N(R')— (where R' may be a $C_1$-$C_{10}$ alkyl group or a $C_6$-$C_{20}$ aryl group), and/or —C(=O)—).

The phosphorescent dopant may include at least one selected from Compounds PD1 to PD74, but the embodiments are not limited thereto:
PD1
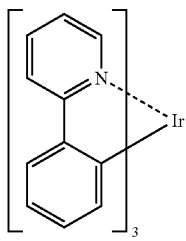
PD2
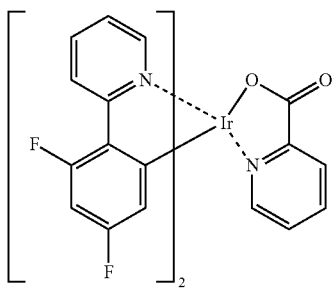
PD3
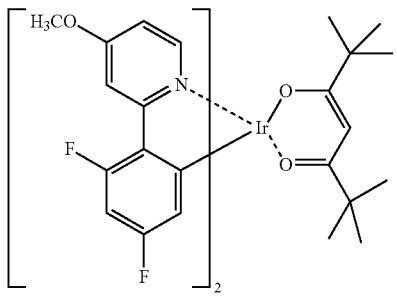
PD4
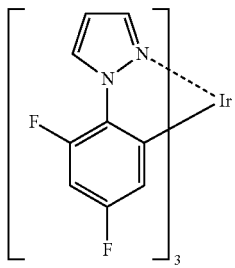
PD5
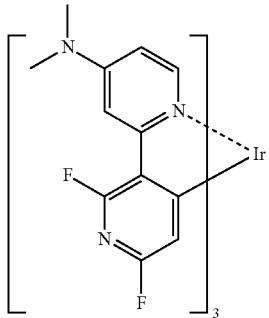
PD6
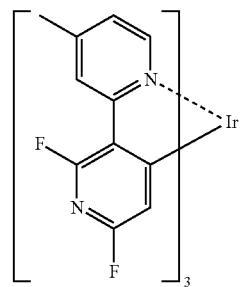
PD7
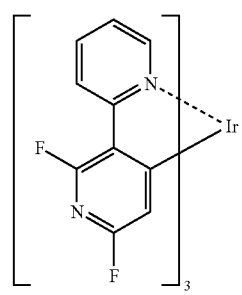
PD8
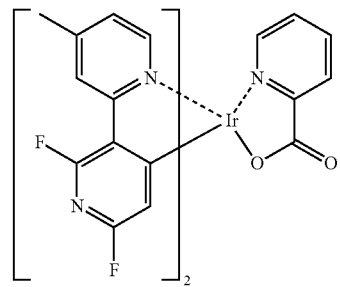
PD9
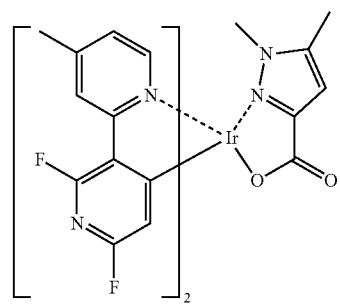
PD10
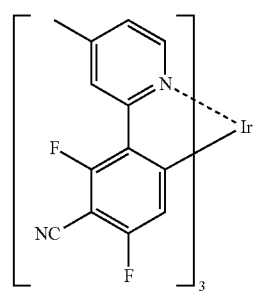

PD11 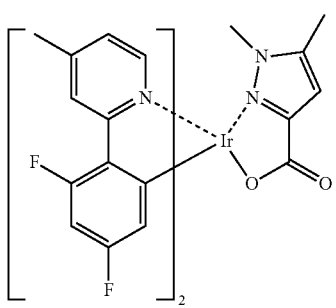
PD12 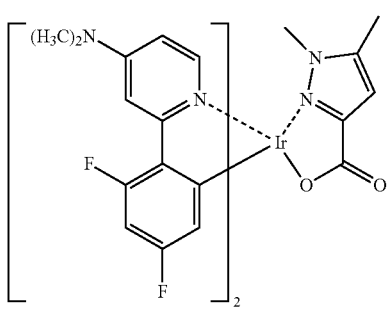
PD13 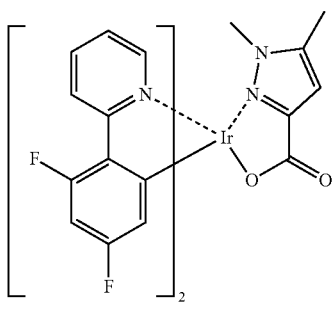
PD14 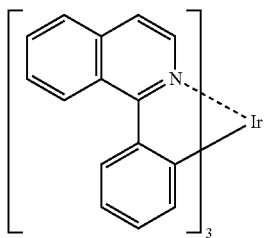
PD15 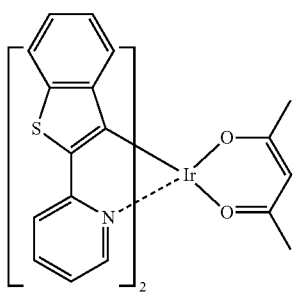
PD16 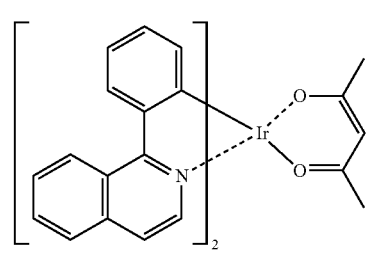
PD17 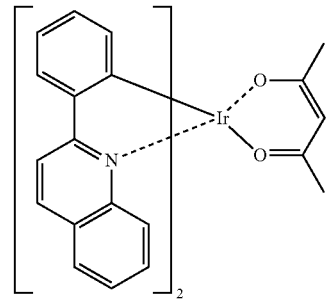
PD18 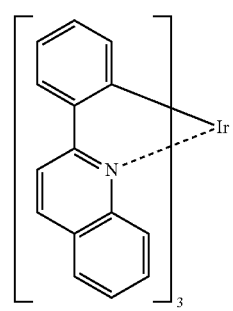
PD19 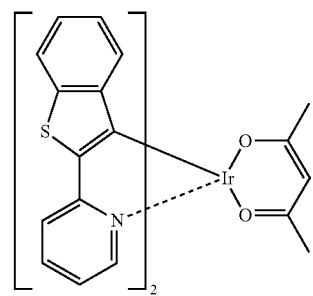
PD20 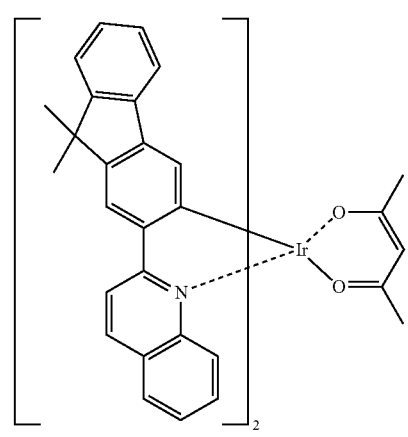

PD21
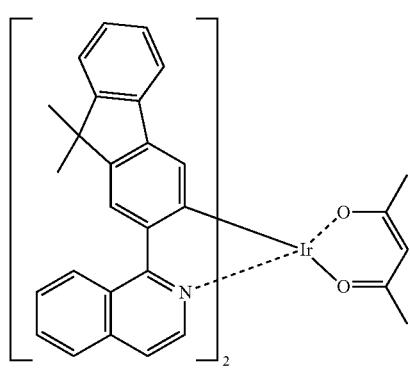
PD22
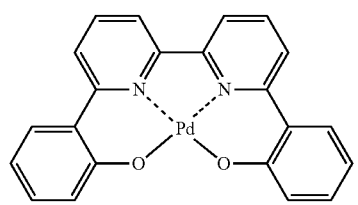
PD23
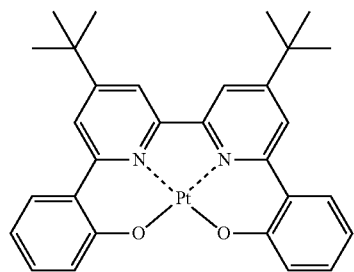
PD24
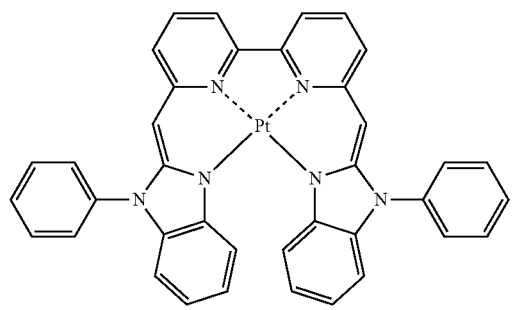
PD25
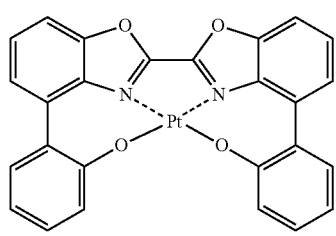
PD26
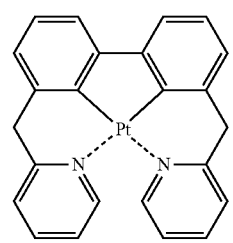
PD27
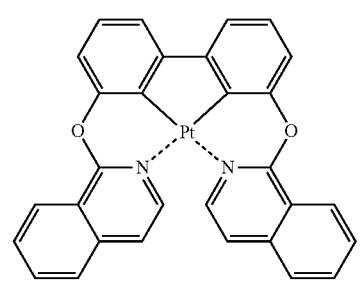
PD28
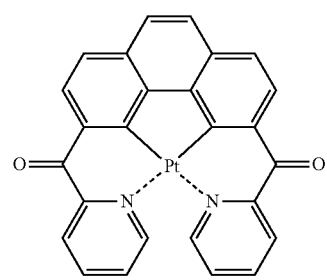
PD29
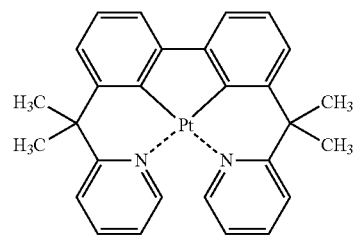
PD30
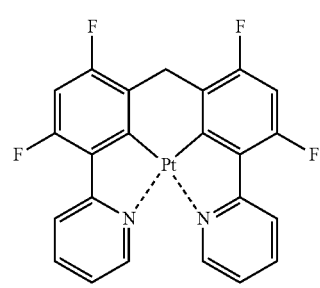

PD31 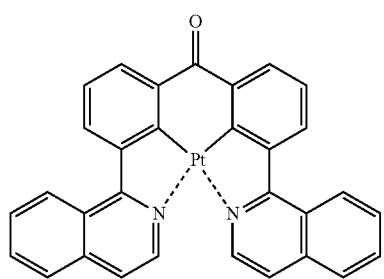
PD32 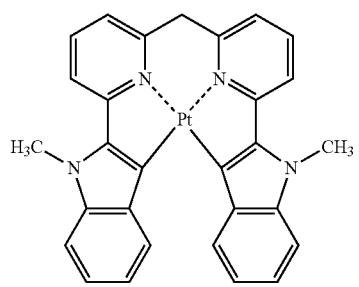
PD33 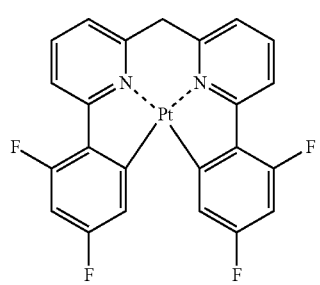
PD34 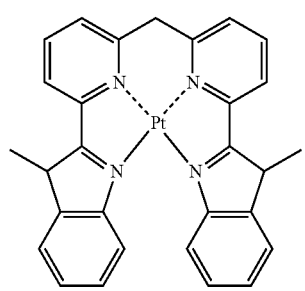
PD35 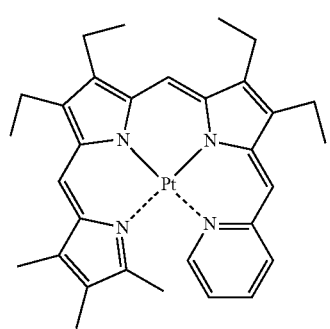
PD36 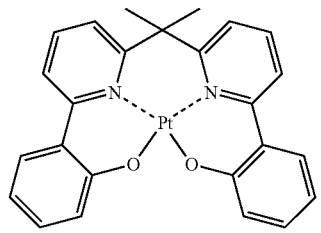
PD37 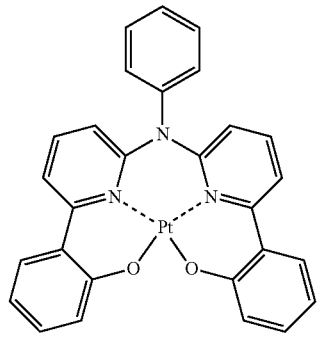
PD38 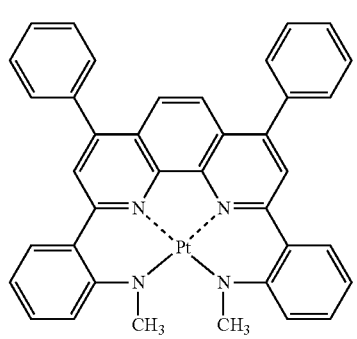
PD39 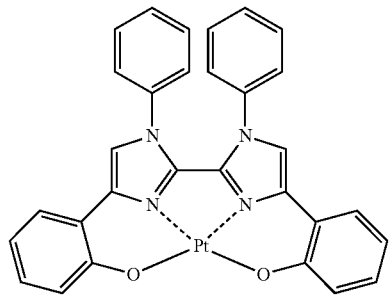
PD40 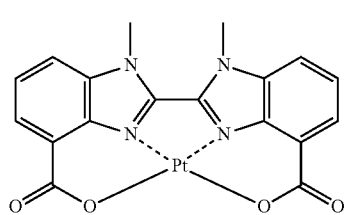

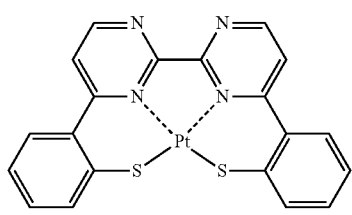
PD41
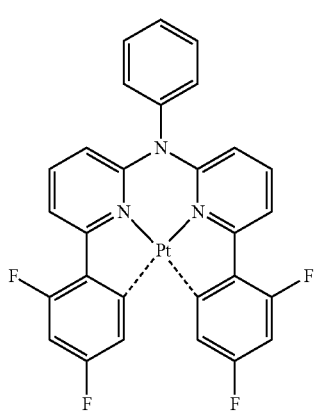
PD42
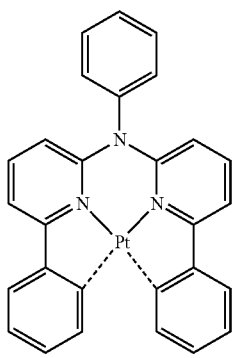
PD43
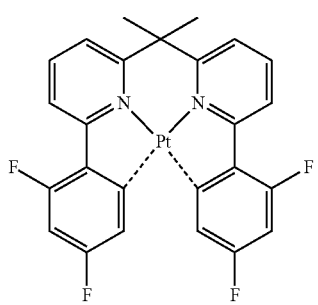
PD44
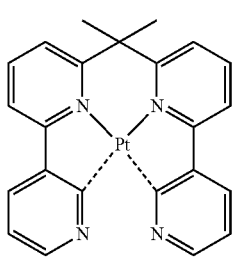
PD45
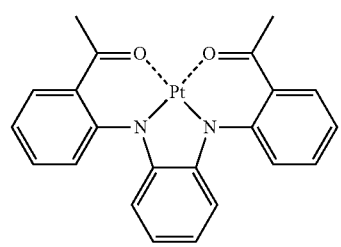
PD46
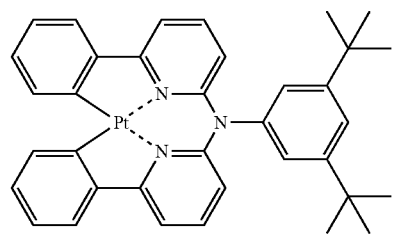
PD47
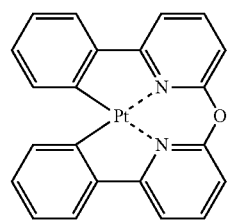
PD48
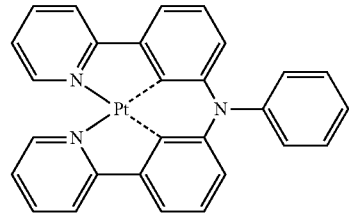
PD49
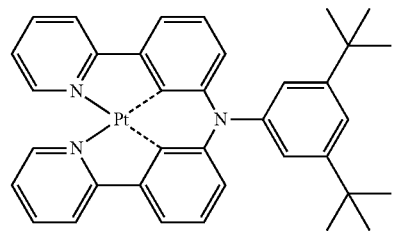
PD50
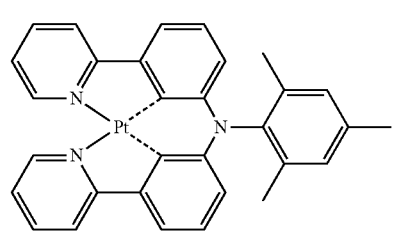
PD51

PD52 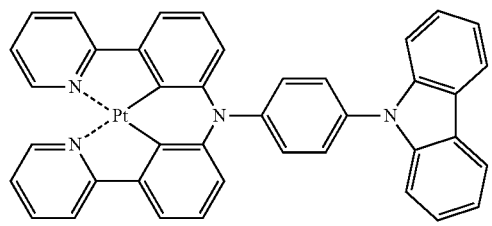
PD53 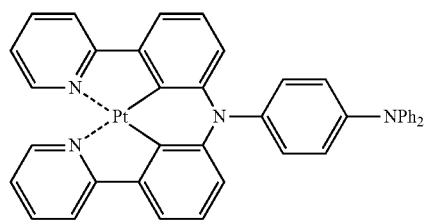
PD54 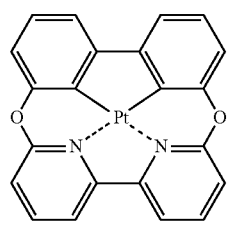
PD55 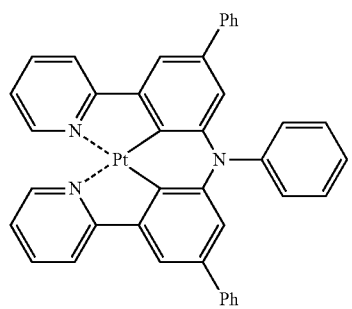
PD56 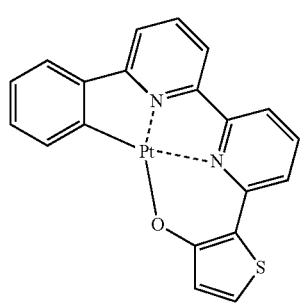
PD57 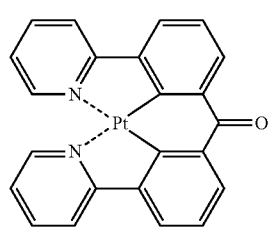
PD58 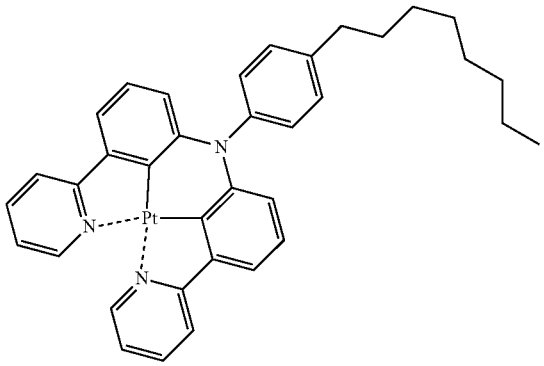
PD59 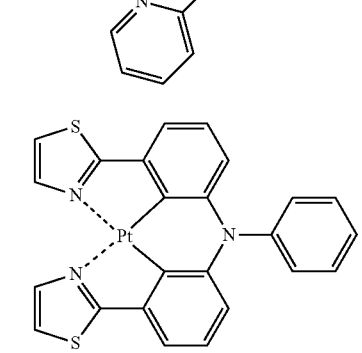
PD60 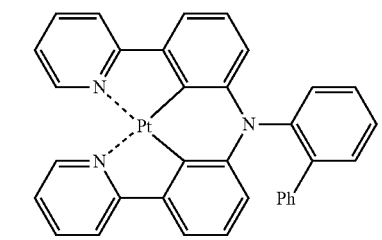
PD61 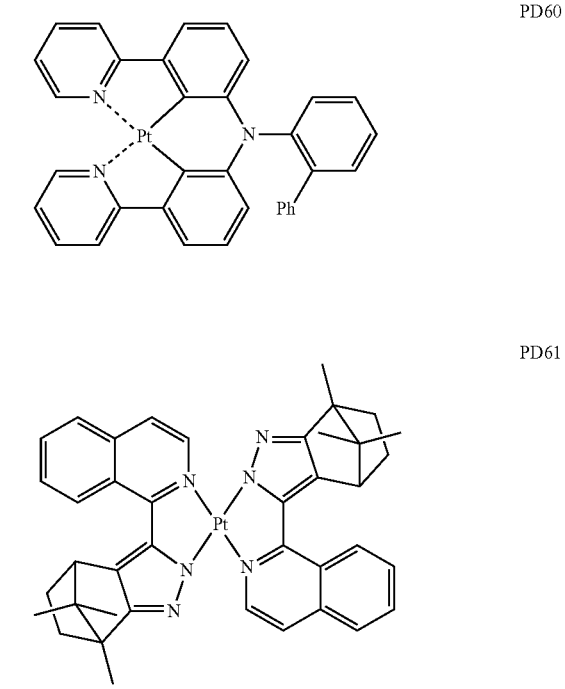
PD62 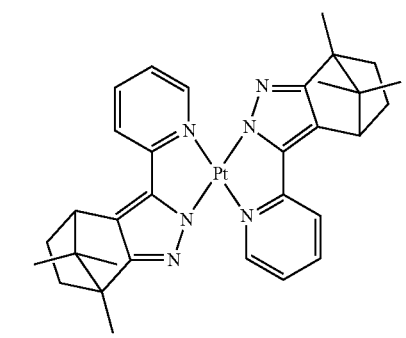

PD63 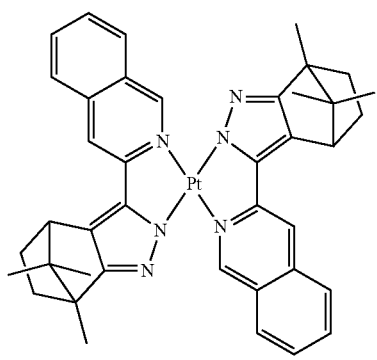
PD64 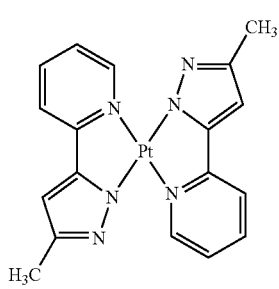
PD65 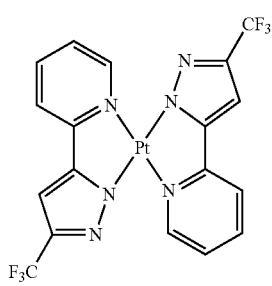
PD66 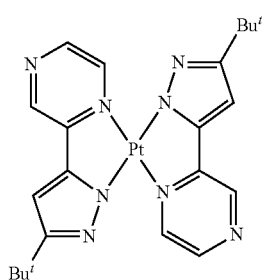
PD67 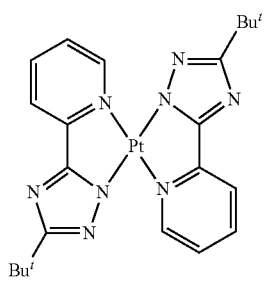
PD68 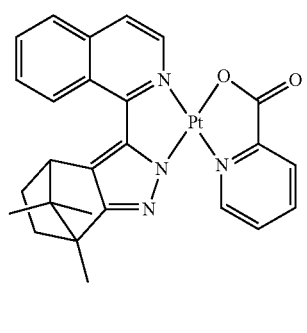
PD69 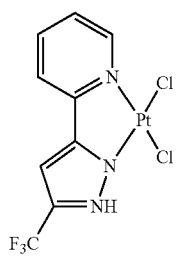
PD70 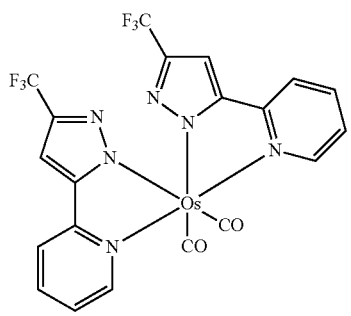
PD71 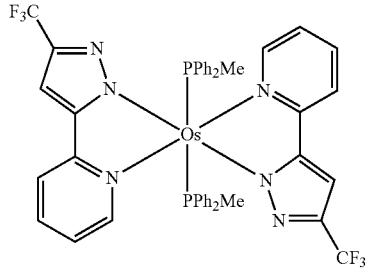
PD72 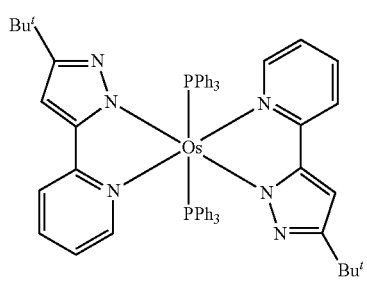

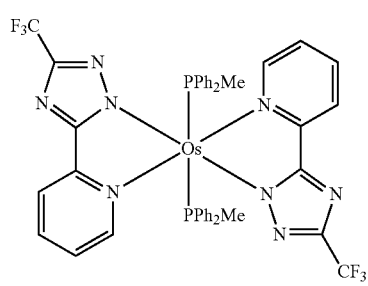
PD73
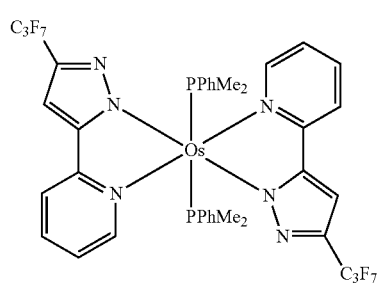
PD74
In some embodiments, the phosphorescent dopant may include PtOEP:
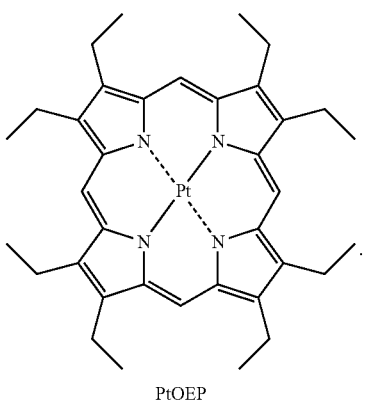
PtOEP
The fluorescent dopant may include at least one selected from DPVBi, DPAVBi, TBPe, DCM, DCJTB, Coumarin 6, and C545T:
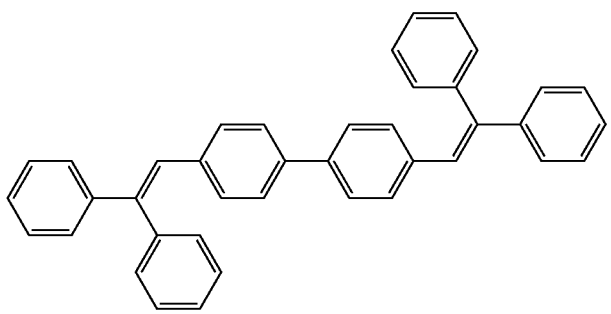
DPVBi
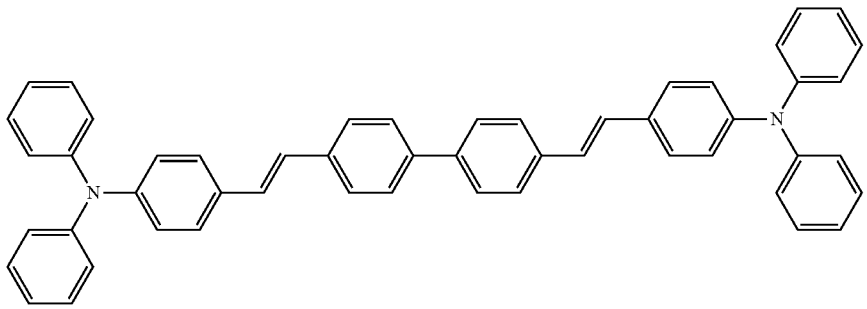
DPAVBi
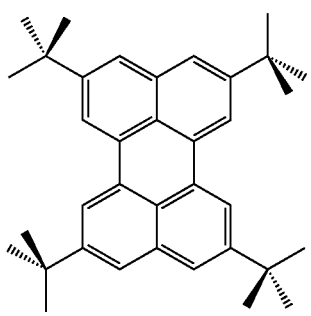
TBPe
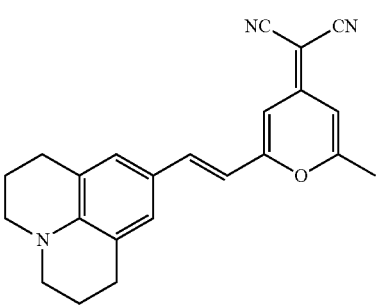
DCM

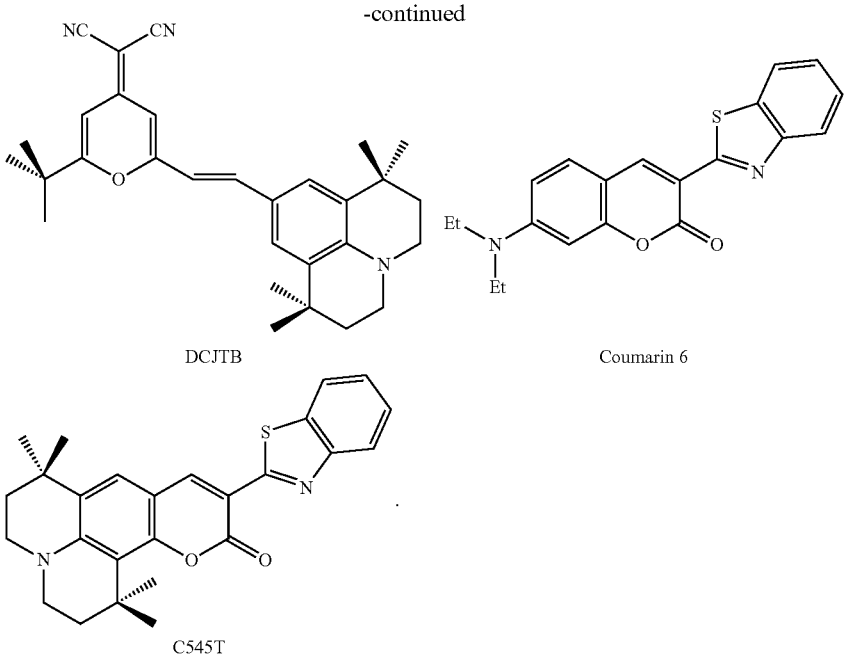

DCJTB                    Coumarin 6

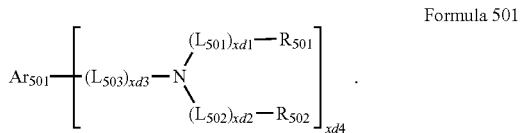

C545T

In some embodiments, the fluorescent dopant may include a compound represented by Formula 501:

$$Ar_{501}\!\!-\!\!\left[(L_{503})_{xd3}\!-\!N\!\!\begin{array}{c}(L_{501})_{xd1}\!-\!R_{501}\\ \\(L_{502})_{xd2}\!-\!R_{502}\end{array}\right]_{xd4}$$ Formula 501

In Formula 501, $Ar_{501}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) (wherein $Q_{501}$ to $Q_{503}$ may each be independently selected from hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group), $L_{501}$ to $L_{503}$ may each independently be defined the same as $L_{301}$ in the present specification, $R_{501}$ and $R_{502}$ may each be independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group; and a phenyl group, a biphenyl group, a terphenyl group, a naphthyl group a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, xd1 to xd3 may each be independently selected from 0, 1, 2, and 3, and xb4 may be selected from 1, 2, 3, and 4.

The fluorescent dopant may include at least one selected from Compounds FD1 to FD8:
FD1
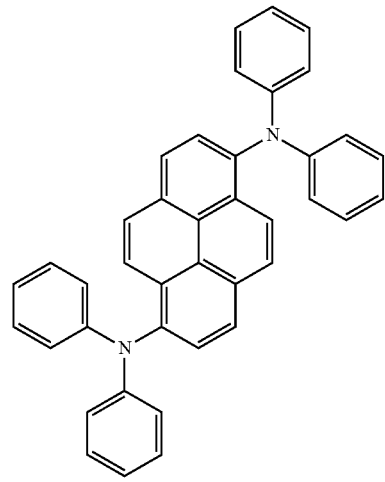
FD2
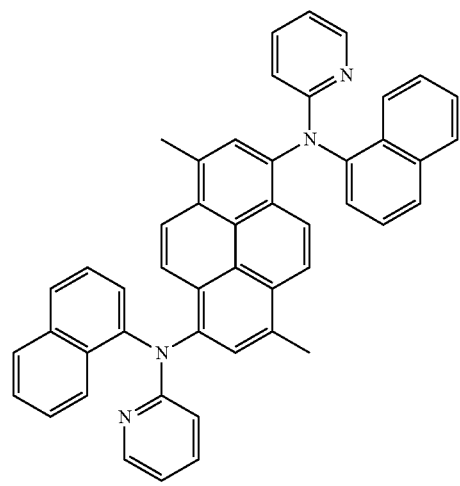
FD3
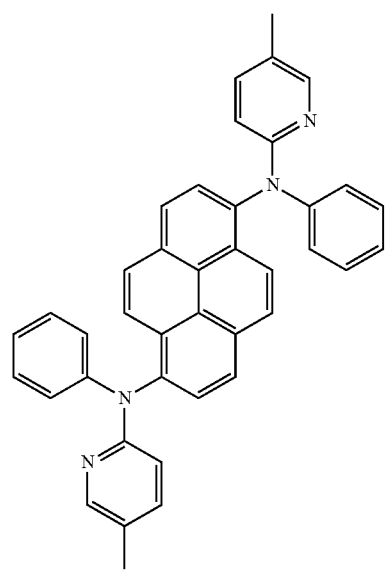
FD4
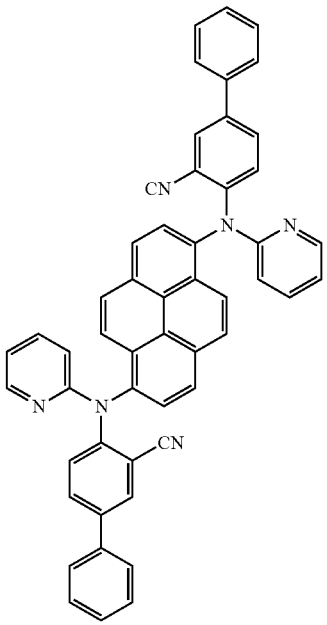
FD5
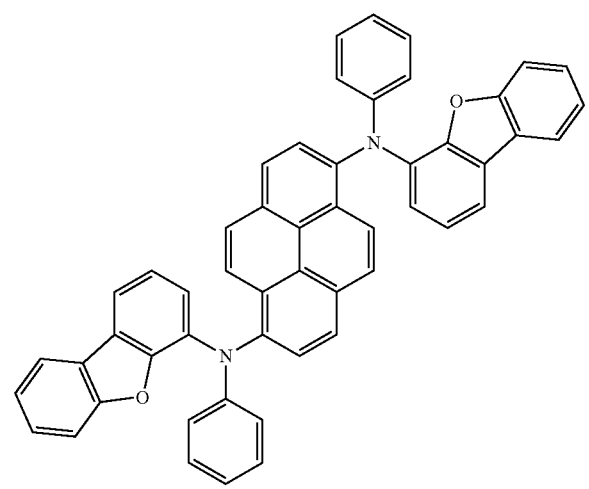
FD6
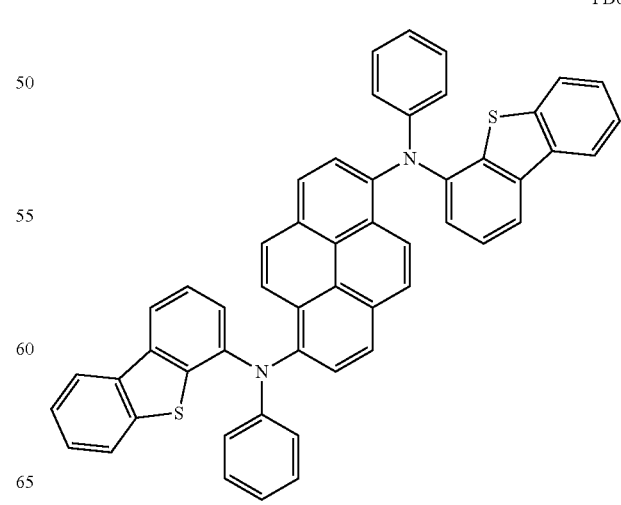

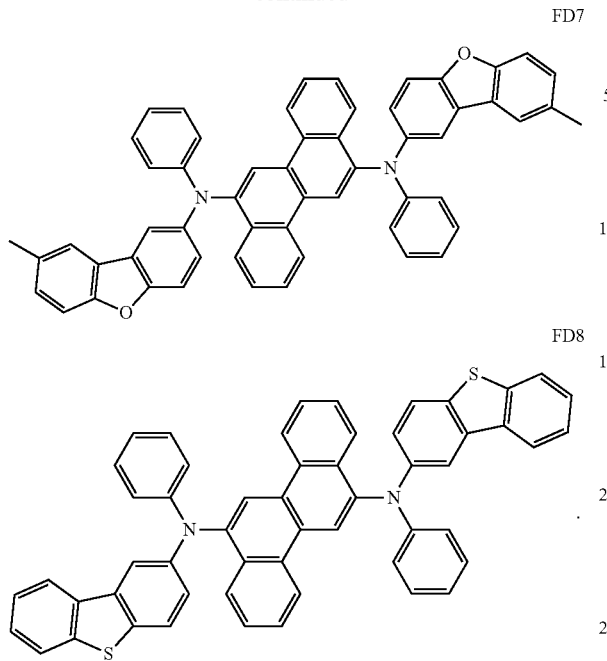

FD7

FD8

An amount of the dopant included in the EML may be in a range of about 0.01 to about 15 parts by weight, based on 100 parts by weight of the host, but the embodiments are not limited thereto.

A thickness of the EML may be in a range of about 100 Å to about 1,000 Å, for example, about 200 Å to about 600 Å. When the thickness of the EML is within any of these ranges, excellent (or suitable) emission characteristics may be obtained without a substantial increase in driving voltage.

The electron transport region may be disposed on the EML.

The electron transport region may include at least one selected from an HBL, an ETL, and an EIL, but the electron transport region is not limited thereto.

When the electron transport region includes an HBL, the HBL may be formed on the EML by using various suitable methods, such as vacuum deposition, spin coating, casting, a LB method, ink-jet printing, laser-printing, and/or LITI. When the HBL is formed by vacuum deposition and/or by spin coating, the deposition and coating conditions for the HBL may be determined by referring to the deposition and coating conditions for the HIL.

The HBL may include, for example, at least one selected from BCP and Bphen, but embodiments are not limited thereto:

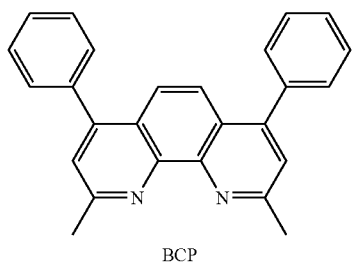

BCP

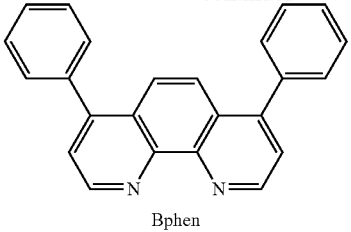

Bphen

A thickness of the HBL may be in a range of about 20 Å to about 1,000 Å, for example, about 30 Å to about 300 Å. When the thickness of the HBL is within any of these ranges, excellent (or suitable) hole blocking characteristics may be obtained without a substantial increase in driving voltage.

The electron transport region may have a structure of ETL/EIL or a structure of HBL/ETL/EIL, where the layers of each structure are sequentially stacked in the stated order from the EML, but the structure of the electron transport region is not limited thereto.

According to an example embodiment, the organic layer 150 may include the electron transport region that is disposed between the EML and the second electrode 190, and the electron transport region may include an ETL. The ETL may consist of a plurality of layers. For example, the electron transport region may include a first ETL and a second ETL.

The ETL may include the compound of Formula 1 according to an example embodiment.

A thickness of the ETL may be in a range of about 100 Å to about 1,000 Å, for example, about 150 Å to about 500 Å. When the thickness of the ETL is within any of these ranges, excellent (or suitable) electron transporting characteristics may be obtained without a substantial increase in driving voltage.

The ETL may further include, in addition to the materials described above, a metal-containing material.

The metal-containing material may include a Li complex. The Li complex may include, for example, Compound ET-D1 (e.g., lithium quinolate (LiQ)) and/or Compound ET-D2:

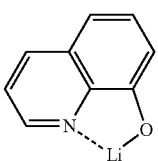

ET-D1

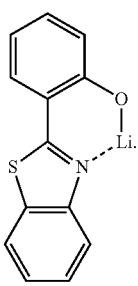

ET-D2

The electron transport region may include an EIL that facilitates electron injection from the second electrode 190.

The EIL may be formed on the ETL by using various suitable methods, such as vacuum deposition, spin coating, casting, a LB method, ink-jet printing, laser-printing, and/or LITI. When the EIL is formed by vacuum deposition and/or by spin coating, the deposition and coating conditions for the EIL may be determined by referring to the deposition and coating conditions for the HIL.

The EIL may include at least one selected from LiF, NaCl, CsF, $Li_2O$, BaO, and LiQ.

A thickness of the EIL may be in a range of about 1 Å to about 100 Å, for example, about 3 Å to about 90 Å. When the thickness of the EIL is within any of these ranges, suitable or satisfactory electron injecting characteristics may be obtained without a substantial increase in driving voltage.

The second electrode 190 may be disposed (e.g., positioned) on the electron transport region. The second electrode may be a cathode, which is an electron injection electrode. Here, a material for forming the second electrode 190 may be a material having a relatively low work function, such as a metal, an alloy, an electrically conductive compound, or a mixture thereof. Non-limiting examples of the material for forming the second electrode 190 may include lithium (Li), magnesium (Mg), aluminum (Al), aluminum-lithium (Al—Li), calcium (Ca), magnesium-indium (Mg—In), and magnesium-silver (Mg—Ag). In some embodiments, the material for forming the second electrode 190 may include ITO and/or IZO. The second electrode 190 may be a reflective electrode, a semi-transmissive electrode, or a transmissive electrode.

The organic layer 150 of the organic light-emitting device 10 may be formed by a deposition method using compounds according to example embodiments, or by a wet coating method using compounds that are prepared in solutions according to example embodiments.

The organic light-emitting device 10 according to an example embodiment may be included in various types (or kinds) of flat panel display apparatus, such as a passive matrix OLED display apparatus and/or an active matrix OLED display apparatus. For example, when the organic light-emitting device 10 is equipped with the active matrix OLED display apparatus, the first electrode 110 disposed on a side of the substrate may be electrically connected (e.g., coupled) to source and drain electrodes of a thin film transistor. In addition, the organic light-emitting device 10 may be equipped with a flat panel display apparatus that can display screens (e.g., images) at both sides.

Hereinbefore, the organic light-emitting device 10 has been described in connection with the drawing, but the embodiments are not limited thereto.

Hereinafter, representative substituents of the substituents used in the present specification are defined (carbon numbers limiting the substituents are non-limiting and do not limit characteristics of the substituents). It will be understood that if a substituent that appears in the present disclosure is not expressly defined above, the definition of the substituent is consistent with a general definition thereof, unless stated otherwise.

A $C_1$-$C_{60}$ alkyl group as used herein may refer to a linear or branched aliphatic hydrocarbon monovalent group having 1 to 60 carbon atoms, and non-limiting examples thereof include a methyl group, an ethyl group, a propyl group, an isobutyl group, a sec-butyl group, a ter-butyl group, a pentyl group, an iso-amyl group, and a hexyl group. A $C_1$-$C_{60}$ alkylene group as used herein may refer to a divalent group having the same structure as the $C_1$-$C_{60}$ alkyl group.

A $C_1$-$C_{60}$ alkoxy group as used herein may refer to a monovalent group represented by —$OA_{101}$ (wherein $A_{101}$ is the $C_1$-$C_{60}$ alkyl group), and non-limiting examples thereof include a methoxy group, an ethoxy group, and an isopropoxy group.

A $C_2$-$C_{60}$ alkenyl group as used herein may refer to a hydrocarbon group having at least one carbon double bond at one or more positions along a hydrocarbon chain of the $C_2$-$C_{60}$ alkyl group (e.g., in the middle or at either terminal end of the $C_2$-$C_{60}$ alkyl group), and non-limiting examples thereof include an ethenyl group, a propenyl group, and a butenyl group. A $C_2$-$C_{60}$ alkenylene group as used herein may refer to a divalent group having the same structure as the $C_2$-$C_{60}$ alkenyl group.

A $C_2$-$C_{60}$ alkynyl group as used herein may refer to a hydrocarbon group having at least one carbon triple bond at one or more positions along a hydrocarbon chain of the $C_2$-$C_{60}$ alkyl group (e.g., in a middle or at either terminal end of the $C_2$-$C_{60}$ alkyl group), and non-limiting examples thereof include an ethynyl group and a propynyl group. A $C_2$-$C_{60}$ alkynylene group as used herein may refer to a divalent group having the same structure as the $C_2$-$C_{60}$ alkynyl group.

A $C_3$-$C_{10}$ cycloalkyl group as used herein may refer to a monovalent hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. A $C_3$-$C_{10}$ cycloalkylene group used herein may refer to a divalent group having the same structure as the $C_3$-$C_{10}$ cycloalkyl group.

A $C_2$-$C_{10}$ heterocycloalkyl group as used herein may refer to a monovalent monocyclic group having at least one heteroatom selected from N, O, P, and S as a ring-forming atom and 1 to 10 carbon atoms, and non-limiting examples thereof include a tetrahydrofuranyl group and a tetrahydrothiophenyl group. A $C_2$-$C_{10}$ heterocycloalkylene group as used herein may refer to a divalent group having the same structure as the $C_2$-$C_{10}$ heterocycloalkyl group.

A $C_3$-$C_{10}$ cycloalkenyl group as used herein may refer to a monovalent monocyclic group that has 3 to 10 carbon atoms and at least one double bond in the ring thereof and does not have aromaticity (e.g., the ring is not aromatic), and non-limiting examples thereof include a cyclopentenyl group, a cyclohexenyl group, and a cycloheptenyl group. A $C_3$-$C_{10}$ cycloalkenylene group as used herein may refer to a divalent group having the same structure as the $C_3$-$C_{10}$ cycloalkenyl group.

A $C_2$-$C_{10}$ heterocycloalkenyl group as used herein may refer to a monovalent monocyclic group that has at least one heteroatom selected from N, O, P, and S as a ring-forming atom, 2 to 10 carbon atoms, and at least one double bond in the ring. Non-limiting examples of the $C_2$-$C_{10}$ heterocycloalkenyl group include a 2,3-hydrofuranyl group and a 2,3-hydrothiophenyl group. A $C_2$-$C_{10}$ heterocycloalkenylene group as used herein may refer to a divalent group having the same structure as the $C_2$-$C_{10}$ heterocycloalkenyl group.

A $C_6$-$C_{60}$ aryl group as used herein may refer to a monovalent group having a carbocyclic aromatic system having 6 to 60 carbon atoms, and a $C_6$-$C_{60}$ arylene group as used herein may refer to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and/or the $C_6$-$C_{60}$ arylene group include two or more rings, the respective rings may be fused to (with) each other.

A $C_1$-$C_{60}$ heteroaryl group as used herein may refer to a monovalent group having a carbocyclic aromatic system that has at least one heteroatom selected from N, O, P, and S as a ring-forming atom, and 1 to 60 carbon atoms. A $C_1$-$C_{60}$ heteroarylene group as used herein may refer to a divalent group having a carbocyclic aromatic system that has at least one heteroatom selected from N, O, P, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and/or the $C_1$-$C_{60}$ heteroarylene group include two or more rings, the respective rings may be fused to (with) each other.

A $C_6$-$C_{60}$ aryloxy group as used herein may refer to a monovalent group represented by —$OA_{102}$ (wherein $A_{102}$ is the $C_6$-$C_{60}$ aryl group), and a $C_6$-$C_{60}$ arylthio group as used herein may refer to a monovalent group represented by —$SA_{103}$ (wherein $A_{103}$ is the $C_6$-$C_{60}$ aryl group).

A monovalent non-aromatic condensed polycyclic as used herein may refer to a monovalent group that has two or more rings condensed to each other, has carbon atoms only as ring-forming atoms, and has non-aromaticity in the entire molecular structure (e.g., does not have overall aromaticity). A non-limiting example of the monovalent non-aromatic condensed polycyclic group is a fluorenyl group. A divalent non-aromatic condensed polycyclic group as used herein may refer to a divalent group having the same structure as the monovalent non-aromatic condensed polycyclic group.

A monovalent non-aromatic condensed heteropolycyclic group as used herein may refer to a monovalent group that has two or more rings condensed to each other, has at least one heteroatom selected from N, O, P, and S as a ring-forming atom, in addition to carbon atoms, and has non-aromaticity in the entire molecular structure (e.g., does not have overall aromaticity). A non-limiting example of the monovalent non-aromatic condensed heteropolycyclic group is a carbazolyl group. A divalent non-aromatic condensed heteropolycyclic group used herein may refer to a divalent group having the same structure as the monovalent non-aromatic condensed heteropolycyclic group.

In the present specification, at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$, wherein $Q_{11}$ to $Q_{17}$, $Q_{21}$ to $Q_{27}$, and $Q_{31}$ to $Q_{37}$ may each be independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{11}$)($Q_{12}$), —Si($Q_{13}$)($Q_{14}$)($Q_{15}$), and —B($Q_{16}$)($Q_{17}$);

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_{11}$ to $Q_{17}$, $Q_{21}$ to $Q_{27}$, and $Q_{31}$ to $Q_{37}$ may each be independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

The term "Ph" as used herein may refer to a phenyl group, the term "Me" as used herein may refer to a methyl group, the term "Et" as used herein may refer to an ethyl group, and the term "ter-Bu" or "Bu$^t$" as used herein may refer to a tert-butyl group.

Hereinafter, an organic light-emitting device according to an example embodiment will be described in more detail with reference to Examples below.

Synthesis Examples

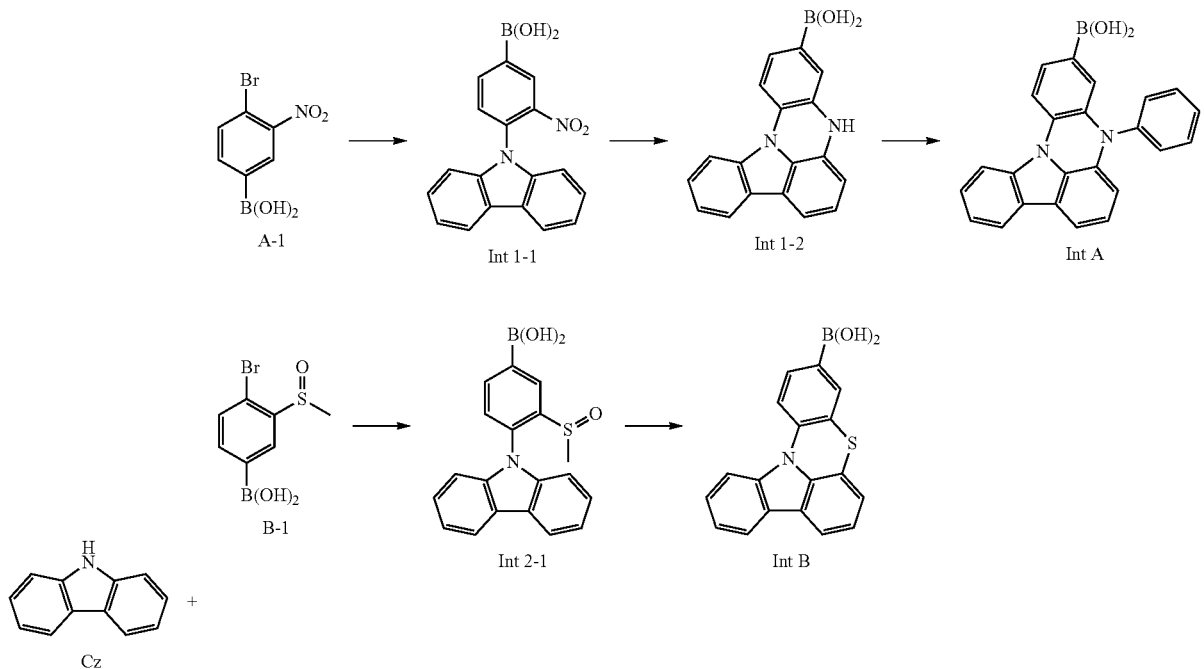

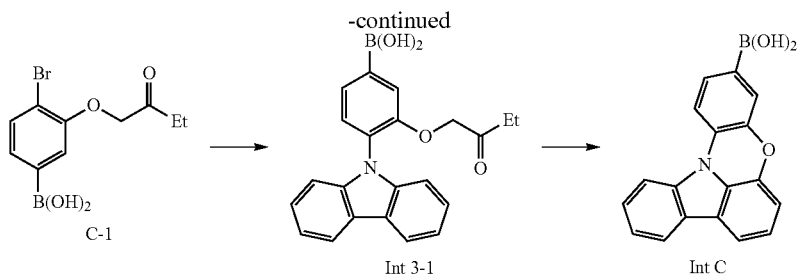

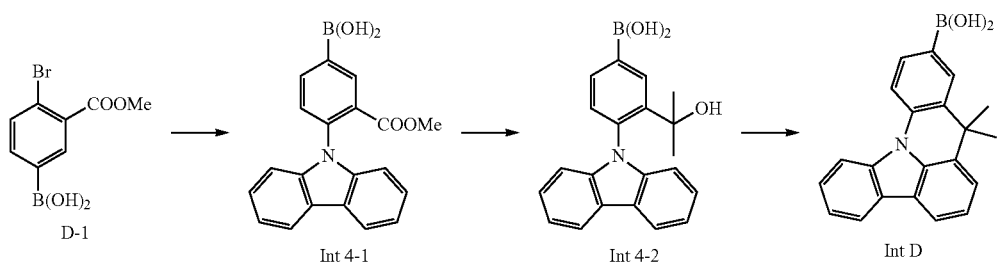

Synthesis of Intermediate 1-1

Pd(dba)3 (0.03 eq), (t-Bu)$_3$P (0.06 eq), and toluene (0.1 M) were added to a flask containing a starting material (i.e., Cz) and Compound A-1 to form a mixture. About 12 hours later, the mixture was cooled to room temperature, and then, was extracted using methylene chloride (MC) and washed out with distilled water. The washed mixture was dried using MgSO$_4$ and concentrated under a reduced pressure. The resultant residues obtained therefrom were separated by column chromatography (hereinafter, "column"), so as to obtain Intermediate 1-1 (yield: 68%). The resulting compound was identified by high resolution mass spectrometry (HRMS).

HRMS for $C_{18}H_{13}BN_2O_4$ [M]+: calcd: 332.12. found: 331.

Synthesis of Intermediate 1-2

5 g of Intermediate 1-1 was dissolved in 15 g of triethylphosphite, and then, the mixed solution was stirred under reflux for about 12 hours in a nitrogen atmosphere. After completion of the reaction, non-reactive triethylphosphite was removed via a vacuum distillation method. The resultant residues obtained therefrom were separated by a column using a combination of hexane and MC (mixed at a volume ratio of 4:1 (v/v)), so as to obtain the desired compound, Intermediate 1-2 (yield: 46.5%).

HRMS for $C_{18}H_{13}BN_2O_2$ [M]+: calcd: 300.12. found: 299.

Synthesis of Intermediate A

Pd(dba)$_3$ (0.03 eq), (t-Bu)$_3$P (0.06 eq), and toluene (0.1 M) were added to a flask containing Intermediate 1-2 and bromobenzene to form a mixture. About 12 hours later, the mixture was cooled to room temperature, and then, was extracted using MC and washed out with distilled water. The washed mixture was dried using MgSO$_4$ and concentrated under a reduced pressure. The resultant residues obtained therefrom were separated by a column, so as to obtain Intermediate A (yield: 82%).

HRMS for $C_{18}H_{13}BN_2O_4$ [M]+: calcd: 332.12. found: 331.

Synthesis of Intermediate 2-1

Pd(dba)$_3$ (0.03 eq), (t-Bu)$_3$P (0.06 eq), and toluene (0.1 M) were added to a flask containing a starting material (i.e., Cz) and Compound B-1 to form a mixture. About 12 hours later, the mixture was cooled to room temperature, and then, was extracted using MC and washed out with distilled water. The washed mixture was dried using MgSO$_4$ and concentrated under a reduced pressure. The resultant residues obtained therefrom were separated by a column, so as to obtain Intermediate 2-1 (yield: 69%).

HRMS for $C_{19}H_{16}BNO_3S$[M]+: calcd: 349.21. found: 348.

Synthesis of Intermediate B

Intermediate 2-1 and trifluoromethanesulfonic acid (CF$_3$SO$_3$H) were added to a flask to form a mixture. The mixture was stirred at room temperature for 24 hours, and then, was stirred using a combination of water and pyridine (mixed at a volume ratio of 8:1) for 30 minutes. The stirred mixture was cooled to room temperature, extracted using MC, dried using MgSO$_4$, and then, concentrated under a reduced pressure. The resultant residues obtained therefrom were separated by a column, so as to obtain Intermediate B (yield: 82%).

HRMS for $C_{18}H_{12}BN_2O_2S$[M]+: calcd: 317.17. found: 316.

Synthesis of Intermediate 3-1

Pd(dba)$_3$ (0.03 eq), (t-Bu)$_3$P (0.06 eq), and toluene (0.1 M) were added to a flask containing a starting material (i.e., Cz) and Compound C-1 to form a mixture. About 12 hours later, the mixture was cooled to room temperature, and then, was extracted using MC and washed out with distilled water. The washed mixture was dried using MgSO$_4$ and concentrated under a reduced pressure. The resultant residues obtained therefrom were separated by a column, so as to obtain Intermediate 3-1 (yield: 72%).

HRMS for $C_{22}H_{20}BNO_4$[M]+: calcd: 373.22. found: 372.

Synthesis of Intermediate C

Intermediate 3-1 and $CF_3SO_3H$ were added to a flask to form a mixture. The mixture was stirred at room temperature for 24 hours, and then, was stirred using a combination of water and pyridine (mixed at a volume ratio of 8:1) for 30 minutes. The stirred mixture was cooled to room temperature, extracted using MC, dried using $MgSO_4$, and then, concentrated under a reduced pressure. The resultant residues obtained therefrom were separated by a column, so as to obtain Intermediate C (yield: 41%).

HRMS for $C_{18}H_{12}BNO_3$[M]+: calcd: 301.11. found: 300.

Synthesis of Intermediate 4-1

$Pd(dba)_3$ (0.03 eq), $(t-Bu)_3P$ (0.06 eq), and toluene (0.1 M) were added to a flask containing a starting material (i.e., Cz) and Compound D-1. About 12 hours later, the mixture was cooled to room temperature, and then, was extracted using MC and washed out with distilled water. The washed mixture was dried using $MgSO_4$ and concentrated under a reduced pressure. The resultant residues obtained therefrom were separated by a column, so as to obtain Intermediate 4-1 (yield: 61%).

HRMS for $C_{20}H_{16}BNO_4$ [M]+: calcd: 345.16. found: 344.

Synthesis of Intermediate 4-2

5 g (1 eq) of Intermediate 4-1 was dissolved in 100 ml of ether, and then, the mixed solution was cooled to a temperature of about −78° C. Methyllithium (1.2 eq) was added thereto, and the mixed solution was stirred for about 1 hour. The temperature was gradually increased to room temperature, and then, the mixed solution was further stirred at room temperature for 4 hours. After completion of the reaction, an organic layer was extracted therefrom using 200 mL of water, and then, was concentrated under a reduced pressure. The resultant residues were re-crystallized by using a combination of ethanol and acetone (mixed at a volume ratio of 1:1), so as to obtain Intermediate 4-2 (yield: 67%).

HRMS for $C_{21}H_{20}BNO_3$ [M]+: calcd: 345.21. found: 344.

Synthesis of Intermediate D

Intermediate 4-2 was dissolved in 150 mL of a strong $H_3PO_4$ solution, and then, the mixed solution was stirred for about 5 hours. An organic layer was extracted therefrom using 200 mL of water and 200 mL of ethyl acetate, and then, was concentrated under a reduced pressure. The resultant residues were re-crystallized by using 150 mL of ethanol, so as to obtain Intermediate D (yield: 72%).

HRMS for $C_{21}H_{18}BNO_2$ [M]+: calcd: 327.19. found: 326.

Synthesis of Compound A1

Intermediate A (1 eq), (4-bromophenyl)diphenylphosphine oxide (1.2 eq), $Pd(PPh_3)_4$ (0.02 eq), $Na_2CO_3$ (1.2 eq), toluene, distilled water, and ethanol (0.1 M, mixed at a volume ratio of 5:3:2) were added together to form a mixture. After the mixture was stirred under reflux for about 12 hours, the stirred mixture was cooled to room temperature, and then, was extracted using MC and washed out with distilled water. The washed mixture was dried using $MgSO_4$ and concentrated under a reduced pressure. The resultant residues obtained therefrom were separated by a column, so as to obtain Compound A1 (yield: 76%). Compound A1 was then identified according to Elemental Analysis and HRMS.

Elemental Analysis for $C_{42}H_{29}N_2OP$ calcd: C, 82.88; H, 4.80; N, 4.60; O, 2.63; P, 5.09.

HRMS for $C_{42}H_{29}N_2OP$ [M]+: calcd: 608.68. found: 607.

Synthesis of Compound A3

Compound A3 (yield: 82%) was synthesized in the same (or substantially the same) manner as in Synthesis of Compound A1, except that (4-(2-bromopyrimidin-5-yl)phenyl)diphenylphosphine oxide was used instead of (4-bromophenyl)diphenylphosphine oxide.

Elemental Analysis for $C_{46}H_{31}N_4OP$ calcd: C, 80.45; H, 4.55; N, 8.16; O, 2.33; P, 4.51.

HRMS for $C_{46}H_{31}N_4OP$ [M]+: calcd: 686.75. found: 685.

Synthesis of Compound A5

Compound A5 (yield: 69%) was synthesized in the same (or substantially the same) manner as in Synthesis of Compound A1, except that (4-bromophenyl)diphenylphosphine sulfide was used instead of (4-bromophenyl)diphenylphosphine oxide.

Elemental Analysis for $C_{42}H_{29}N_2OS$ calcd: C, 80.75; H, 4.68; N, 4.48; P, 4.96; S, 5.13.

HRMS for $C_{42}H_{29}N_2OS$ [M]+: calcd: 624.74. found: 623.

Synthesis of Compound A7

Compound A7 (yield: 71%) was synthesized in the same (or substantially the same) manner as in Synthesis of Compound A1, except that (4-(2-bromopyrimidin-5-yl)phenyl)diphenylphosphine sulfide was used instead of (4-bromophenyl)diphenylphosphine oxide.

Elemental Analysis for $C_{46}H_{31}N_4PS$ calcd: C, 78.61; H, 4.45; N, 7.97; P, 4.41; S, 4.56.

HRMS for $C_{46}H_{31}N_4PS$ [M]+: calcd: 702.82. found: 701.

Synthesis of Compound A9

Compound A9 (yield: 63%) was synthesized in the same (or substantially the same) manner as in Synthesis of Compound A1, except that (6-bromonaphthalen-2-yl)diphenylphosphine oxide was used instead of (4-bromophenyl)diphenylphosphine oxide.

Elemental Analysis for $C_{46}H_{31}N_2OP$ calcd: C, 83.87; H, 4.74; N, 4.25; O, 2.43; P, 4.70.

HRMS for $C_{46}H_{31}N_2OP$ [M]+: calcd: 658.74. found: 657.

Synthesis of Compound A20

Compound A20 (yield: 59%) was synthesized in the same (or substantially the same) manner as in Synthesis of Compound A1, except that (4-(4-bromo-1,3,5-triazin-2-yl)phenyl)diphenylphosphine selenide was used instead of (4-bromophenyl)diphenylphosphine oxide.

Elemental Analysis for $C_{45}H_{30}N_5PSe$ calcd: C, 72.00; H, 4.03; N, 9.33; P, 4.13; Se, 10.52.

HRMS for $C_{45}H_{30}N_5PSe$ [M]+: calcd: 750.7. found: 749.

Synthesis of Compound A22

Compound A22 (yield: 67%) was synthesized in the same (or substantially the same) manner as in Synthesis of Compound A1, except that (4-bromophenyl)diphenylphosphine selenide was used instead of (4-bromophenyl)diphenylphosphine oxide.

Elemental Analysis for $C_{42}H_{29}N_2PSe$ calcd: C, 75.11; H, 4.35; N, 4.17; P, 4.61; Se, 11.76.

HRMS for $C_{42}H_{29}N_2PSe$ [M]+: calcd: 671.64. found: 670.

Synthesis of Compound A24

Compound A24 (yield: 52%) was synthesized in the same (or substantially the same) manner as in Synthesis of Compound A1, except that (4-(2-bromopyrimidin-5-yl)phenyl)diphenylphosphine selenide was used instead of (4-bromophenyl)diphenylphosphine oxide.

Elemental Analysis for $C_{46}H_{31}N_4PSe$ calcd: C, 73.70; H, 4.17; N, 7.47; P, 4.13; Se, 10.53.

HRMS for $C_{46}H_{31}N_4PSe$ [M]+: calcd: 749.72. found: 748.

Synthesis of Compound A26

Intermediate B (1 eq), (4-bromophenyl)diphenylphosphine oxide (1.2 eq), $Pd(PPh_3)_4$ (0.02 eq), $Na_2CO_3$ (1.2 eq), toluene, distilled water, and ethanol (0.1 M, mixed at a ratio of volume 5:3:2) were added together to form a mixture. After the mixture was stirred under reflux for about 12 hours, the stirred mixture was cooled to room temperature, and then, was extracted using MC and washed out with distilled water. The washed mixture was dried using MgSO$_4$ and concentrated under a reduced pressure. The resultant residues obtained therefrom were separated by a column, so as to obtain Compound A26 (yield: 77%). Compound A26 was then identified according to Elemental Analysis and HRMS.

Elemental Analysis for C$_{36}$H$_{24}$NOPS calcd: C, 78.67; H, 4.40; N, 2.55; O, 2.91; P, 5.64; S, 5.83.

HRMS for C$_{36}$H$_{24}$NOPS [M]+: calcd: 549.63. found: 548.

Synthesis of Compound A28

Compound A28 (yield: 66%) was synthesized in the same (or substantially the same) manner as in Synthesis of Compound A26, except that (4-(2-bromopyrimidin-5-yl)phenyl) diphenylphosphine oxide was used instead of (4-bromophenyl)diphenylphosphine oxide.

Elemental Analysis for C$_{40}$H$_{26}$N$_3$POS calcd: C, 76.54; H, 4.18; N, 6.69; O, 2.55; P, 4.93; S, 5.11.

HRMS for C$_{40}$H$_{26}$N$_3$POS [M]+: calcd: 627.70. found: 626.

Synthesis of Compound A29

Compound A29 (yield: 72%) was synthesized in the same (or substantially the same) manner as in Synthesis of Compound A26, except that (2-bromopyrimidin-5-yl)diphenylphosphine oxide was used instead of (4-bromophenyl)diphenylphosphine oxide.

Elemental Analysis for C$_{34}$H$_{22}$N$_3$OPS calcd: C, 74.03; H, 4.02; N, 7.62; O, 2.90; P, 5.62; S, 5.81.

HRMS for C$_{34}$H$_{22}$N$_3$OPS [M]+: calcd: 551.60. found: 550.

Synthesis of Compound A30

Intermediate C (1 eq), (4-bromophenyl)diphenylphosphine oxide (1.2 eq), Pd(PPh$_3$)$_4$ (0.02 eq), Na$_2$CO$_3$ (1.2 eq), toluene, distilled water, and ethanol (0.1 M, mixed at a ratio of volume 5:3:2) were added together to form a mixture. After the mixture was stirred under reflux for about 12 hours, the stirred mixture was cooled to room temperature, and then, was extracted using MC and washed out with distilled water. The washed mixture was dried using MgSO$_4$ and concentrated under a reduced pressure. The resultant residues obtained therefrom were separated by a column, so as to obtain Compound A30 (yield: 78.5). Compound A30 was then identified according to Elemental Analysis and HRMS.

Elemental Analysis for C$_{36}$H$_{24}$NO$_2$P calcd: C, 81.04; H, 4.53; N, 2.63; O, 6.00; P, 5.81.

HRMS for C$_{36}$H$_{24}$NO$_2$P [M]+: calcd: 533.57. found: 532.

Synthesis of Compound A35

Compound A35 (yield: 76%) was synthesized in the same (or substantially the same) manner as in Synthesis of Compound A26, except that (6-bromopyridin-3-yl)diphenylphosphine sulfide was used instead of (4-bromophenyl)diphenylphosphine oxide.

Elemental Analysis for C$_{35}$H$_{23}$N$_2$PS$_2$ calcd: C, 74.18; H, 4.09; N, 4.94; P, 5.47; S, 11.32.

HRMS for C$_{35}$H$_{23}$N$_2$PS$_2$ [M]+: calcd: 566.68. found: 565.

Synthesis of Compound A37

Compound A37 (yield: 64%) was synthesized in the same (or substantially the same) manner as in Synthesis of Compound A26, except that (2-bromopyrimidin-5-yl)diphenylphosphine sulfide was used instead of (4-bromophenyl)diphenylphosphine oxide.

Elemental Analysis for C$_{34}$H$_{22}$N$_3$PS$_2$ calcd: C, 71.94; H, 3.91; N, 7.40; P, 5.46; S, 11.30.

HRMS for C$_{34}$H$_{22}$N$_3$PS$_2$ [M]+: calcd: 567.66. found: 566.

Synthesis of Compound A38

Compound A38 (yield: 67%) was synthesized in the same (or substantially the same) manner as in Synthesis of Compound A30, except that (4-bromophenyl)diphenylphosphine sulfide was used instead of (4-bromophenyl)diphenylphosphine oxide.

Elemental Analysis for C$_{36}$H$_{24}$NOPS calcd: C, 78.67; H, 4.40; N, 2.55; O, 2.91; P, 5.64; S, 5.83.

HRMS for C$_{36}$H$_{24}$NOPS [M]+: calcd: 549.63. found: 548.

Synthesis of Compound A45

Compound A45 (yield: 79%) was synthesized in the same (or substantially the same) manner as in Synthesis of Compound A26, except that (3-bromophenyl)diphenylphosphine oxide was used instead of (4-bromophenyl)diphenylphosphine oxide.

Elemental Analysis for C$_{34}$H$_{22}$N$_3$PS$_2$ calcd: C, 71.94; H, 3.91; N, 7.40; P, 5.46; S, 11.30.

HRMS for C$_{34}$H$_{22}$N$_3$PS$_2$ [M]+: calcd: 567.66. found: 566.

Synthesis of Compound A50

Compound A50 (yield: 74%) was synthesized in the same (or substantially the same) manner as in Synthesis of Compound A26, except that (6-bromonaphthalen-2-yl)diphenylphosphine selenide was used instead of (4-bromophenyl) diphenylphosphine oxide.

Elemental Analysis for C$_{40}$H$_{26}$NPSSe calcd: C, 72.50; H, 3.96; N, 2.11; P, 4.67; S, 4.84; Se, 11.92.

HRMS for C$_{40}$H$_{26}$NPSSe [M]+: calcd: 662.65. found: 661.

EXAMPLES

Examples 1-16

As an anode, a 15 Ω/cm$^2$ (500 Å) ITO glass substrate (manufactured by Corning, Inc.) was cut into a size of 50 mm×50 mm×0.5 mm and ultrasonically washed with isopropyl alcohol and pure water, each for 10 minutes. Afterwards, the ITO glass substrate was irradiated by UV light for 10 minutes, cleaned by exposure to ozone, and then, mounted on a vacuum depositor. 2-TNATA, which is a material for forming an HIL, was vacuum-deposited on the substrate to form an HIL having a thickness of 600 Å, and then, 4,4'-bos[N-(1-naphthyl)-N-phenylamino]biphenyl (hereinafter, referred to as NPB), which is a hole transporting compound, was vacuum-deposited on the HIL to form an HTL having a thickness of 300 Å. Subsequently, bis-(1-phenylisoquinolyl) iridium(III)acetylacetonate (Ir(ppy)$_3$), which is a green phosphorous dopant, and CBP were co-deposited at a ratio of 15:85 on the HTL to form an EML having a thickness of 300 Å. Subsequently, compounds listed in Table 1 below were respectively deposited on the EML to form an ETL having a thickness of 300 Å, and then, Al was vacuum-deposited on the ETL to form a cathode electrode (i.e., Al electrode) having a thickness of 1,200 Å, thereby manufacturing an organic light-emitting device.

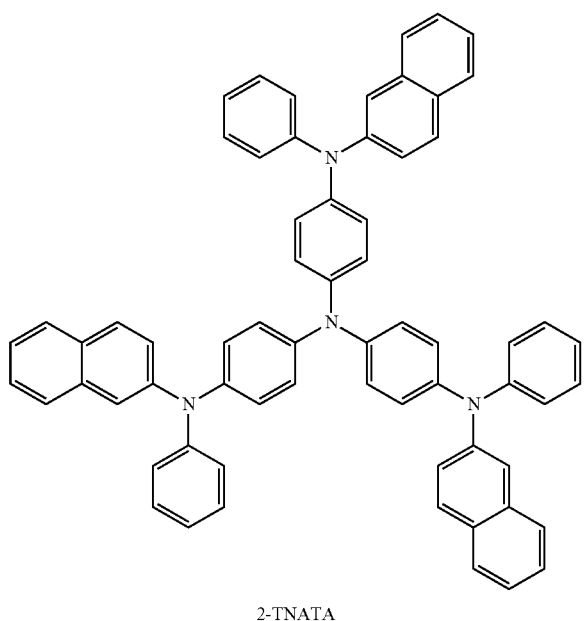

2-TNATA

NPB

CBP

Comparative Example 1

An organic light-emitting device was manufactured in the same (or substantially the same) manner as in Examples 1-16, except that in forming the ETL, aluminum tris(8-hydroxyquinoline) (Alq₃) was used instead of the compound of Table 1.

Comparative Example 2

An organic light-emitting device was manufactured in the same (or substantially the same) manner as in Examples 1-16, except that in forming the ETL, Compound 100 was used instead of the compound of Table 1.

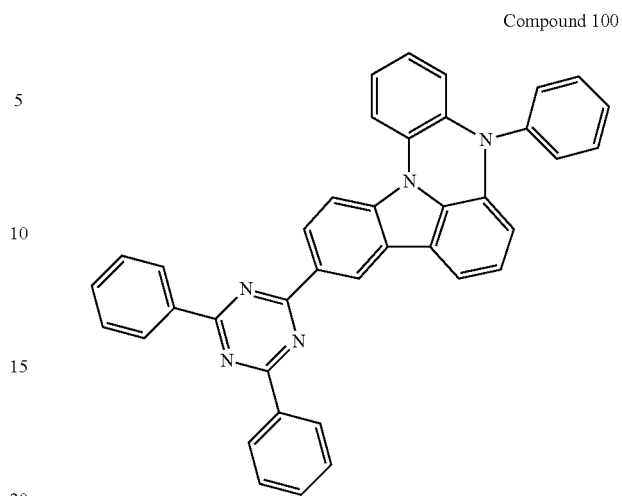

Compound 100

TABLE 1

| | Material for forming an ETL | Efficiency (cd/A) | Lifespan at T95 (6,000 nit) |
|---|---|---|---|
| Example 1 | Compound A1 | 47.3 | 970 |
| Example 2 | Compound A3 | 44.1 | 921 |
| Example 3 | Compound A5 | 45 | 943 |
| Example 4 | Compound A7 | 49.5 | 921 |
| Example 5 | Compound A9 | 50.2 | 991 |
| Example 6 | Compound A20 | 41.5 | 937 |
| Example 7 | Compound A22 | 46.8 | 897 |
| Example 8 | Compound A24 | 43.9 | 911 |
| Example 9 | Compound A26 | 46.1 | 956 |
| Example 10 | Compound A28 | 45.7 | 971 |
| Example 11 | Compound A29 | 48.2 | 923 |
| Example 12 | Compound A35 | 49.6 | 970 |
| Example 13 | Compound A37 | 48.5 | 921 |
| Example 14 | Compound A38 | 45.9 | 943 |
| Example 15 | Compound A45 | 47.2 | 937 |
| Example 16 | Compound A50 | 49.1 | 912 |
| Comparative Example 1 | Alq₃ | 39.8 | 456 |
| Comparative Example 2 | Compound 100 | 43.9 | 799 |

Examples 17-21

Organic light-emitting devices were manufactured in substantially the same manner as in Examples 1-16, except that Alq3 was used to form the ETL instead of the compounds listed in Table 1, and compounds listed in Table 2 were used to form the EML instead of CBP.

Organic light-emitting devices thus manufactured had a configuration of 2-TNATA/NPB/EML [compound of Table 2 corresponding to Examples 17-21+Ir(ppy)₃ 15% doping]/Alq₃/Al, and the results are shown below.

TABLE 2

| | EML | Efficiency (cd/A) | Lifespan at T95 (6,000 nit) |
|---|---|---|---|
| Example 17 | Compound A1 | 56.1 | 726 |
| Example 18 | Compound A5 | 57.4 | 744 |
| Example 19 | Compound A26 | 49.1 | 710 |
| Example 20 | Compound A30 | 52.7 | 684 |
| Example 21 | Compound A50 | 59.3 | 749 |
| Comparative Example 3 | CBP | 39.8 | 456 |

Referring to Tables 1 and 2, it can be seen that the organic light-emitting devices using compounds synthesized according to embodiments of the present inventive concept exhibited significantly better lifespan and efficiency characteristics than those of the organic light-emitting devices of Comparative Examples 1 to 3.

According to the one or more example embodiments as described above, an organic light-emitting device including a compound according to an example embodiment may have high efficiency and long lifespan characteristics.

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

It should be understood that example embodiments described herein should be considered in a descriptive sense only and not for purposes of limitation. Descriptions of features or aspects within each example embodiment should typically be considered as available for other similar features or aspects in other example embodiments.

While one or more example embodiments have been described with reference to the drawing, it will be understood by those of ordinary skill in the art that various changes in form and details may be made therein without departing from the spirit and scope of the present disclosure as defined by the following claims and equivalents thereof.

What is claimed is:

1. A compound represented by Formula 1:

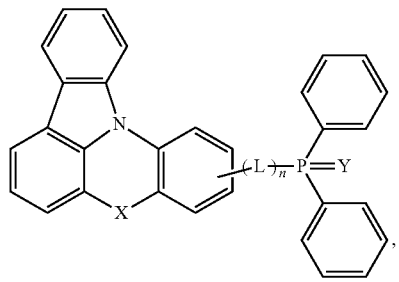

Formula 1 wherein, in Formula 1,
X is selected from $NR_1$, S, O, and $CR_2R_3$,
n is an integer selected from 1 and 2,
Y is selected from O, S, and Se,
$R_1$ to $R_3$ are each independently selected from hydrogen, deuterium, a halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and L is selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, wherein at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group, the substituted $C_6$-$C_{60}$ arylene group, the substituted $C_1$-$C_{60}$ heteroarylene group, the substituted divalent non-aromatic condensed polycyclic group, and the substituted divalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —$N(Q_{11})(Q_{12})$, —Si$(Q_{13})(Q_{14})(Q_{15})$, and —$B(Q_{16})(Q_{17})$;

a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_2$-C$_{60}$ heteroaryl group, a monovalent non-aromatic condensed polycyclic group, and a monovalent non-aromatic condensed heteropolycyclic group; and a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_2$-C$_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_2$-C$_{60}$ heteroaryl group, a monovalent non-aromatic condensed polycyclic group, a monovalent non-aromatic condensed heteropolycyclic group, —N(Q$_{21}$)(Q$_{22}$), —Si(Q$_{23}$)(Q$_{24}$)(Q$_{25}$), and —B(Q$_{26}$)(Q$_{27}$), wherein Q$_{11}$ to Q$_{17}$ and Q$_{21}$ to Q$_{27}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_1$-C$_{60}$ heteroaryl group, a monovalent non-aromatic condensed polycyclic group, and a monovalent non-aromatic condensed heteropolycyclic group.

2. The compound of claim 1, wherein R$_1$ to R$_3$ in Formula 1 are each independently a substituted or unsubstituted C$_1$-C$_{60}$ alkyl group, or a substituted or unsubstituted C$_6$-C$_{60}$ aryl group.

3. The compound of claim 1, wherein L in Formula 1 is a substituted or unsubstituted C$_6$-C$_{60}$ arylene group, or a substituted or unsubstituted C$_1$-C$_{60}$ heteroarylene group.

4. The compound of claim 1, wherein R$_1$ to R$_3$ in Formula 1 are each independently selected from a phenyl group, a biphenyl group, a terphenyl group, and a methyl group.

5. The compound of claim 1, wherein L in Formula 1 is selected from groups represented by Formulae 2a to 2e:

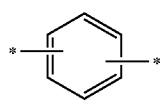

2a

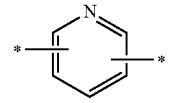

2b

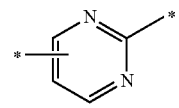

2c

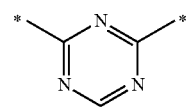

2d

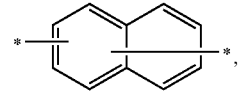

2e wherein in Formulae 2a to 2e, * indicates a binding site.

6. The compound of claim 1, wherein the compound of Formula 1 is represented by Formula 2:

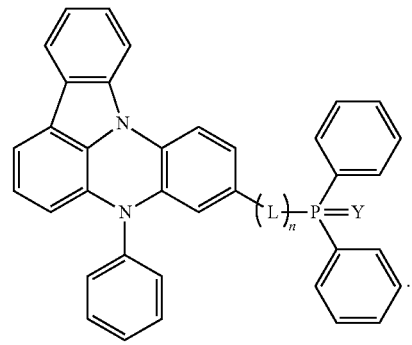

Formula 2

7. The compound of claim 1, wherein the compound of Formula 1 is represented by Formula 3:

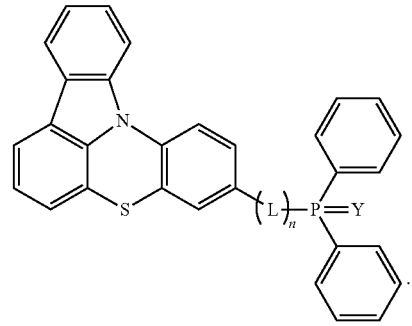

Formula 3

8. The compound of claim 1, wherein the compound of Formula 1 is represented by Formula 4:

Formula 4
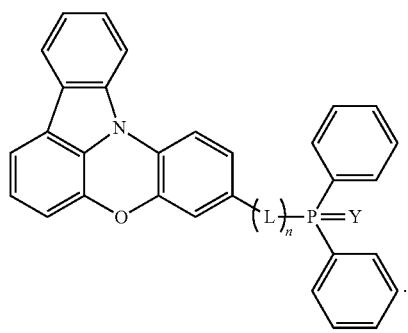
9. The compound of claim 1, wherein the compound of Formula 1 is selected from Compounds A1 to A16 and A18 to A65:
A1
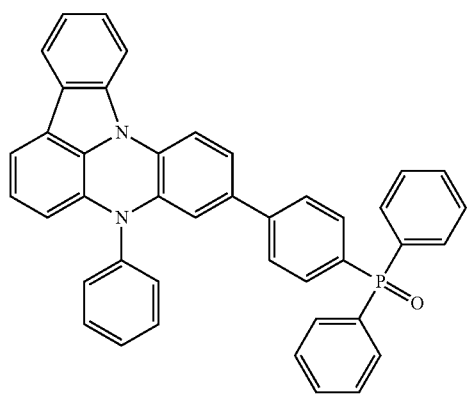
A2
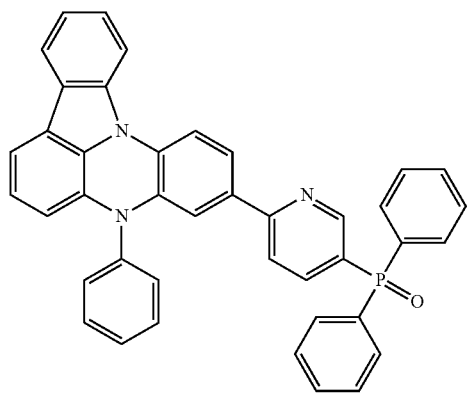
A3
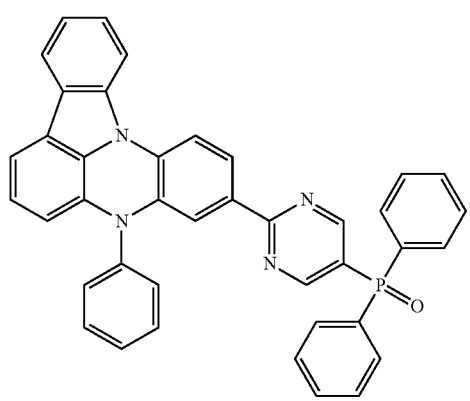
A4
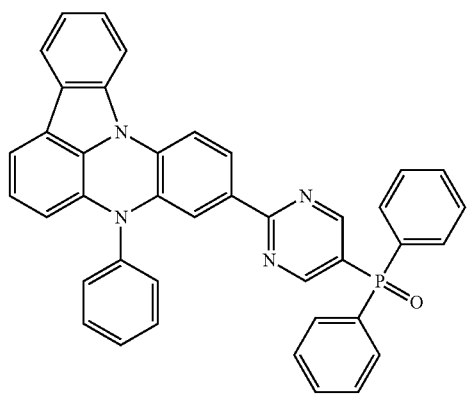
A5
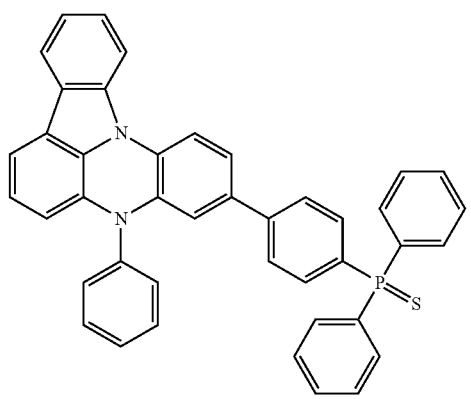
A6
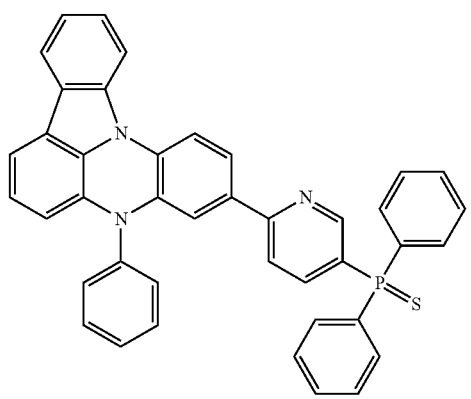
A7
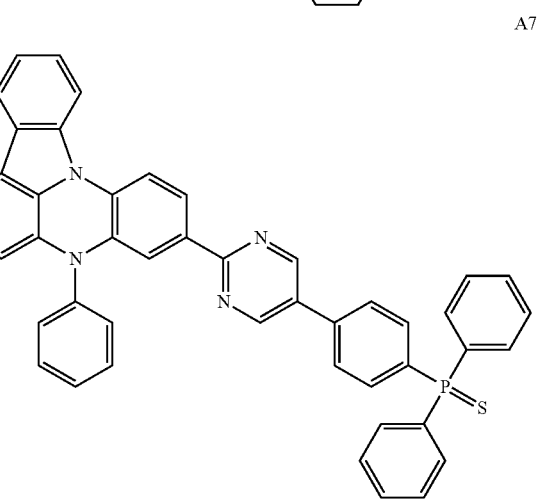

A8
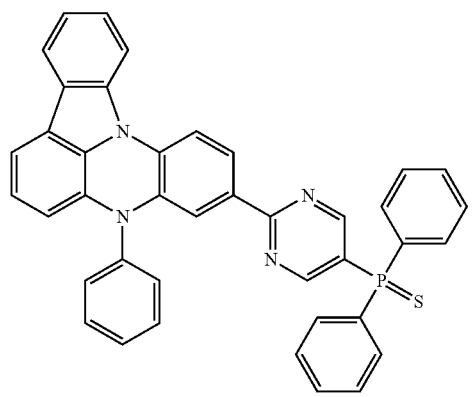
A9
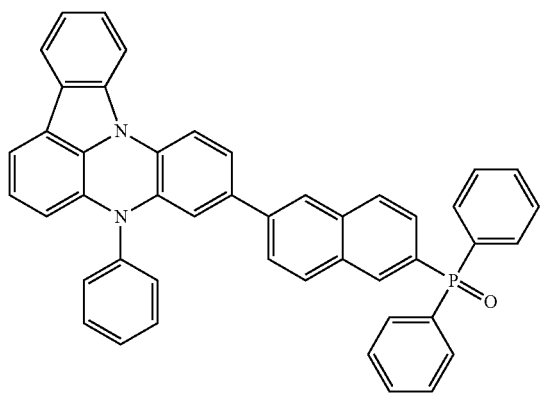
A10
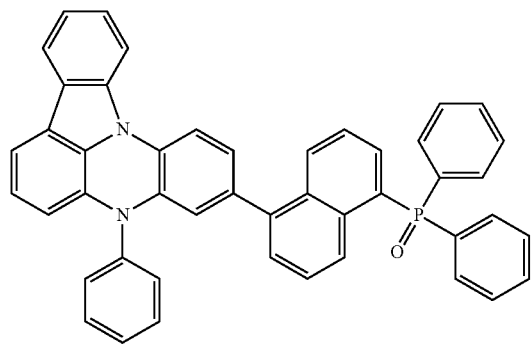
A11
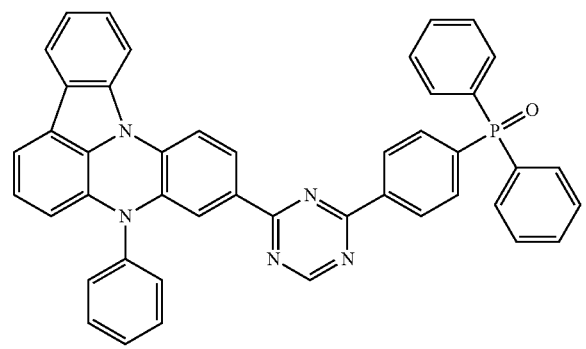
A12
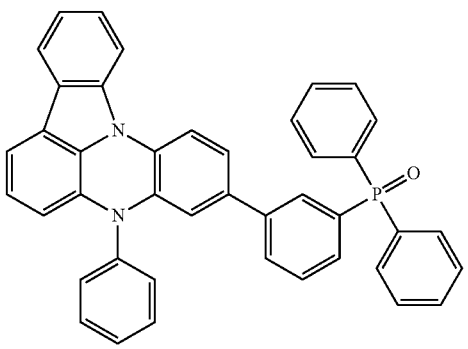
A13
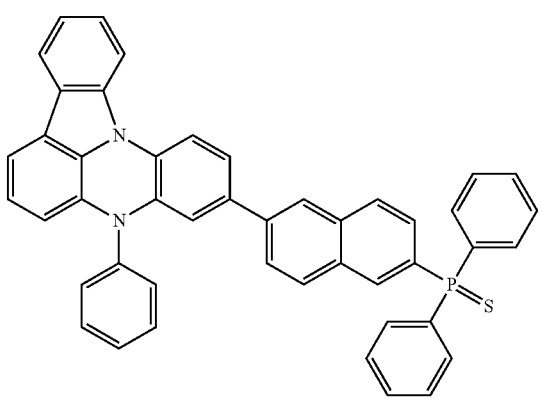
A14
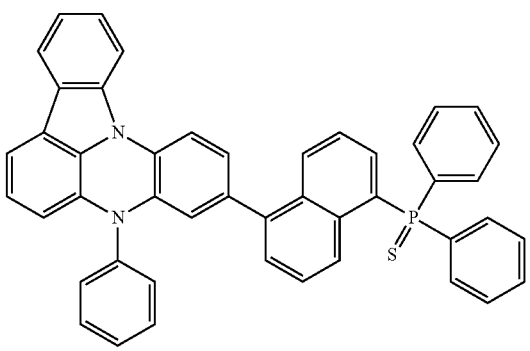
A15
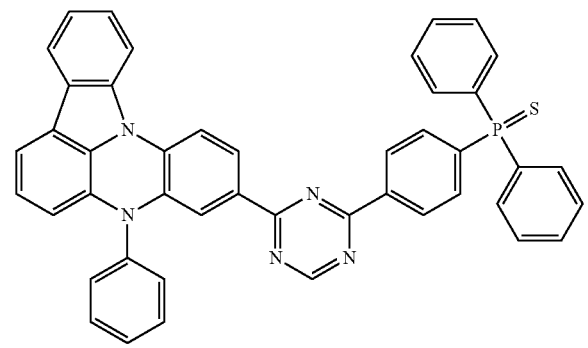

A16
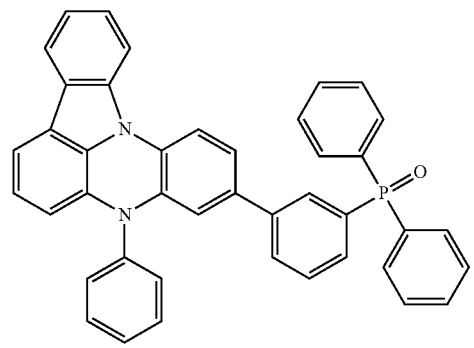
A18
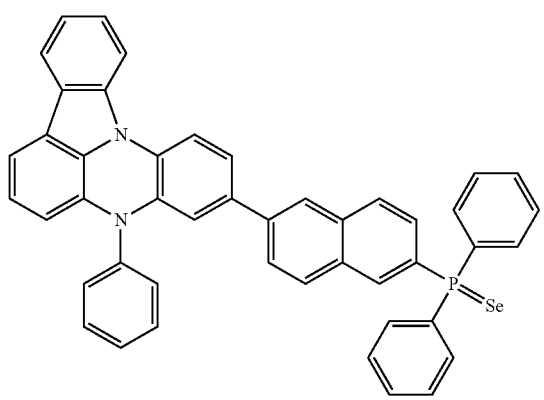
A19
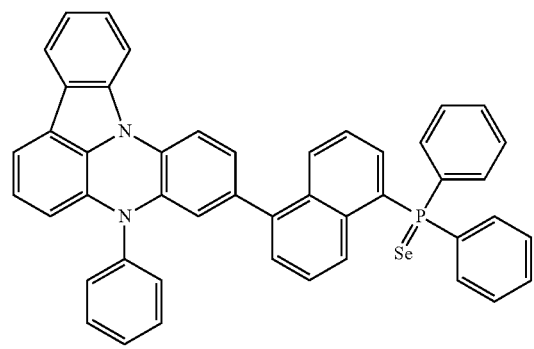
A20
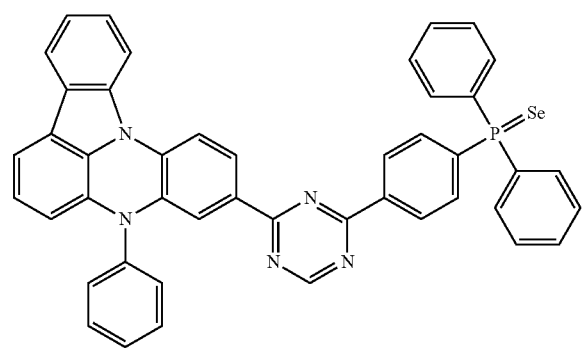
A21
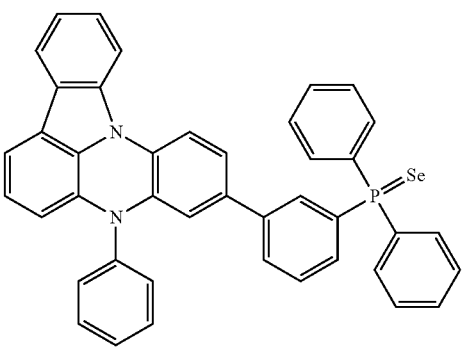
A22
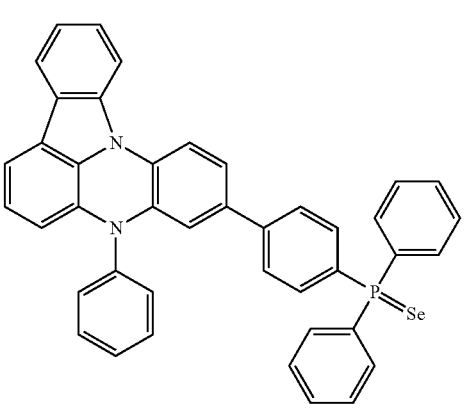
A23
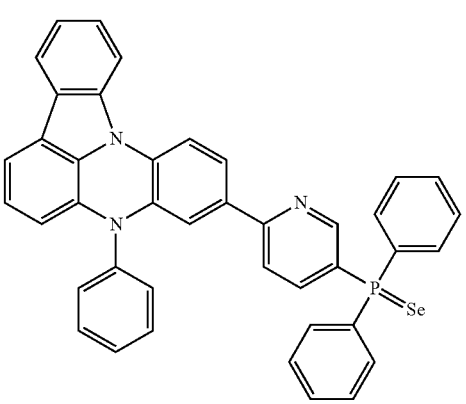
A24
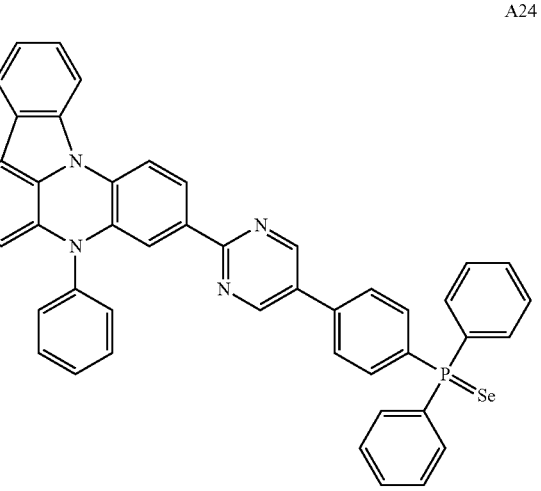

A25
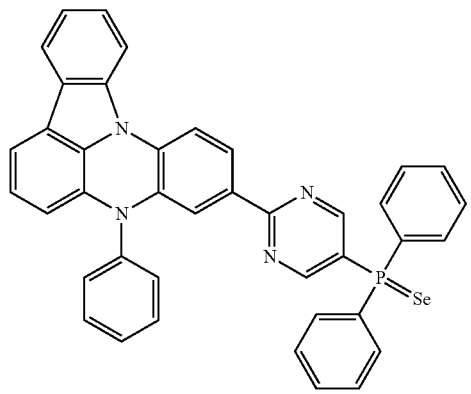
A26
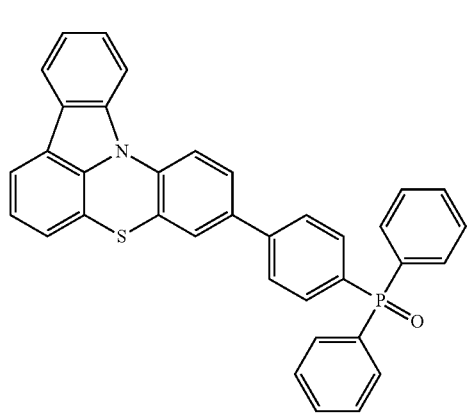
A27
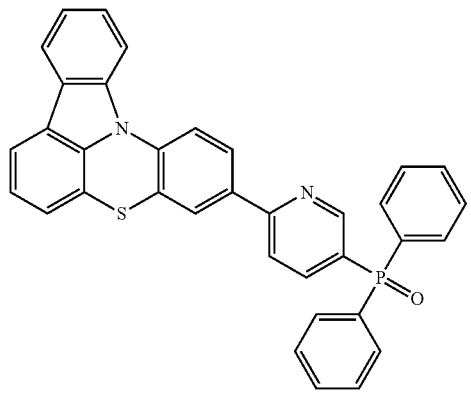
A28
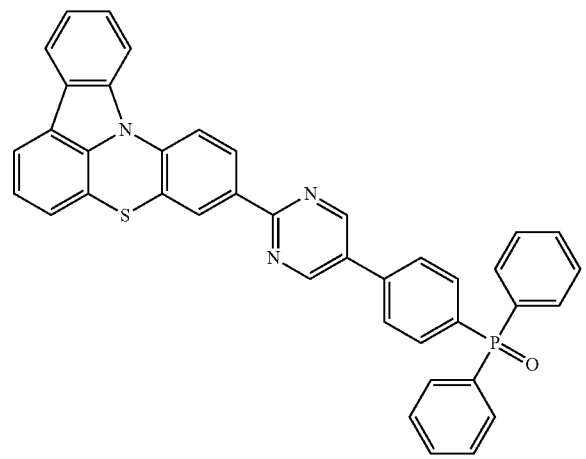
A29
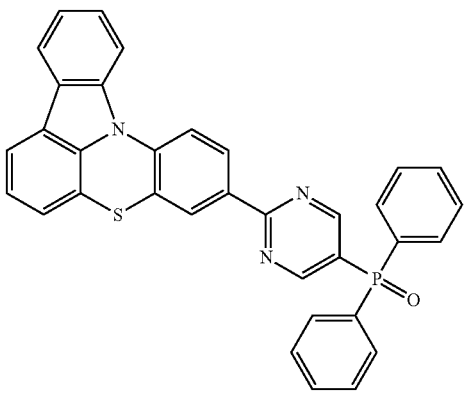
A30
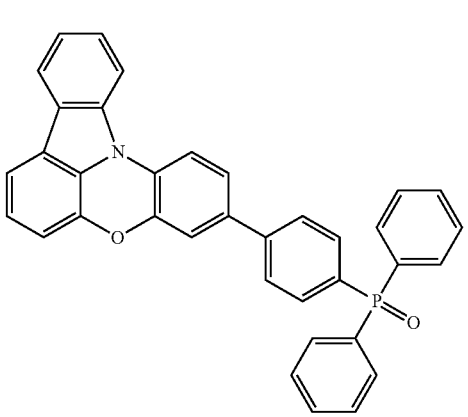
A31
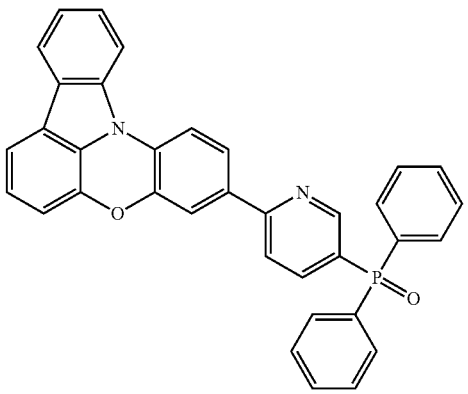
A32
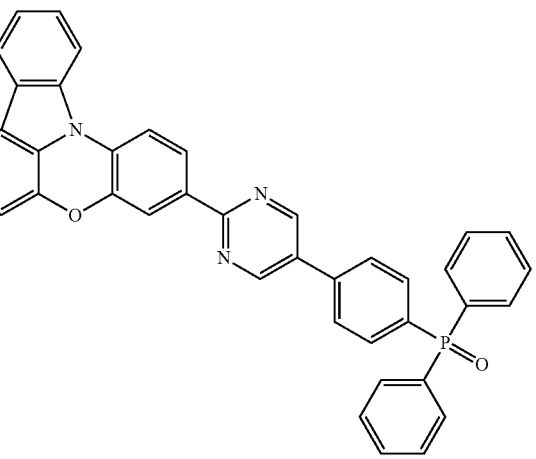

A33
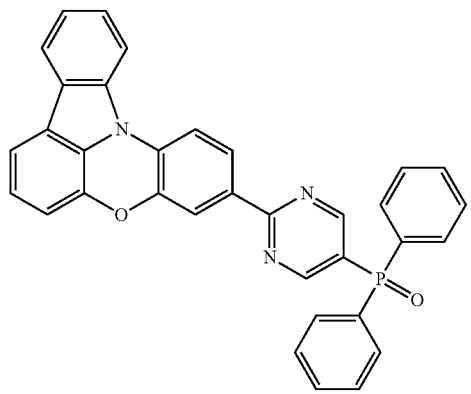
A34
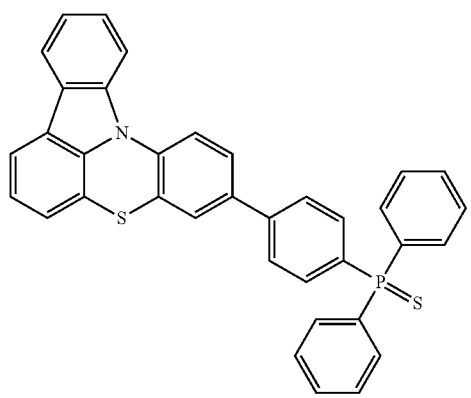
A35
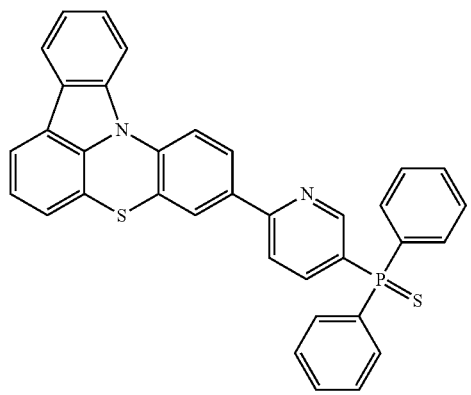
A36
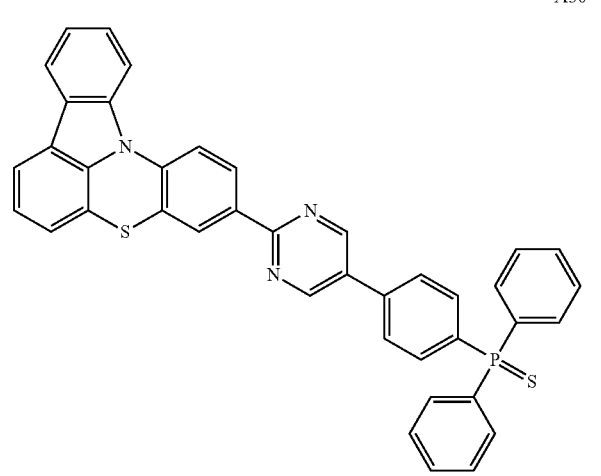
A37
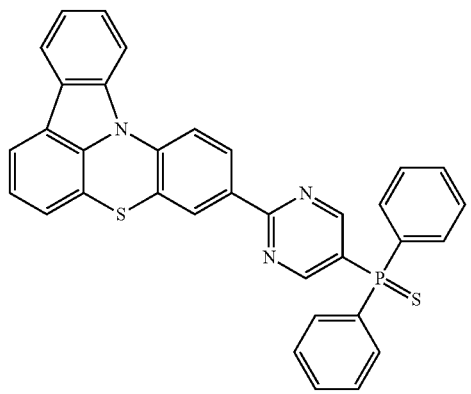
A38
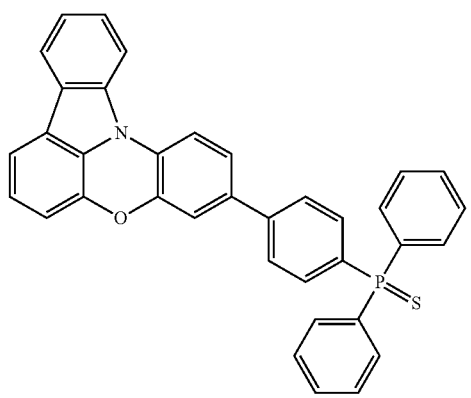
A39
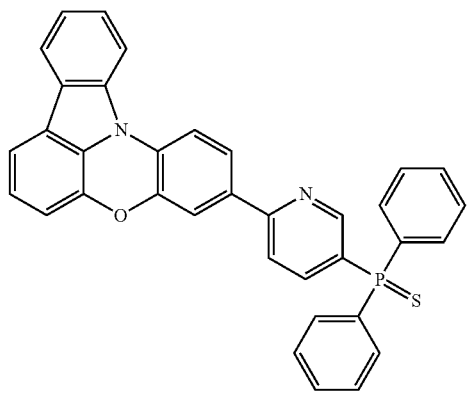
A40
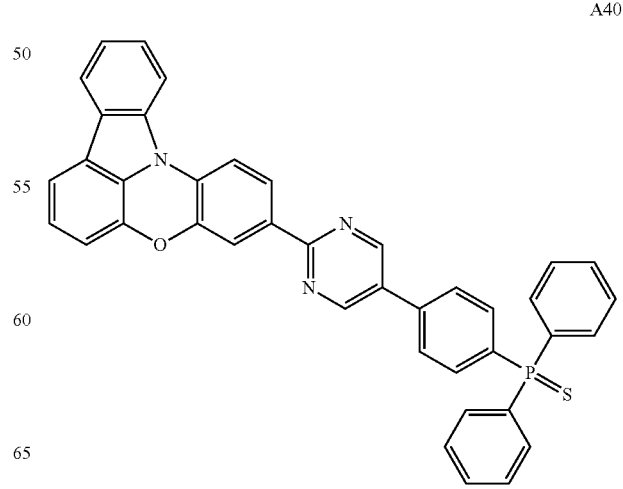

A41 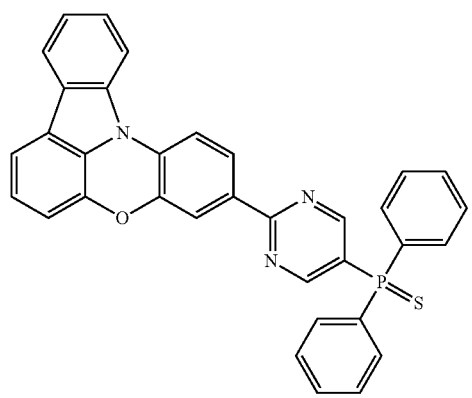
A42 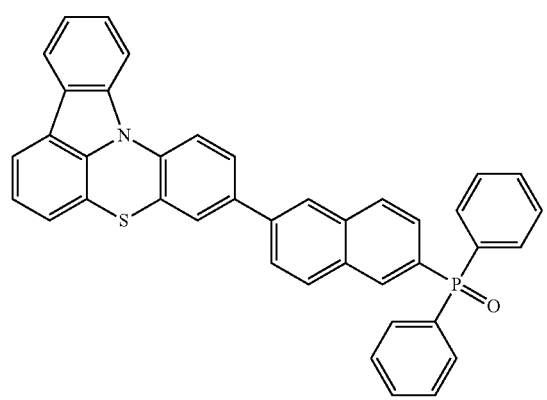
A43 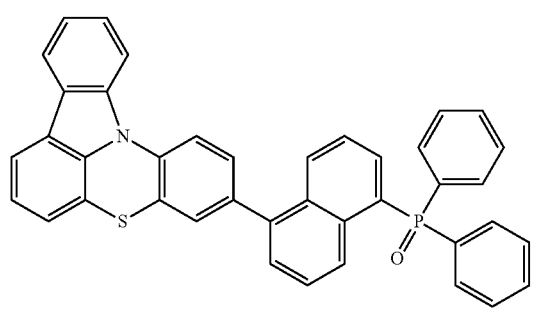
A44 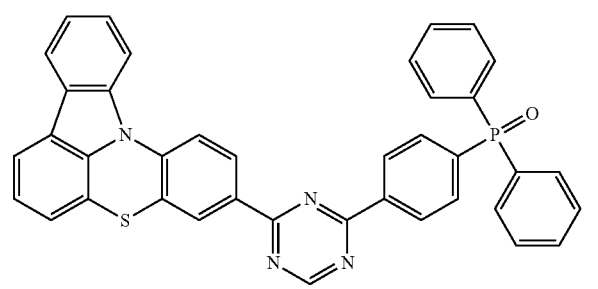
A45 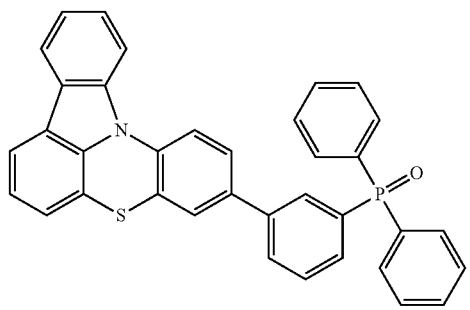
A46 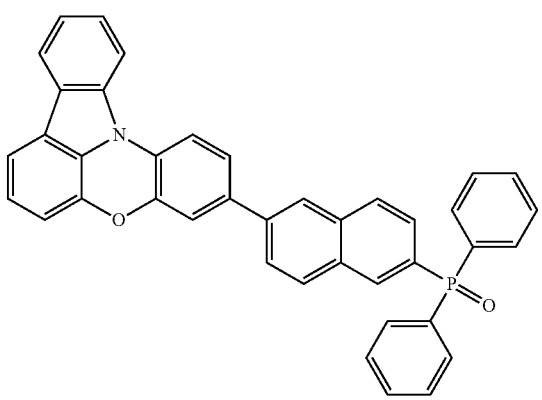
A47 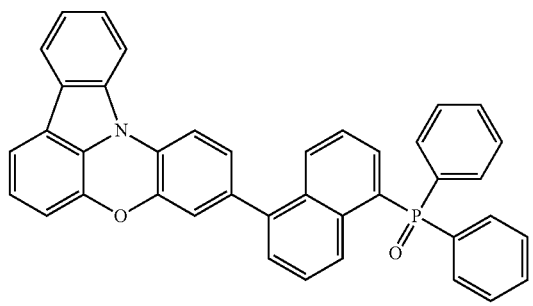
A48 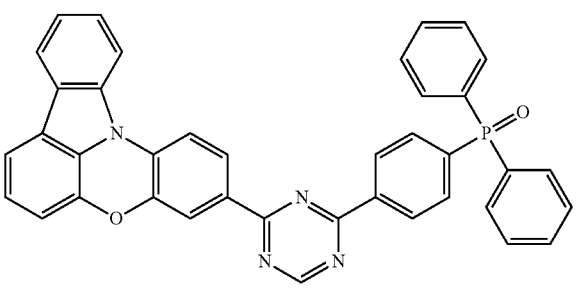

-continued
A49
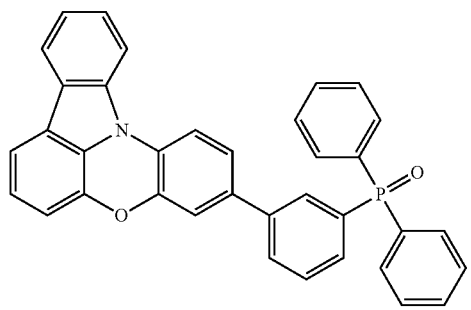
A50
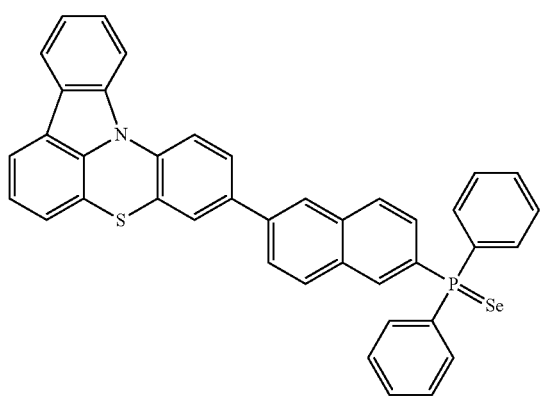
A51
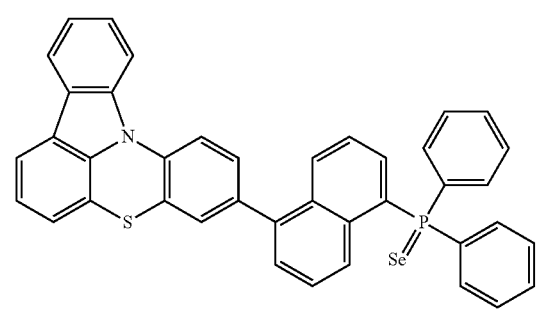
A52
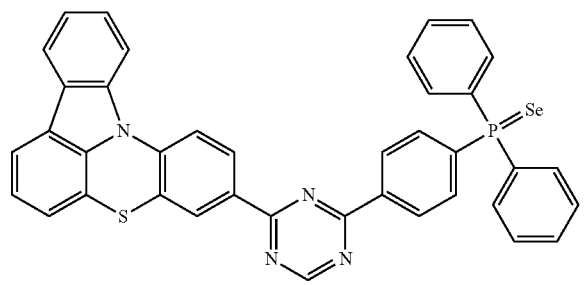
-continued
A53
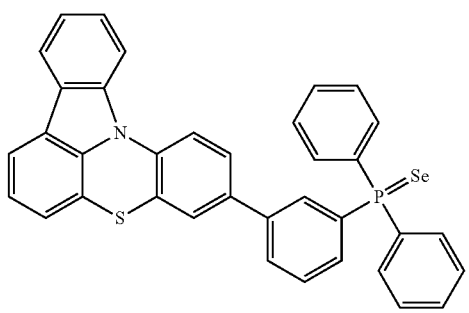
A54
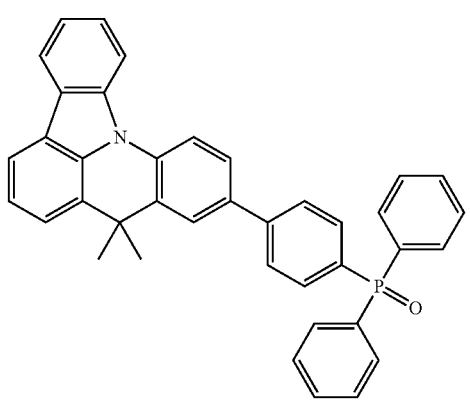
A55
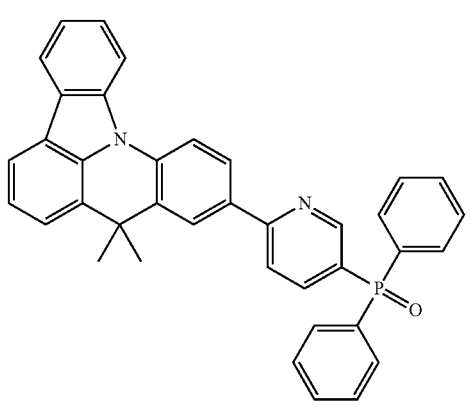
A56
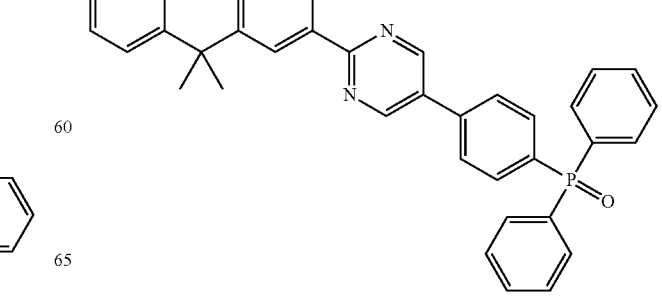

A57
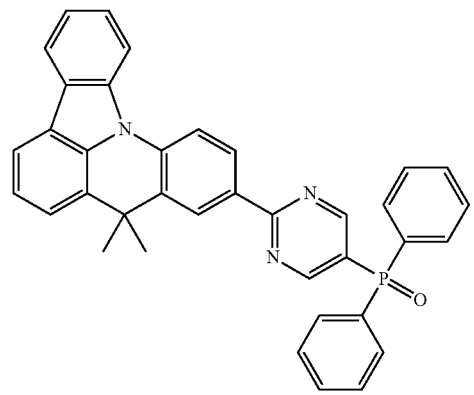
A58
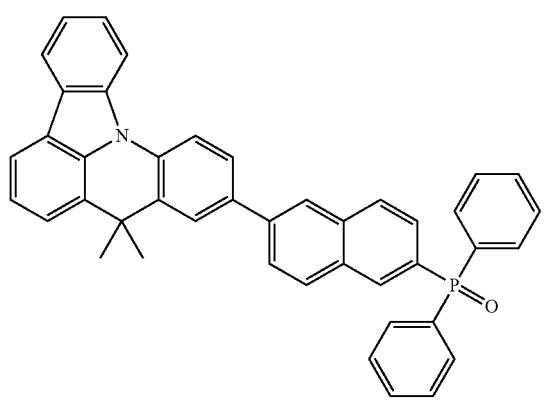
A59
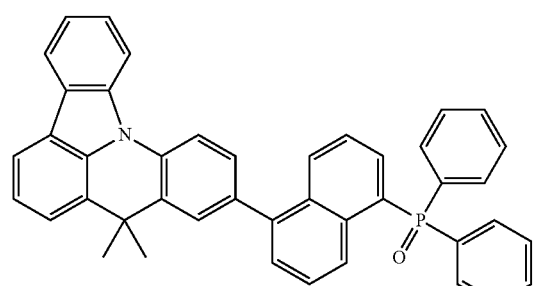
A60
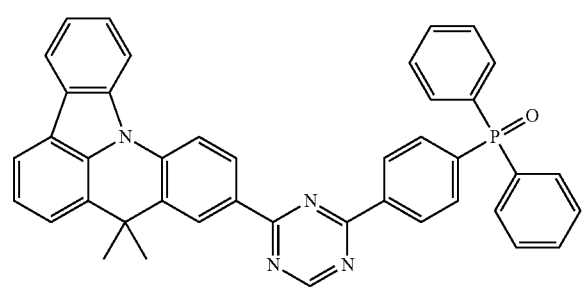
A61
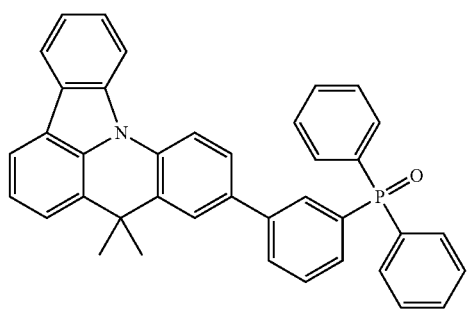
A62
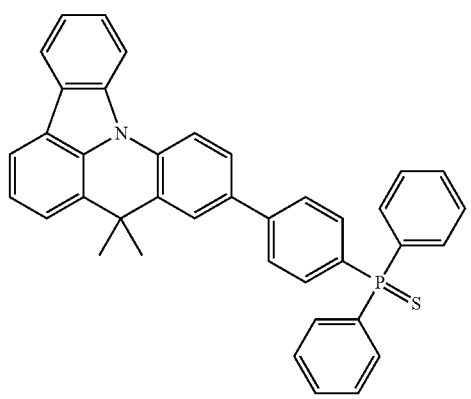
A63
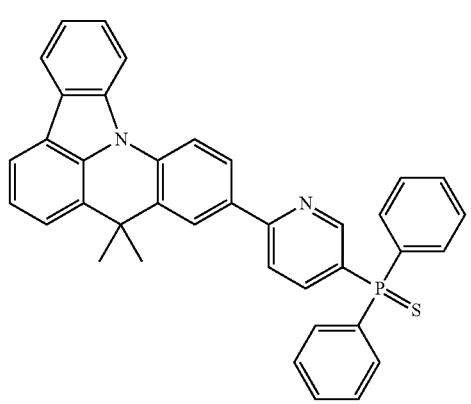
A64
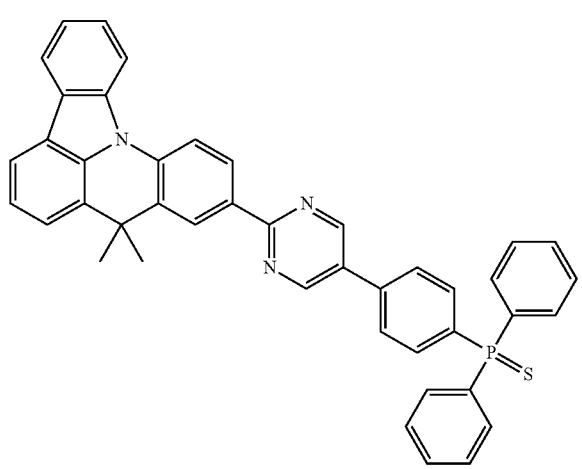

-continued

A65

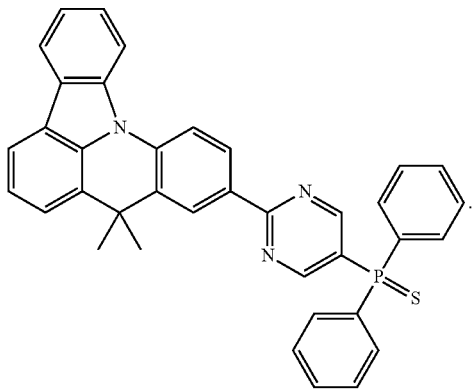

10. An organic light-emitting device, comprising:
a first electrode;
a second electrode facing the first electrode; and
an organic layer between the first electrode and the second electrode, the organic layer comprising an emission layer, wherein the organic layer comprises the compound represented by Formula 1 of claim 1.

11. The organic light-emitting device of claim 10, wherein
the first electrode is an anode,
the second electrode is a cathode, and
the organic layer comprises i) a hole transport region between the first electrode and the emission layer, the hole transport region comprising at least one selected from a hole injection layer, a hole transport layer, and an electron blocking layer, and ii) an electron transport region between the emission layer and the second electrode, the electron transport region comprising an electron transport layer and at least one selected from a hole blocking layer and an electron injection layer.

12. The organic light-emitting device of claim 11, wherein the electron transport region comprises the compound of claim 1.

13. The organic light-emitting device of claim 11, wherein the electron transport layer or the emission layer comprises the compound of claim 1.

14. The organic light-emitting device of claim 11, wherein the hole transport region comprises a charge-generation material.

15. The organic light-emitting device of claim 14, wherein the charge-generation material is a p-dopant.

16. The organic light-emitting device of claim 15, wherein the p-dopant is selected from a quinone derivative, a metal oxide, and a cyano group-containing compound.

17. The organic light-emitting device of claim 11, wherein the electron transport region comprises a metal complex.

18. The organic light-emitting device of claim 11, wherein the electron transport region comprises ET-D1 and/or ET-D2:

ET-D1

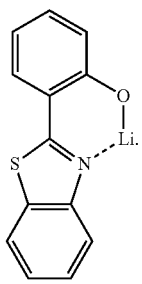

-continued

ET-D2

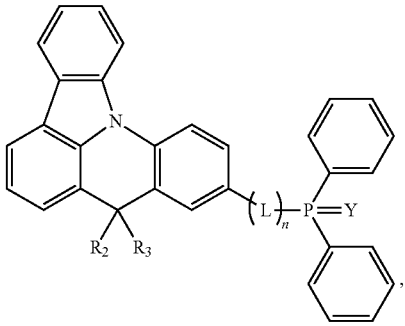

19. A display apparatus, comprising:
a thin film transistor, the thin film transistor comprising a source electrode and a drain electrode; and
the organic light-emitting device as claimed in claim 10, wherein the first electrode of the organic light-emitting device is electrically coupled to the source electrode or the drain electrode of the thin film transistor.

20. A compound represented by Formula 5:

Formula 5 wherein, in Formula 5,
n is an integer selected from 0 to 2,
Y is selected from O, S, and Se,
$R_2$ and $R_3$ are each independently selected from hydrogen, deuterium, a halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_{2-60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and
L is selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, wherein at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group, the substituted $C_6$-$C_{60}$ arylene group, the substituted $C_1$-$C_{60}$ heteroarylene group, the substituted divalent non-aromatic condensed polycyclic group, and the substituted divalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), wherein $Q_{11}$ to $Q_{17}$ and $Q_{21}$ to $Q_{27}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

* * * * *